(12) United States Patent
Lai et al.

(10) Patent No.: US 6,623,620 B2
(45) Date of Patent: Sep. 23, 2003

(54) METHOD FOR DETECTING OR MONITORING SULFUR DIOXIDE WITH AN ELECTROCHEMICAL SENSOR

(75) Inventors: Ann Lai, Beachwood, OH (US); Laurie A. Dudik, South Euclid, OH (US); Chung-Chiun Liu, Cleveland Heights, OH (US)

(73) Assignee: Hathaway Brown School, Shaker Height, OH (US)

( * ) Notice: Subject to any disclaimer, the term of this patent is extended or adjusted under 35 U.S.C. 154(b) by 0 days.

(21) Appl. No.: 09/466,865

(22) Filed: Dec. 17, 1999

(65) Prior Publication Data

US 2003/0155241 A1 Aug. 21, 2003

Related U.S. Application Data

(60) Provisional application No. 60/166,955, filed on Nov. 22, 1999.

(51) Int. Cl.$^7$ .............................................. G01N 27/407
(52) U.S. Cl. ....................... 205/786.5; 204/426
(58) Field of Search ............................ 204/424–429, 204/431, 416, 403, 412, 432, 421; 73/23.3; 205/786.5

(56) References Cited

U.S. PATENT DOCUMENTS 3,719,564 A * 3/1973 Lilly, Jr. et al. ............ 205/781
4,571,292 A 2/1986 Liu et al. .................... 204/412

(List continued on next page.)

OTHER PUBLICATIONS

Pages 184 and 189 of Sawyer et al., "Electrochecmistry for Chemists," $2^{nd}$ ed., John Wiley & Sons, Inc. 1995.*
Imanaka, N., Y. Yamaguchi, et al. "Sulfur Dioxide Detection with a $Na_2SO_4$–$Li_2SO_4$–$Y_2(SO_4)_3$–$SO_3$ Solid Reference Electrolyte by a Solid Reference Electrode." *Journal of the Electrochemical Society*, 134 (1987), pp. 725–728. Mar.
Symnaski, James S. and Stanley Bruckenstein, "Conductometric Sensors for Parts per Billion Sulfur Dioxide Detection." *Analytical Chemistry*, 5 (1986), pp. 1771–1777. Jul.
Fraden, Jacob, "Chemical Sensors" *AIP Handbook of Modern Sensors*, American Institute of Physics, New York, pp. 532–546. 1993 month unknown.

*Primary Examiner*—Nam Nguyen
*Assistant Examiner*—Alex Noguerola
(74) *Attorney, Agent, or Firm*—Renner, Kenner, Greive, Bobak, Taylor & Weber

(57) ABSTRACT

A thick film electrochemical micro-sensor device for detecting or monitoring sulfur dioxide, comprising a substrate to which is applied a working electrode, a counter electrode, a reference electrode, and optionally a heater and a temperature detector, wherein a portion of the electrodes is covered with an insulator, and a portion of the electrodes is covered with an electrolyte. The device is especially useful for detecting or monitoring sulfur dioxide in emission gases. A method of detecting or monitoring sulfur dioxide emissions using the electrochemical micro-sensor device includes contacting the emission gas with the sensor of the present invention, measuring the current output of the sensor, determining if the current output indicates the presence of sulfur dioxide, and generating a signal, that can be used to actuate a scrubber system when a pre-determined level of sulfur dioxide is detected.

18 Claims, 43 Drawing Sheets

U.S. PATENT DOCUMENTS

| | | | |
|---|---|---|---|
| 4,584,867 A | | 4/1986 | Forster .................... 73/25.03 |
| 4,655,880 A | | 4/1987 | Liu ............................ 204/1 T |
| 4,668,635 A | | 5/1987 | Forster ...................... 436/134 |
| 4,720,394 A | | 1/1988 | Kojima et al. .............. 427/102 |
| 4,855,034 A | | 8/1989 | Sugimoto et al. ........... 204/427 |
| 4,865,717 A | | 9/1989 | Setter et al. |
| 4,874,500 A | | 10/1989 | Madou et al. |
| 5,000,180 A | | 3/1991 | Kuypers et al. |
| 5,071,526 A | | 12/1991 | Pletcher et al. .......... 204/153.1 |
| 5,120,421 A | | 6/1992 | Glass et al. |
| 5,215,643 A | * | 6/1993 | Kusangi et al. ............. 204/412 |
| 5,302,274 A | * | 4/1994 | Tomantschger et al. .... 204/412 |
| 5,336,388 A | | 8/1994 | Leader et al. |
| 5,387,462 A | | 2/1995 | Debe ......................... 428/245 |
| 5,431,806 A | * | 7/1995 | Suzuki et al. ............... 204/415 |
| 5,437,772 A | | 8/1995 | De Castro et al. |
| 5,437,999 A | | 8/1995 | Diebold et al. |
| 5,512,159 A | * | 4/1996 | Yoshioka et al. ........... 204/403 |
| 5,514,337 A | | 5/1996 | Groger et al. ........... 422/82.08 |
| 5,656,142 A | * | 8/1997 | Park et al. .................. 204/403 |
| 5,676,820 A | | 10/1997 | Wang et al. |
| 5,876,577 A | * | 3/1999 | McAleer et al. ....... 204/403.11 |
| 5,895,591 A | * | 4/1999 | Kojima et al. .............. 219/209 |
| 5,958,340 A | | 9/1999 | Meyer et al. ................. 422/90 |

* cited by examiner

The Designs of the Set A Thick-Film Electrochemical Micro-Sensors

The Designs of the Set B Thick-Film Electrochemical Micro-Sensors

METHOD FOR DETECTING OR MONITORING SULFUR DIOXIDE WITH AN ELECTROCHEMICAL SENSOR

The present application claims priority under 35 U.S.C. §119(e) from U.S. Provisional Patent Application No. 60/166,955, filed on Nov. 22, 1999.

TECHNICAL FIELD

The present invention is directed to an electrochemical micro-sensor device for detecting or monitoring sulfur dioxide. More particularly, the invention is directed to a thick film electrochemical micro-sensor device capable of detecting and monitoring sulfur dioxide emissions.

BACKGROUND OF THE INVENTION

Acidic deposition, which includes acid rain, acid snow, and even acidic dusts, is currently a major environmental issue. It is not only a critical threat to the natural world but also to the world of man. In recent years, acidic deposition has increased greatly which, in turn, amplifies its effects. It has depleted the fisheries in various lakes around the world. It has also caused the destruction of great forests around the world, especially in Germany. Moreover, acidic deposition is, in itself, damaging human health in various locations. Finally, acidic deposition poses a great threat to the preservation of human history. All these problems will be discussed more thoroughly in the following paragraphs.

First of all, acidic deposition is a main factor behind the depletion of aquatic life in various lakes whether natural or man-made. When acidic deposition occurs, the acidic chemicals mix with the water in the lakes, gradually increasing the acidity of the lakes. Because all species of aquatic life forms can only reproduce and certain eggs can only hatch at certain acidic levels, these species are unable to reproduce regularly if they can reproduce at all. This is a major concern for various fish species as well as certain small shrimps and mollusks. Furthermore, the acidic chemicals from repeated acidic deposition leaches dangerous metals, such as mercury and lead, from the soil at the lake bottoms and into the lake waters. Eventually, the concentration of these toxic-metal substances in the lake reach a certain level where the organisms living within the lake waters start dying off specie by specie. After a certain time, these acidified lakes will look crystal clear, but that will be because there will be nothing living in the lakes except maybe a couple of algae species.

Acidic deposition is also a main cause behind the devastation of major forests around the world, especially in Germany. The acidic deposition descends into the forests and permeates through the soil. Similar to its effects on the lakes, the acidic chemicals once again release dangerous chemicals, such as aluminum, except this time from the soil. These metals instigate a slow process which kills the trees. Another effect of acidic deposition is that the acidic chemicals, once in the soil, displace the nutrients, such as calcium, which are important to trees and other plant life, from the ground. Because of this displacement, the plant life in such forests is unable to absorb the nutrients necessary for its survival from the soil at forest bottoms.

Acidic deposition is not only an environmental problem but also a problem for humans because it is damaging to human health as well. First of all, the acidic chemicals from acidic deposition, especially from acid rain and acid snow, have the ability to leach toxic metals, such as copper and lead, into drinking water for humans. The presence of these metals in everyday drinking water would obviously harm the health of humans who intake this water. Moreover, the acidic chemicals have been found to be the main sources behind the outbreaks of gastroenteritis in places such as the Adirondack Mountains. Furthermore, when in high concentrations, the acids are capable of irritating the human respiratory system causing problems in everyday functions such as breathing. Finally, medical institutions have also suspected that the acidic content of rain, snow, and dust may be the cause of some types of chronic bronchitis and emphysema which would eventually lead to chronic heart disease.

Lastly, another major problem initiated by acid rain is the destruction of human history by the deterioration of man-made historical architectures. History buildings, such as the magnificent Acropolis in Greece and the stunning Pantheon in Rome, have survived the weathering from rain and snow and wind for hundreds of centuries. However, in recent years, with the rapid increase in acidity in rain, snow, and even dust, these famous buildings representing the progress and history of mankind have deteriorated at higher and higher rates. This deterioration is an obvious effect of the corrosive acidic content of the rain. Because these structures are made mostly in limestone and marble which are basic, the acid reacts with the stones and corrodes the surfaces. However, the deterioration not only occurs with stone monuments and buildings, but also affects the metal structures by increasing the rate of oxidation or rust of the metal. Therefore, acid deposition not only plays a significant part in the destruction of the environment but it also affects humans through damaging human health and deteriorating the traces of stepping stones in human history.

There are three main types of acidic deposition. Acidic dust or ashes are acidic chemicals that descend from the sky in the form of dry flaky solids. Another type of acidic deposition is acidic snow or sleet. This type of acidic deposition occurs with the freezing or crystallization of the acid rain while or before it precipitates from the atmosphere. Finally, most importantly, there is acid rain. Acid rain occurs when the acidic compounds released in gaseous form make contact with the moisture in the atmosphere. Then, when the moisture reaches a certain level and descends from the sky, the acidic compounds have already combined with the rain droplets making the rain acidic.

There are two main groups of gases that contribute to the formation of acidic deposition. The first group includes the group of nitrogen oxides. Its main contributors are automobiles. Another, which is the major contributor to acidic deposition, is sulfur dioxide which is released mainly from the smokestacks of industrial buildings. Outside of these two groups, there are some other minor groups of gases that also contribute to acidic deposition, such as carbon dioxide. When these various acidic gases are released into the atmosphere, they come in contact with the moisture in the atmosphere. Then, with the water, the gases form acidic solutions which fall to the ground in the form of acid rain, acid snow, or acidic dust as described in the previous paragraph.

As mentioned previously, the main contributor to acidic deposition is sulfur dioxide. Sulfur dioxide is usually produced as a result of burning coal and oil. It is also often produced as a superfluous product by the processes in refineries, pulp and paper mills, as well as metal smelters. When released into the atmosphere, sulfur dioxide and other oxides of sulfur have the ability to form sulfates with the oxygen as well as aerosols of sulfurous and sulfuric acids with water vapor. All these chemicals eventually come down to the ground in various forms of acidic deposition.

Therefore, sulfur dioxide harms the environment as well as people in the form of acidic deposition. However, in high concentrations, the sulfur dioxide, by itself, is also a problem. It, by itself, possesses the ability to aggravate already present respiratory and cardiovascular diseases including asthma, bronchitis, and emphysema.

Therefore, in order to help in reducing acid rain, the amount of sulfur dioxide released needs to be reduced. Although there are currently processes such as the use of scrubbers or calcium carbonate released into the sulfur dioxide emissions to neutralize the gas, the processes are expensive, and they also cannot monitor the sulfur dioxide levels. Therefore, it is believed that the most effective way to reduce sulfur dioxide would be through monitoring the sulfur dioxide released from industrial smokestacks. This could lead to a more effective way to regulate sulfur dioxide emission levels. There are many ways to measure sulfur dioxide, and one of these ways is through using our newly developed micro-sensor and sensor technology.

There are many types of sensor technology used for detecting gaseous sulfur dioxide. These sensors can determine the presence of and, usually, the amount of sulfur dioxide in an environment. Of these sensors, spectrophotometric analyzers, conductometric sensors, solid electrolyte electrochemical cells, piezoelectric crystal detectors, and interdigital capacitors (IDCs) are more commonly used. Each type along with its advantages and disadvantages will be discussed in the following paragraphs.

Spectrophotometric analysis is currently the standard technology used for the detection of sulfur dioxide. Spectrophotometric analyzers use either ultraviolet or infrared light to determine the presence of as well as the amount of sulfur dioxide present. Although spectrophotometric analyzers may be the standard method of detection, they often suffer from the interfering absorptions from other sources. Moreover, on top of the fact that they are very expensive commercially to manufacture, and the operation of the analyzers is elaborate as well as complicated in that these analyzers contain mechanical moving parts.

Another method of sensing sulfur dioxide is through the application of conductometric sensors. In conductometric sensors, the sulfur dioxide gas diffuses through a gas-permeable membrane and reaches equilibration in a layer of water. Within the thin layer of water, conductometric sensors are positioned. When the sulfur dioxide gas reaches equilibration in the thin water layer, these conductometric electrodes determine the conductance of the sulfur dioxide gas. Using the conductivity measured, the sulfur dioxide level can be determined in ninety to one hundred and twenty seconds. The advantages of these conductometric sensors include high sensitivity to sulfur dioxide. Moreover, they are simpler to operate than the spectrophotometric analyzers. However, they also have their disadvantages, which include being non-specific, meaning that it is difficult for this kind of sensor to differentiate sulfur dioxide from other gases. Furthermore, another disadvantage is their constant need for extensive maintenance in comparison to the maintenance needs of other methods.

Another method for detection of sulfur dioxide employs solid electrolyte electrochemical cells. These cells contain a $Na_2SO_4$—$Li_2SO_4$—$Y_2(SO_4)_3$—$SO_3$ solid electrolyte and a solid reference electrode. These cells determine sulfur dioxide levels through measuring the electromotive force (EMF). They are more compact and less expensive than spectrophotometric analyzers. They are also capable of detecting sulfur dioxide continuously. Moreover, they have the capability to respond only to sulfur dioxide gas even in the parts per billion (ppb) range. However, these solid electrolyte sensors have disadvantages as well. Their disadvantages include the fact that they need a regulated supply of a reference gas mixture containing both sulfur dioxide and air. Another main disadvantage they possess is that these sensors can only operate at the most optimum quality within the restricted temperature range of 783 K and 833 K.

There are also piezoelectric crystal detectors which make up another sector of sensors used for sulfur dioxide detection. When sulfur dioxide gas is bubbled through a mercurous nitrate solution, a mercury displacement reaction occurs producing mercury vapor. Because of the capability of gold to absorb as well as amalgamate mercury, a gold-coated piezoelectric crystal is used. When the mercury vapor reaches the gold-coated piezoelectric crystal, the crystal detects the mercury vapor because a mercury alloy or amalgam is formed. By measuring and monitoring the mercury using the piezoelectric crystal, the concentration of sulfur dioxide in the sample of air can be determined as well. This method is advantageous in that it has good sensitivity for sulfur dioxide because it can detect sulfur dioxide both in the parts per billion (ppb) and in the parts per million (ppm) ranges. Furthermore, these detectors also have good selectivity for sulfur dioxide in that they are capable of distinguishing sulfur dioxide from the other gases in the ambient air. However, these piezoelectric crystal detectors also suffer from disadvantages. The main disadvantage is the concern that they may produce and emit hazardous mercury gas which can cause serious damage and problems.

Finally, there is a method of detecting sulfur dioxide which employs interdigital capacitors or IDCs. These IDCs have organic absorption centers, which are often constructed using organically modified silicates. These capacitors are claimed to have good selectivity for sulfur dioxide, which is an important advantage. However, there is also one big concern facing this method. Because this method is relatively new, there have been insufficient experimental data collected supporting this claim of good selectivity.

More recent technology of electrochemical sensors, involves two main basic types of micro-sensors, thick film and thin film. Thin film electrochemical sensors apply vapor deposition to produce the sensing elements, which makes the sensors more expensive to produce. However, the thickness of these thin film micro-sensors is only a few microns. The other type of electrochemical micro-sensors is the technology of thick-film sensors which apply a silkscreen-like process for printing the sensors, and because of this, the thickness of these micro-sensors is approximately 0.02 inches, making them thicker than thin film sensors.

Of these thick film electrochemical sensors, there are two main branches of configuration. One employs a two-electrode configuration while the other one applies a three-electrode configuration that is more accurate because it includes a reference electrode. A two-electrode configuration combines the counter and the reference electrode into one electrode while the three-electrode one separates the two electrodes making the results more accurate. For both types of sensors, the Gibbs free energy is first calculated from the oxidation-reduction or redox reaction that occurs when the substance being detected is at the working electrode. Then the calculated Gibbs free energy will be used to determine the necessary potential voltage to apply to the working and counter electrodes in relation to the voltage used in the reference electrode to allow the specific redox equation to occur. This calculated potential voltage is applied to the working and counter electrodes of the micro-sensor against the EMF (electromotive force) of the silver-silver-chloride electrode. Furthermore, the corresponding current produced is measured. After many tests are run with the sensor under various concentrations, the results are used to calibrate the sensors by fitting a linear line of concentrations versus current to the data, which can then be used in order to quantify the sulfur dioxide being measured.

This technology of thick film electrochemical micro-sensors has been used in various fields because of its cost efficient as well as uncomplicated method of manufacture and use. They have been used to detected acidity in waters and even for monitoring human health. For example, they have been used in the project CHIME which uses this type of sensors for monitoring the actions of the heart, among which is the rate of heart beats of babies who range from just born to a couple of years old. However, being a relatively new technology, thick-film electrochemical micro-sensors have not yet been applied to either detecting sulfur dioxide or determining the concentration of sulfur dioxide in gaseous samples.

It is therefore an object of the present invention to provide a thick film electrochemical micro-sensor for detecting sulfur dioxide.

SUMMARY OF THE INVENTION

The present invention provides an effective and economical electrochemical micro-sensor device for detecting or monitoring sulfur dioxide comprising a substrate supporting an arrangement of a working electrode, a reference electrode, and a counter electrode, wherein a first portion of the electrodes is covered with an insulator, and a second portion of the electrodes is covered with an electrolyte, and wherein the electrodes are applied to the substrate using a thick film technique.

The present invention more optimally provides an electrochemical micro-sensor device for detecting or monitoring sulfur dioxide comprising a substrate containing an arrangement of a working electrode, a reference electrode, and a counter electrode, wherein a first portion of the electrodes is covered with an insulator, and a second portion of the electrodes is covered with an electrolyte, wherein the electrodes and the insulator are applied to the substrate using a thick film technique, and wherein the sensing portions of the working and counter electrodes are disposed adjacent to each other, with a gap therebetween of less than or equal to about 0.2 inches, in an optimum configuration, as described herein.

The present invention further provides a method of detecting sulfur dioxide in an emission gas comprising contacting the emission gas with the inventive sensor, measuring the current output of the sensor, determining if the current output indicates the presence of sulfur dioxide, and generating a signal. This signal can then be used to activate a display device, a recording means, an alarm device, and/or a compensating means.

The present invention additionally provides a method of detecting sulfur dioxide in an emission gas using at least two micro-sensor devices in a differential mode of operation. The method comprises contacting the emission gas with a first inventive sensor, measuring the current output of the sensor, generating a first signal based on the current output of the sensor, providing at least a second inventive sensor, which has been adapted to detect interference from other chemical species, contacting the emission gas with the second sensor, measuring the current output of the second sensor, generating a second signal, and subtracting the second signal from the first signal. This signal can then be used to activate a display device, a recording means, an alarm device, and/or a compensating means.

It has been found that as the size of the working electrode of the micro-sensors increases, the sensitivity as well as the current output increases because the surface area at which the reaction takes place increases. The efficiency of the micro-sensor device is thus increased as the surface area of the electrodes increases. Novel electrode configurations designed to maximize this effect were tested, and the results are reported herein, along with the preferred electrode configurations.

It has further been found that as the gap between the working and counter electrodes decreases, the sensitivity as well as the output current increases, theoretically because the electrons have less resistance when transferring from the counter electrode to the working electrode. The efficiency of the micro-sensor device is thus increased as the gap between the working and counter electrodes decreases. Novel electrode configurations designed to maximize this effect were tested, and the results are reported herein, along with the preferred electrode configurations.

It has also been found that as the length of the working electrode and counter electrode adjacent to one another increases, the sensitivity as well as the current output increases because there is a greater length of the region where the electrons have less resistance moving from the working electrode to the counter electrode. The efficiency of the micro-sensor device is thus increased as the length of the region where the working electrode and counter electrode are adjacent to one another increases. Novel electrode configurations designed to maximize this effect were tested, and the results are reported herein, along with the preferred electrode configurations.

There exists a linear relationship between the current output and the concentration of the sulfur dioxide because, as the concentration increases, the amount of electrons transferred increases as well, contributing to a higher current output. This linear relationship allows the electrochemical micro-sensor device of the present invention to detect and quantitatively monitor sulfur dioxide emissions.

DETAILED DESCRIPTION OF THE INVENTION

Figure 1A:
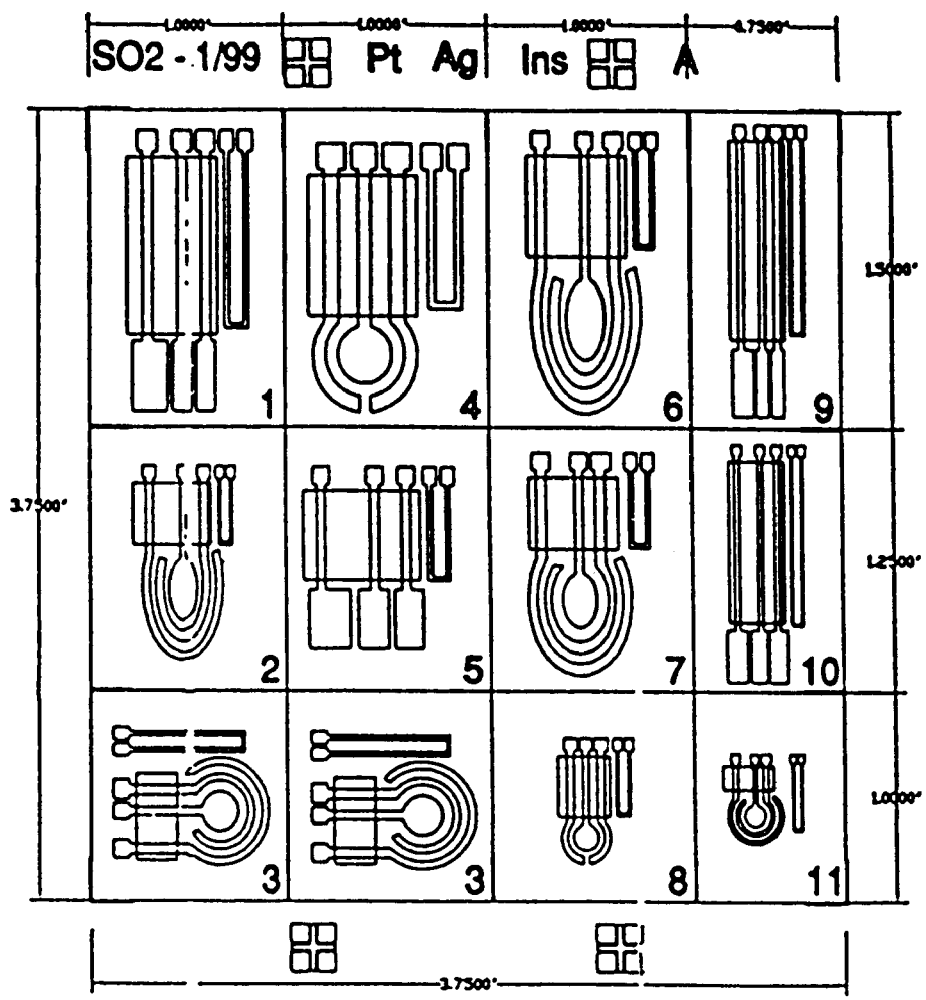
FIG. 1A is a schematic illustration of the design of 11 thick film electrochemical micro-sensors prepared and tested in accordance with the invention, and designated as Set A.

The present invention is directed to a thick film electrochemical sensor device that is capable of being used to detect or monitor sulfur dioxide emission levels such as in the environment near the tops of industrial smokestacks.

The present invention is directed to the fabrication and use of a chip-like thick film electrochemical micro-sensor device with three electrodes (working, reference, and counter electrodes), wherein the electrodes are contacted with an electrolyte, preferably an ion conductive resin or membrane, and optionally including a temperature detector, and a heater. The overall size of the micro-sensor device is preferably on the order of but not limited to about 0.5 $in^2$ to about 2.25 $in^2$, preferably about 1 $in^2$. This sensor is heat-resistant and, therefore, is able to be placed within a smokestack, near the top, to detect and measure sulfur dioxide emissions.

The sensor is preferably made using a thick film technique, including deposition of multiple electrodes on a substrate. Electrochemical sensors and thick film techniques for their fabrication are discussed in U.S. Pat. No. 4,571,292 to C. C. Liu et al, and U.S. Pat. No. 4,655,880 to C. C. Liu, which patents are incorporated by reference as if fully written out below.

The substrate may be formed of plastic, glass, ceramic, alumina, quartz, or any other material that preferably is inert relative to the material from which the electrodes are formed and the material into which the sensor is intended to be placed for use. Preferably the substrate is an alumina ceramic material. Other suitable ceramics include aluminum nitride, beryllia, silicon carbide, silicon nitride, and the like.

The multiple electrodes include at least one each of a working electrode, a reference electrode, and a counter electrode. Preferably, the working electrode and the counter electrode are formed of the same material, although this is not a requirement. The material is preferably inert relative to the substrate and the electrolyte as well as to sulfur dioxide. Examples of materials suitable for the working electrode and the counter electrode include but are not limited to gold, platinum, palladium, silver, silver-silver chloride, and carbon. A preferred material is platinum. The platinum is applied to the substrate in the form of a platinum ink, which is commercially available, or can be made using finely dispersed metal particles, solvent, and a binder.

Specific examples of suitable materials to form the reference electrode are silver-silver chloride and mercury-mercuric chloride (Calomel). Silver-silver chloride is preferred. The silver is applied to the substrate in the form of a silver ink, which is commercially available, or can be made using finely dispersed metal particles, solvent, and a binder. As described in further detail herein, the silver is exposed to chloride solution to produce the silver-silver chloride electrode electrochemically. The silver-silver chloride electrode can also be formed using a thick film silver chloride ink, which is commercially available, or can be made using finely dispersed metal particles, solvent, and a binder.

The sensor device of the present invention may optionally further include a temperature detector, which preferably comprises platinum. The platinum is applied to the substrate in the form of a platinum ink, similarly to the working and counter electrodes.

As a further option, the sensor device of the present invention may include a heater. The heater can be printed onto the opposite side of the ceramic substrate from the electrodes, using a conductive material, for example, a serpentine platinum ink pattern, such as the design shown in FIG. 25, to regulate the temperature at which the micro-sensor will operate. Other suitable materials include for example carbon, gold, and other metals. Since the efficiency and specificity of the micro-sensor device is temperature dependent, it is desirable to maintain the sensor at a constant temperature. This is especially useful when the sensor is employed in an industrial setting to detect or monitor sulfur dioxide emissions within a smokestack. The sensor is heated to a temperature greater than the internal temperature of the smokestack, and maintained at a constant level, to avoid the need to recalibrate the sensor at various temperatures.

The electrodes of the sensor device of the present invention may include a connect portion and a sensing portion. The sensing portion of the electrode is exposed to the environment, and is in contact with an electrolyte, preferably an ion conductive material. The sensing portion functions to detect the target species, namely sulfur dioxide. The connect portion of the electrode connects the electrode to an electrical circuit, and is protected from the environment by an insulator. The insulator used to protect the connect portion of the electrodes of the present invention is preferably glass, or glass-containing dielectric materials, and is applied in the form of an insulating ink. Other suitable insulators include but are not limited to polymeric insulating materials and oxide-based insulating materials. In a preferred embodiment, wires are soldered to the connect portion of the electrodes using indium solder. The wires and the solder are then covered with a silicone paste.

After the sensor device is formed, the electrolyte is applied to the sensing portion of the electrodes. The electrolyte preferably comprises a Nafion™ ion conductive material membrane or resin, but may also be other polymeric ionic conductive materials. The electrolyte resin or membrane is allowed to dry, but, during testing and use, the sensor device must be kept moist. If the sensor device is used to detect sulfur dioxide in gas phase emissions, the sensor electrolyte must be wetted periodically, such as being sprayed or misted with water.

According to the invention, 17 different sensor designs were drawn on AUTO-CAD™, a computer drafting program. Then, through a thick film process, which is similar to the silk screening process, silver, platinum, and insulating precursor inks were printed onto alumina ceramic substrates to form the three electrodes and the temperature detector. The silver was treated with chloride to form silver-silver chloride, the material used for the reference electrode, and platinum was used for the temperature detector, the counter and working electrodes, and optionally the heater. The micro-sensors were heated to solidify the components, the wires were soldered to the contacts, and silicone paste was applied. Finally, the sensors were tested by exposure to sulfur dioxide concentrations of from 0 to about 2% in air.

For these thick film electrochemical sensors with a three electrode configuration, the Gibbs free energy calculated from the oxidation-reduction or (redox) reaction of the substance being detected at the working electrode was used to determine the applied potential voltage needed to enable the specific redox reaction to occur. Then the corresponding current produced was measured, and the current was used to quantify the sulfur dioxide levels.

In the fabrication process of sensor examples 1–15, a Rubylith™ cutter was used to draw and cut enlarged designs for each layer of the sensor on red Rubylith™ sheets. Afterwards, tweezers were used to lift away the areas representing where the chemicals for each layer should be applied. Next, the image was transferred with a camera that reduces the designs onto photosensitive glass plates. The plates were then developed, and used to transfer the design onto photosensitive emulsion sheets. These sheets were fixed onto stainless steel mesh screens and block-out material was spread on the areas of the screen where the chemicals should not go through. These mesh screens were the templates for the thick film process.

The screens were loaded into a pneumatic machine, the thick-film printer, to "silk-screen" the silver, the platinum, and the insulator precursor ink individually onto the alumina ceramic substrates. After the thick film process, the ceramic substrates were placed into a drying oven and heated to remove the solvent. A preferable temperature is approximately 100° C., although a range of temperatures may be used. Next, the substrates were fired in a furnace to solidify the inks onto the substrates. A suitable temperature is approximately 850° C., although a range of temperatures may be used. Afterwards, the substrates were diced using a diamond saw into individual devices. Finally, a Nafion™ resin or membrane was applied manually onto the sensing portion of each electrode to serve as an electrolyte.

SPECIFIC EMBODIMENTS OF THE INVENTIONS

EXAMPLES 1–15.

| Part I - Material For Preparing Sensors | |
|---|---|
| AUTO-CAD Computer Program | drying oven |
| Rubylith ™ cutter | furnace |
| red Rubylith ™ sheets | diamond saw |
| transparencies | scissors & scalpel & wire strippers |
| tweezers | indium |
| box camera | 0.75 M Flux |
| photosensitive plates | wires (black, red, and green) |
| developer, fix, and wash (chemical solutions used to develop the photosensitive plates) | soldering pen (can heat up to 999° C.) and holder |
| emulsion sheets | silicone paste |
| stainless steel mesh screens | 0.1 M HCl solution |
| ultraviolet light | Bi-Potentiostat & connecting circuit wires |
| paper towels | 1000-ml beaker |
| block-out | platinum mesh screen |
| thick film printer (a pneumatic machine) | eraser on mechanical pencils |
| silver precursor ink | de-ionized water |
| platinum precursor ink | Nafion ™ (5% fluorinated ion-conductive resin) |
| alumina ceramic substrates | timer |
| blue insulator precursor ink | pipet and pipet tips |

| Part II - Materials For Testing Of The Sensors |
|---|
| 15 developed thick film electrochemical micro-sensors for sulfur dioxide wires (three different colors) |
| approximately 2% sulfur dioxide gas in air |
| gas mixer |
| air |
| tubes for transferring gases |
| potentiostat |
| ring stand |
| aspirating tube |
| 0.005 M potassium nitrate solution |
| aspirating Erlenmeyer flask |
| de-ionized water |
| rubber stoppers (with tube to let stream of gas through) |
| masking tape & scissors |
| computer & printer |
| CHI660A chemistry workstation computer program |
| Slide Write computer program |
| 50 ml & 100 ml beakers & cardboard |
| tiny screw driver (-) |
| timer |

EXPERIMENTAL PROCEDURES

The thick film electrochemical sensors according to the invention were fabricated according to the procedure below.

Figure 1B:
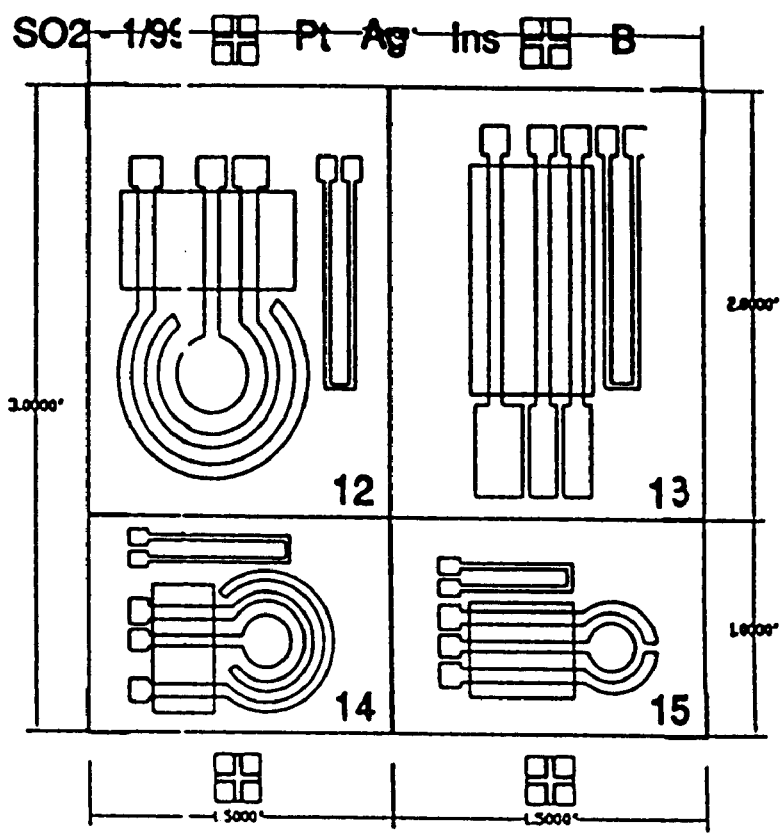
FIG. 1B is a schematic illustration of the design of 4 thick film electrochemical micro-sensors prepared and tested in accordance with the invention, and designated as Set B.

The drawings contain the design of 15 thick film electrochemical micro-sensors prepared and tested in accordance with the invention, separated into Set A (FIG. 1A), and Set B (FIG. 1B).

FIGS. 6A–20B demonstrate the results obtained from the test runs for all 15 sensors. Included for each sensor are graphs which sweep the voltages from –0.6V to 1V for the corresponding current outputs. Further, for each sensor there is a scatter plot graph of the data, the fitted line and the curve fitting coefficients.

Part I: Design & Development

1.) Utilize the computer program AUTO-CAD.

2.) Create and draw 15 designs on AUTO-CAD in full detail including dimensions in two sets; Set A (3.75"× 3.75") with 11 designs and 1 repetition and Set B (3"×3") with 4 designs. Note: Make separate color layers for each chemical. Color the reference electrode layer pink for silver; temperature detector, the counter, and the working electrode aqua for platinum; the insulator dark blue for insulating ink, and the border of each sensor black to mark the size of the alumina ceramic substrate.

3.) Create alignment marks in the corners of the designs for each set.

4.) Draw dicing marks at the corners as well as at the two ends of each line which need to be diced or cut.

5.) Convert the AUTO-CAD file into the type of programming form used by the Rubylith™ cutter.

6.) Run the Rubylith™ cutter to enlarge and to cut the designs for each layer of Set A on red Rubylith™ sheets.

7.) Use tweezers to lift away the areas of the Rubylith™ representing where the chemicals need to be applied.

8.) Prepare to develop sensor materials in a dark room.

9.) Move into a separate room containing the green light board.

10.) Tape the sheet of Rubylith™ for Set A platinum onto the green light board.

11.) Position the camera and open the lens to test take the image.

12.) Reduce the size of the Rubylith™ image and transfer the image onto a photosensitive plate using the camera which exposes the plates to the green light from the light board for about 1 minute 30 seconds to about 2 minutes.

13.) Take the plate to the dark room. Note: Do not expose it to any light.

14.) Develop the plates by placing them for 4 minutes in the developer, 30 seconds in the fix, and 4 minutes in the wash. Note: rock the trays containing the solutions back and forth throughout the development to keep fresh solutions on the plates.

15.) Wash the plates under running water and dry them.

16.) Repeat steps 10–15 for all of the layers in Set A (silver and insulating ink).

17.) Move to another dark room containing the ultraviolet light source.

18.) Cut out three sheets of emulsion about the size of the photosensitive plates.

19.) Place each plate over an emulsion sheet under the ultraviolet light source for half an hour or more.

20.) Place the emulsion sheets individually in the developer for approximately 4 minutes.

21.) Run the sheets under hot water to remove the areas where the chemicals need to be applied.

22.) Place each emulsion sheet the red sticky side up.

23.) Press the stainless steel mesh screen on top of each emulsion sheet and press a paper towel on top of it to absorb the extra emulsion.

24.) Leave the stainless steel mesh screens to dry.

25.) Apply block-out to areas where the chemicals should not go through.

26.) Allow these mesh screens to dry again to become the templates for the thick film process.
27.) For Set B, print out the designs onto transparencies with one transparency for each layer.
28.) Repeat steps 17–26, except this time using the transparencies rather than the developed photosensitive plates.
29.) Load the template for the reference electrodes for Set A into a pneumatic machine, thick-film printer.
30.) Bring the template into contact with the substrate and align.
31.) Spread the silver precursor ink onto the loaded template.
32.) Apply the reference electrode precursor ink by "silk-screening" the silver precursor ink onto the substrate.
33.) Repeat step 32.
34.) Repeat this process for as many sensors as desired.
35.) Apply the working electrode precursor ink, counter electrode precursor ink, and temperature detector precursor ink by loading the appropriate template and "silkscreening" the platinum precursor ink onto the substrate, as in steps 29–34.
35.) Apply the insulating precursor ink, using the technique described above in steps 29–34.
36.) Place the substrate onto which the electrode precursors have been applied into a drying oven and heat at about 100° C. for about ½ hour to remove the solvent.
37.) Fire the substrate in a furnace at about 850° C. for about 1 hour to cure the electrode precursors and solidify the sensor device.
38.) Dice the sensor device along the dicing marks using a diamond saw.
39.) Repeat steps 29–38 for Set B.
40.) Break the sensors along the diced lines into separate pieces.
41.) Cut the indium into small pieces.
42.) Cut wires red, green, and black into 15 cm lengths with one of each for each sensor device.
43.) Expose about 0.5 cm of bare wire on either end.
44.) Spread the flux onto the patches of the silver and platinum where the wires need to be soldered.
45.) Heat the soldering pen up to approximately 535° C.
46.) Use the pen to melt the indium onto the patches on the sensors that have been covered by flux.
47.) Dip one end of each wire into the flux and cover with indium using the pen.
48.) Once again, use the pen to melt the indium on the wire with the indium on the sensors.
49.) Repeat steps 44–48 for each sensor device.
50.) Clean each sensor using methanol and then dry.
51.) Apply silicone paste to cover the bare wires and the indium.
52.) Allow the silicone paste to solidify overnight.
53.) Twist the free ends of the wires connected to the silver electrodes of three to five micro-sensors together, so they can be exposed to chloride simultaneously.
54.) Clean the silver surface using a mechanical pencil eraser.
55.) Fill a 100-ml beaker with 800 ml of the chloride solution.
56.) Connect a platinum screen to the negative side of the potentiostat.
57.) Connect the twisted wires to the positive.
58.) Place both the screen and the sensors into the beaker without allowing them to touch one another.
59.) Turn the voltage to 0.5V.
60.) Clean the silver surfaces first by turning the power up for 5 seconds and down for 5 seconds three times.
61.) Allow the chloride to react with the silver to form silver-silver-chloride by leaving the power on for 2 minutes.
62.) Repeat steps 57–61 for all of the sensors.
63.) Rinse the sensors using warm water and de-ionized water.
64.) Place them on paper towels to dry.
65.) Apply Nafion™ resin or membrane, which will serve as the electrolyte, manually onto the sensing portion of each electrode individually using the pipet and a clean pipet tip.

Figure 2A:
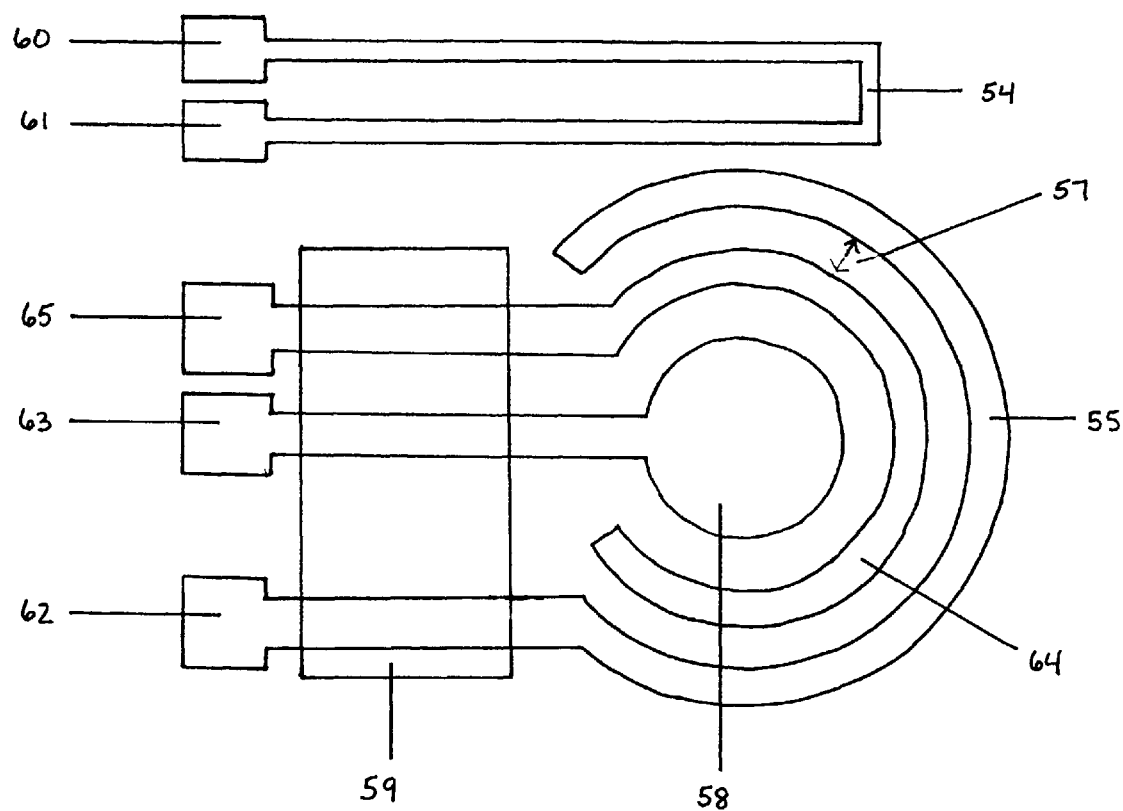
FIG. 2A is a schematic illustration of a preferred sensor configuration, example no. 3, in accordance with the present invention, employing a substrate, working electrode, counter electrode, reference electrode, and temperature detector.

One preferred sensor design is shown in FIG. 2A. The micro-sensor device shown is the example number 3 from FIG. 1A. The temperature detector 54 and contacts 60, 61 are platinum. The counter electrode 55 and working electrode 64, with gap 57 between them, are also platinum. The reference electrode 58 is silver-silver-chloride. The contacts 62, 63, 65 provide sites to connect wires. A portion of the electrodes is covered with glass insulator 59.

Figure 2B:
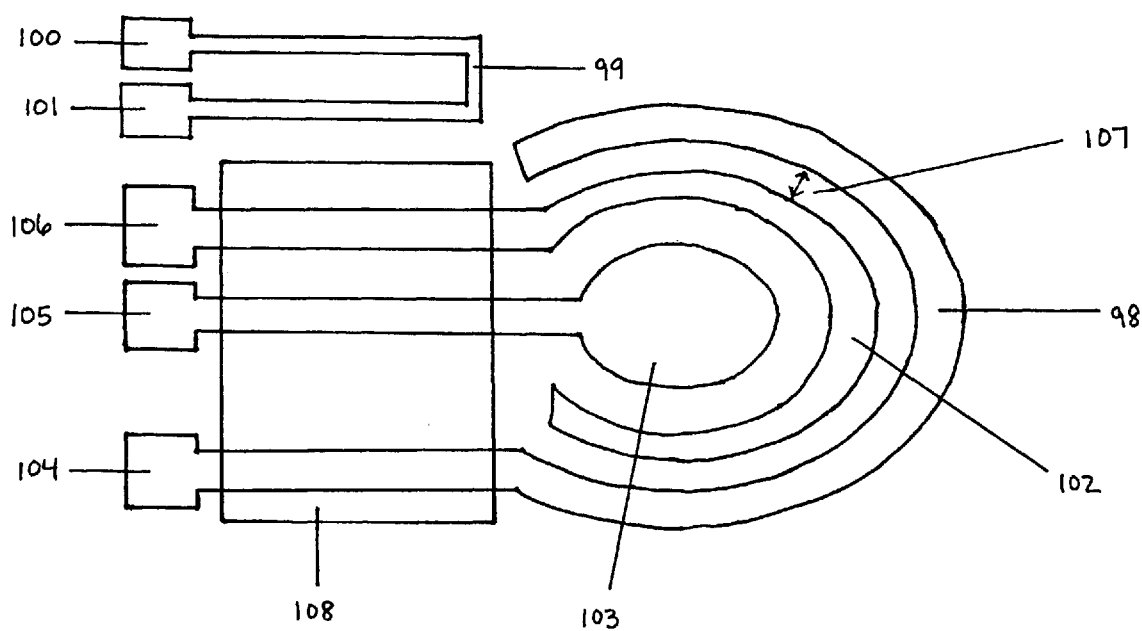
FIG. 2B is a schematic illustration of a second preferred sensor configuration, example no. 7, in accordance with the present invention, employing a substrate, working electrode, counter electrode, reference electrode, and temperature detector.

A second preferred sensor design is shown in FIG. 2B. The micro-sensor device shown is the example number 7 from FIG. 1A The temperature detector 99 and contacts 100, 101 are platinum. The counter electrode 98 and working electrode 102, with gap 107 between them, are also platinum. The reference electrode 103 is silver-silver-chloride. The contacts 104, 105, 106 provide sites to connect wires. A portion of the electrodes is covered with glass insulator 108.

Figure 3:
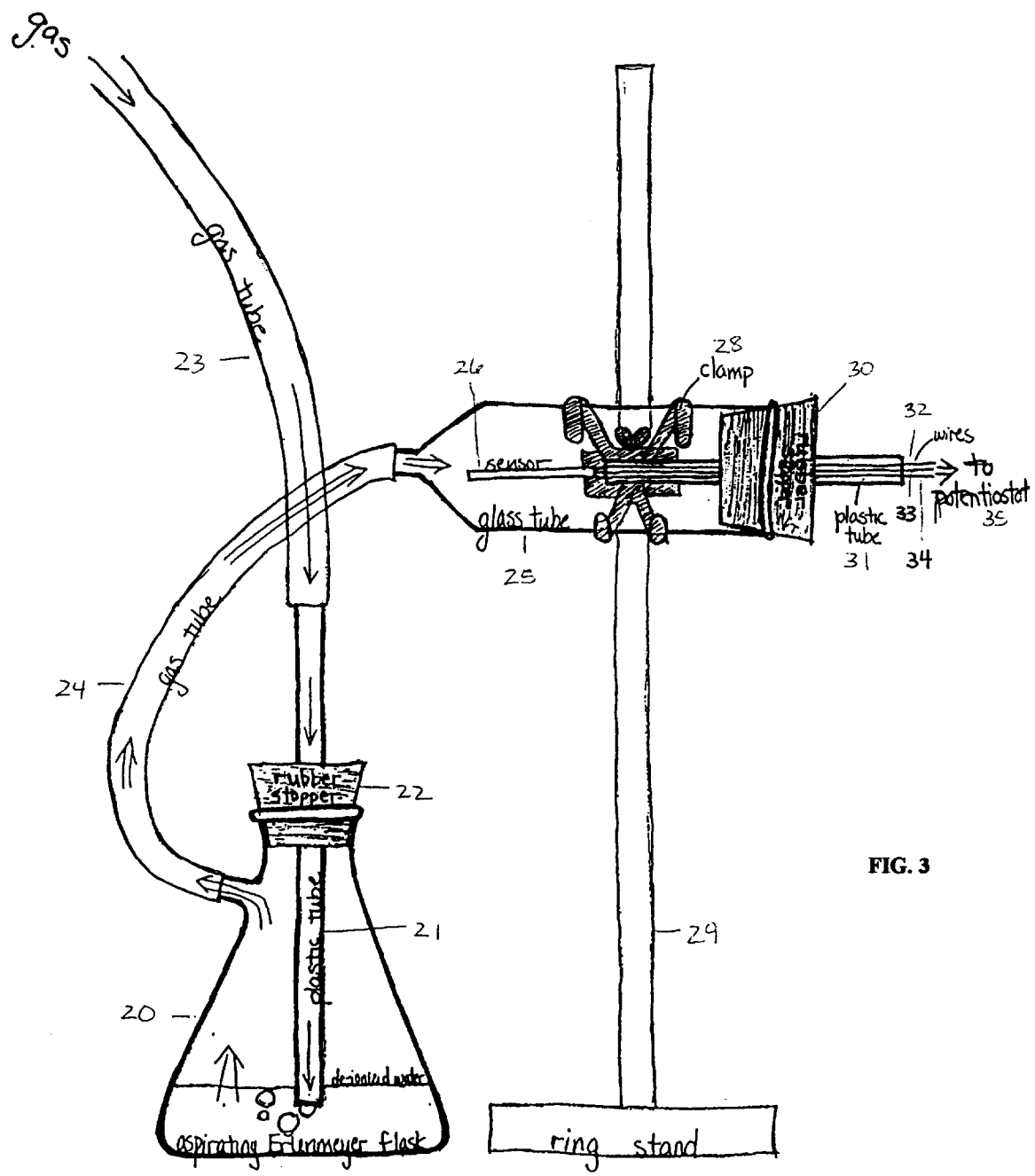
FIG. 3 is a schematic illustration of the device used for testing the sensors of examples nos. 1–11 and 14–15.
Figure 4:
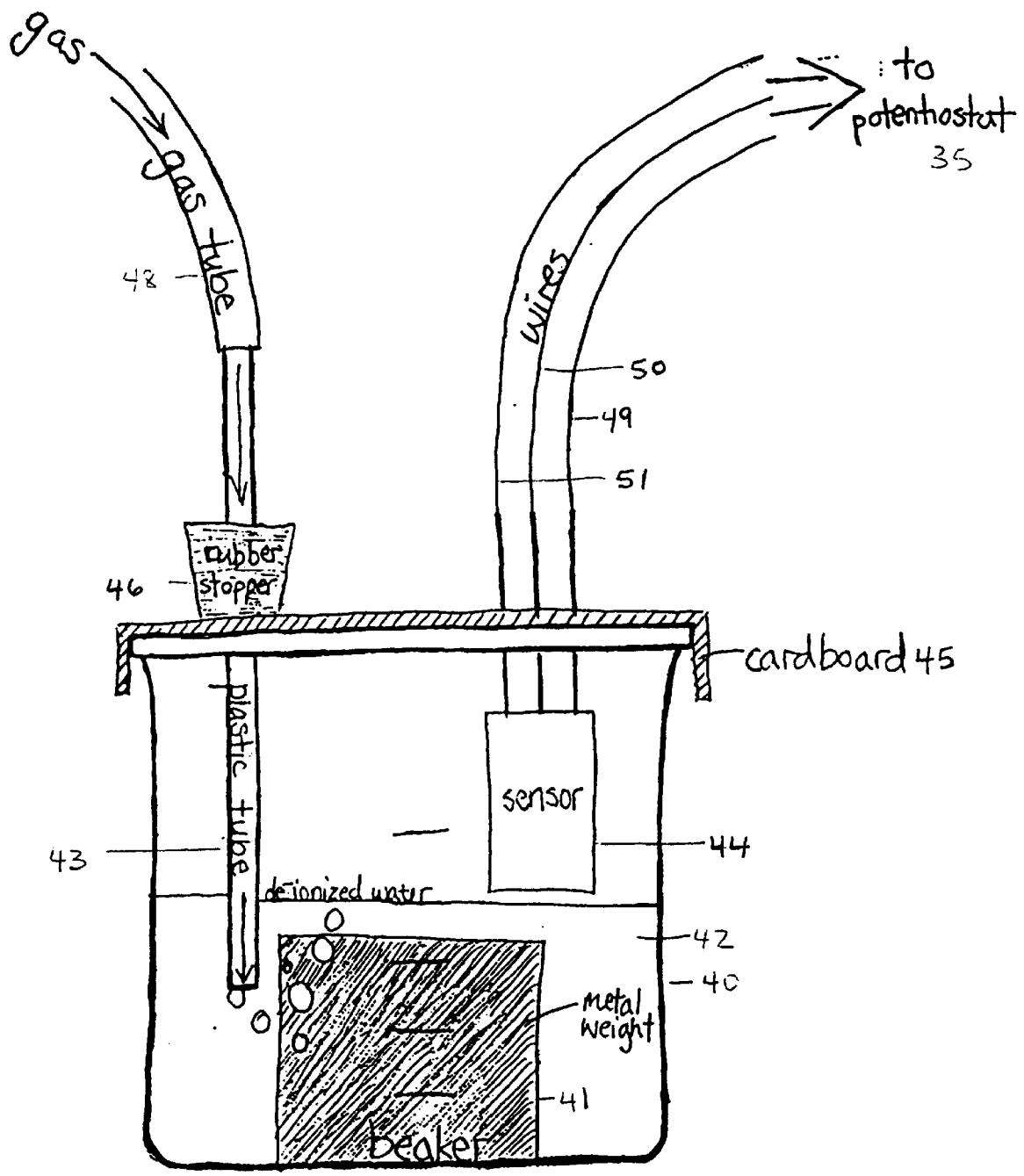
FIG. 4 is a schematic illustration of the device used for testing the sensors of examples nos. 12 and 13.

The 15 thick film electrochemical micro-sensors fabricated as described above were tested in one of the device shown in FIGS. 3 and 4. The setup in FIG. 3 was used to test the sensors of example nos. 1–11 and 14–15. The gas entered the device through a tube 23 which was connected to a plastic tube 21 that was fitted with a rubber stopper 22, and passed into an Erlenmeyer flask 20 containing deionized water. Another tube 24 transported the gas from the flask 20 to a glass tube 25, supported by a clamp 28 and a ring stand 29. Within the glass tube 25 was suspended the micro-sensor 26 to be tested. Attached to the micro-sensor device were three electrical wires 32, 33, 34 that extended out of the glass tube 25 through a rubber stopper 30 and were connected to a potentiostat 35.

The sensors of example nos. 12 and 13 were tested using the setup in FIG. 4. The gas entered through a tube 48 into a beaker 40, fitted with a cardboard covering 45, and containing deionized water. The tube 48 passed through a rubber stopper 46. The beaker 40 contained a metal weight 41. Suspended above the surface of the deionized water was the sensor to be tested 44. Connected to the micro-sensor device were three electrical wires 49, 50, 51, which passed through the covering 45 and were connected to a potentiostat 35.

Part II: Testing

1.) Wait 1 day after application of Nafion™ resin or membrane.
2.) Connect the gas tubes of the tanks of sulfur dioxide and air to the gas mixers.
3.) Connect another gas tube from the mixer to the plastic tube on the rubber stopper.
4.) Fill the aspirating Erlenmeyer flask with approximately 200 ml of de-ionized water, and plug the rubber stopper onto the top of the flask. (FIG. 3).

5.) Connect another tube to the opening on the side of the flask and attach the other end to the skinny end of the glass tube.
6.) Cut three approximately 125 cm wires of different colors and connect one to each of the circuit wires from the potentiostat, which is in turn connected to a computer with an interface.
7.) Extend the wires to the hold while taping the wires onto the floor.
8.) Initiate the computer.
9.) Open the CHI660A Chemistry Workstation computer program.
10.) Soak the electrodes of a micro-sensor in the sodium nitrate solution for 30 minutes.
11.) Place the wires on the micro-sensors through the plastic tube of another rubber stopper.
12.) Connect the wire of the counter electrode with the negative wire, the working electrode with the positive, and the reference electrode with the reference electrode.
13.) Make sure the three bare portions of the wires are not touching one another.
14.) Open the valves of the two gas tanks both to 30 psi.
15.) Turn on the gas mixer and adjust the mixing to 400 for air and 0 for sulfur dioxide gas and turn on outlet 1 for air gas (0% sulfur dioxide).
16.) Let the gas bubble through the water for 5 minutes to stabilize.
17.) While the gas is bubbling, set the print setup to landscape and set the program to the following requirements:
  a.) Initial Voltage to 0V
  b.) High Voltage to 1V
  c.) Low Voltage to –0.6V
  d.) Initial Direction to Negative
  e.) Scan Rate to 0.1 V/sec
  f) Segments to 3
  g.) Sample Interval to 0.001V
  h.) Quiet Time to 0 sec
  i.) and Sensitivity to 0.001 A/V.
18.) Click run experiment.
19.) Save the test run.
20.) Turn off outlet 1 and adjust the mixing air gas to 200 and sulfur dioxide gas to 200 before turning both 1 and 3 (1% sulfur dioxide).
21.) Let the gas mixture bubble through the water for 5 minutes while printing the graph of the test run with inverted x- and y-axes and copying the data for segment 2 at 0.4V, 0.5 V, 0.6V, 0.7V, and 0.8V. Also, during this time make sure the requirements from the above are set.
22.) Repeat steps 18–19.
23.) Repeat steps 20–22 with 400 for sulfur dioxide gas and 0 for air and only turning on outlet 3 (2% sulfur dioxide).
24.) Turn off the gas mixer and detach the mixers before removing them from the glass tube.
25.) Rinse the micro-sensor as well as the emptied aspirating Erlenmeyer flask with de-ionized water.
26.) Turn off the potentiostat and the valve of the two gas tanks.
27.) Open the Slide Write computer program.
28.) Insert the data with 0, 1, and 2 repeated 5 times in the x-column and the current values in micro-amperes for 0.4V in graph A, 0.5V in B, 0.6V in C, 0.7V in D, and 0.8V in E.
29.) Set the graph type to scatter, the graph fitting to linear, the legends to right, the x-axis to label and to from 0–2 with 2 divisions, and the y-axis to values appropriate for the obtained data.
30.) Click redraw chart.
31.) Click on statistics to determine the curve fitting coefficient, r.
32.) Label each graph by its voltage and curve fitting coefficient in the legends.
33.) Select save and print.
34.) Repeat steps 8–33 for the other sensors except 12 and 13, which will not fit in the glass tube.
35.) Repeat steps 8–33 for sensors 12 and 13, but use the setup of FIG. 4:
  a.) Place a beaker in the hold.
  b.) Place the metal weight as the bottom and fill the beaker with enough de-ionized water to cover the metal block.
  c.) Cut a cardboard cover for the beaker with a hole for inserting the plastic tube from the rubber stopper.
  d.) Place the cardboard cover over the beaker and insert the plastic tube from the rubber stopper connected to the gas tubes.
  e.) Dangle the sensors in the beaker without touching the water.

Figure 5:
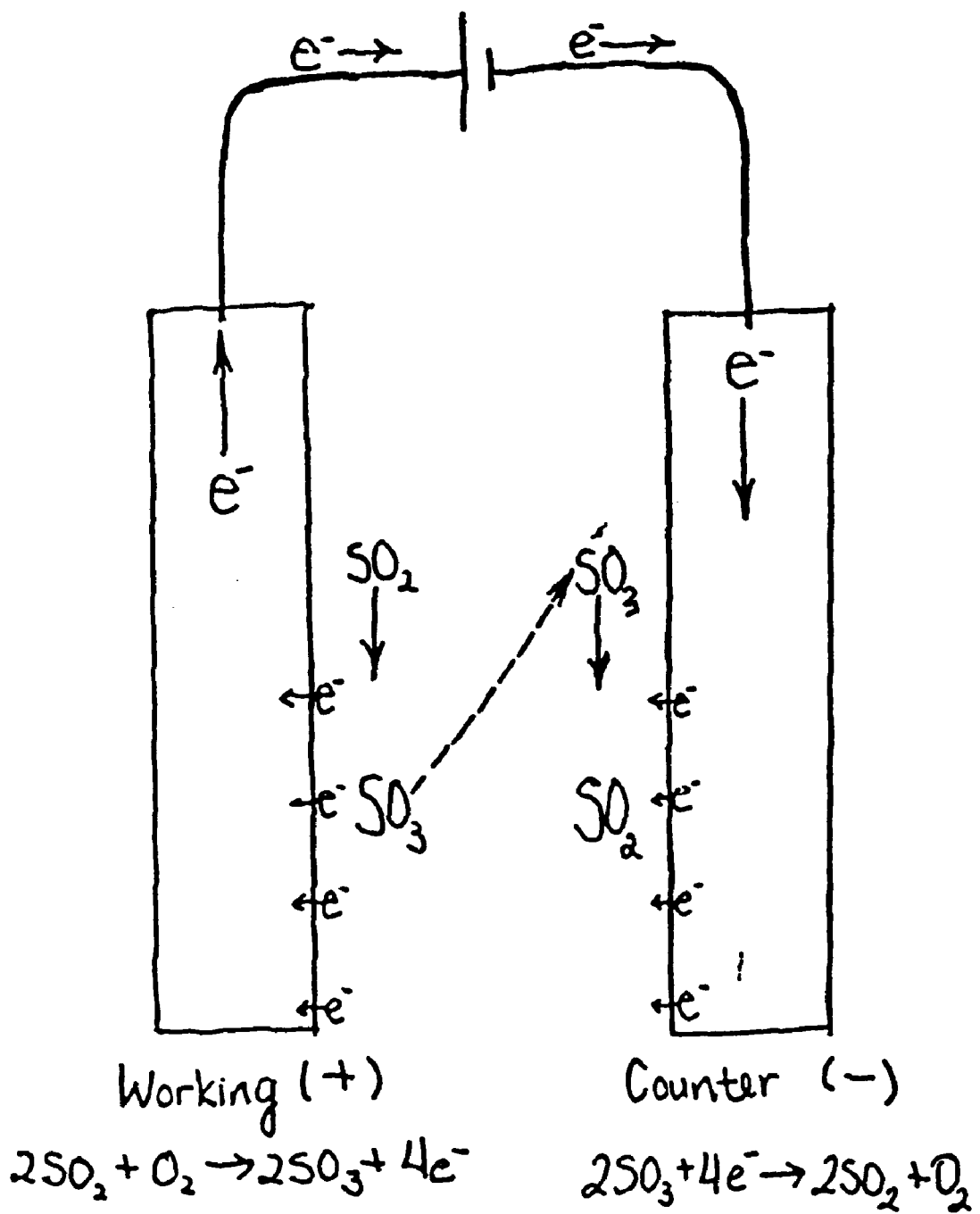
FIG. 5 is a schematic illustration of the chemical reactions which occur at the electrodes.

The thick film sensors of the present invention operate based on oxidation and reduction reactions. The Gibbs free energy calculated from the oxidation-reduction (or redox) reaction of the substance being detected at the working electrode was used to determine the applied potential voltage needed to enable the specific redox reaction to occur. The range from –0.6V to 1V was chosen because that was the range for which a little oxidation occurred as well as little reduction Representative chemical equations are as follows:

When the voltages are applied, the way that the electrodes operate is shown in the diagram of FIG. 5. As the sulfur dioxide contacts the working electrode, an electrochemical reaction occurs, resulting in higher current. The counter electrode is driven by the potentiostat to maintain the potential difference between the working electrode and the reference electrode. A measurement of current at the working electrode is related to the concentration of the sulfur dioxide. The sensor can therefore be calibrated at any given operating temperature by known techniques. Test results for Examples 1–15 are shown in the graphs of FIGS. 6A through 20B.

Three main types of three-electrode arrangements were prepared and tested in the initial phase. Five of the fifteen examples employ a rectangular electrodes arrangement. These include sensor example numbers 1, 5, 9, 10, and 13. Another type of arrangement was prepared, in which reference electrode is a circle. Seven of the fifteen examples (3, 4, 8, 11, 12, 14, and 15) have this configuration, but these can be divided into two branches. Four of the seven examples, including numbers 3, 11, 12, and 14, have the counter electrodes and the working electrode almost completely encircling the reference electrode, while the other three have the counter electrode and working electrode both being half circles. The last type of configuration utilizes an elliptical reference electrode with a working electrode and a counter electrode that are almost full ellipses themselves. Sensor designs with this configuration include examples 2, 6, and 7. All of these various configurations were tested to determine whether the shape and arrangement of the electrodes would have an effect on how the sensors operate to detect sulfur dioxide.

Within each type of electrode arrangement, the sizes of the electrodes as well as of the sensors themselves vary from sensor design to sensor design. This made it possible to study the effect of the size of the electrodes on sensitivity, as well as on the efficiency of the sensors.

Another variable investigated was the distance of the gaps between the working and counter electrodes. Within each type of configuration, the gaps between the working and counter electrodes also varied due to changes in sizes. By varying the gap distances, the effect that these gaps have on the sensors' sensitivity and efficiency was observed. It was found that optimum sensitivity and efficiency was observed when the gap size was less than or equal to about 0.2 inches, and preferably less than or equal to about 0.1 inches. More preferred is a gap size of about 0.04 to about 0.05 inches, as exemplified in the sensors of examples 3 and 7. Care should be taken, however, that the inks do not bleed into each other during fabrication, as this will cause a short circuit in operation.

Although the designs of the micro-sensors were created with various differences in the size and the shape of the electrodes, in order to compare the effect that these alterations have on the accuracy of the sensors, the materials used to form the electrodes, platinum and silver-silver-chloride, were not altered. Based on their individual characteristics, it was considered that these two materials were the preferred choices. Platinum is an inert conductor as well as a noble transition metal, which does not react readily with sulfur dioxide, and it is also highly reversible. On the other hand, silver/silver-chloride is also reversible with a low EMF, making it an optimum choice for the reference electrode. Although hydrogen is also a good choice for the reference electrode, it would be harder and more expensive to retain a gaseous hydrogen electrode, especially at high temperatures. Therefore, the materials of platinum for the working electrode and counter electrodes, and of silver-silver-chloride for the reference electrode are preferred.

The first of the configurations discussed above was the rectangular configuration that was used for the sensors of examples 1, 5, 9, 10, and 13 (which will be discussed later). In the rectangular configuration, the working electrode and the counter electrode are placed with the reference electrode interposed between them. Because of this, the gap between the working and counter electrodes is approximately 0.2 inches or more, greater than that of other configurations, and there are no regions where the working and counter electrodes are adjacent to one another. This increased gap size, as well as the lack of adjacency between the working and counter electrodes, leads to an increased resistance when the electrons are transferred from the counter to the working electrode. The increased resistance, in turn, causes the sensors of this configuration to have a lower current output or a lower sensitivity. This can be seen from the graphs of the test runs for these five sensors' current output, which are all less than 50 $\mu$A, as shown in FIGS. 6B, 10B, 14B, 15B, and 18B.

Figure 6A:
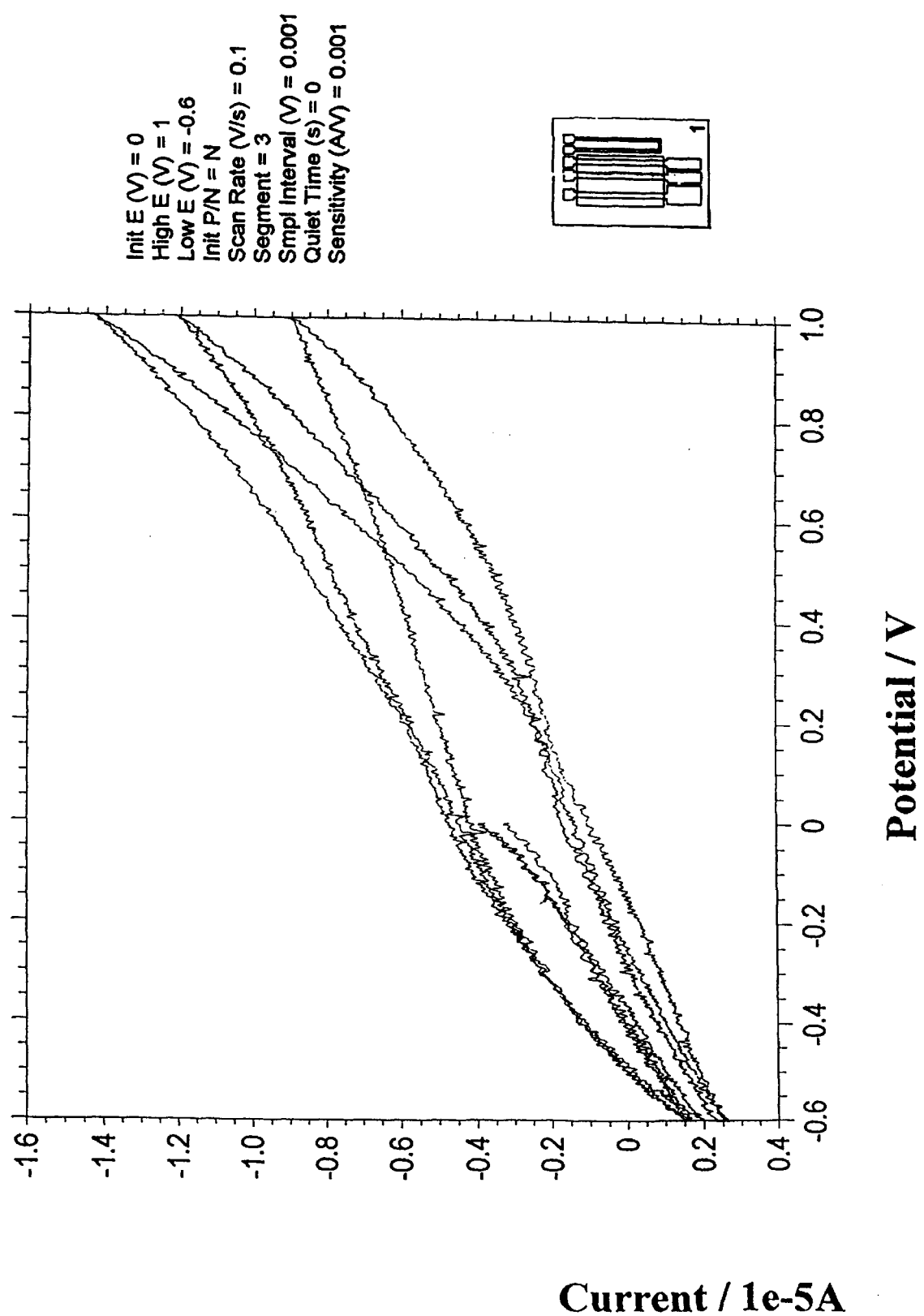
FIG. 6A is a graphical representation of the current output for the sensor of example no. 1 over a range of voltages from −0.6V to 1V.
Figure 6B:
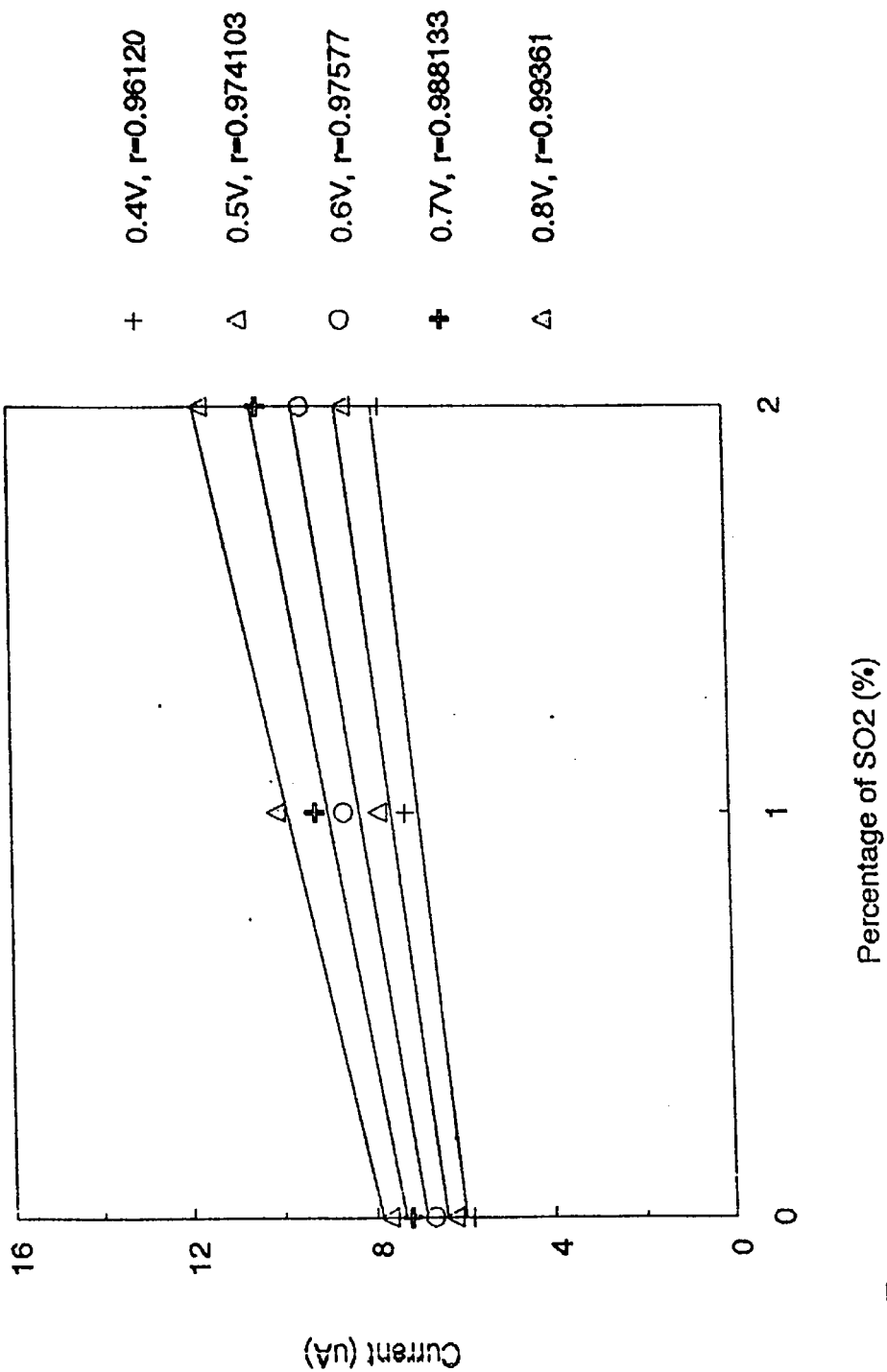
FIG. 6B is a graphical representation of the current output for the sensor of example no. 1 in relation to $SO_2$ concentrations from 0 to 2%.
Figure 7A:
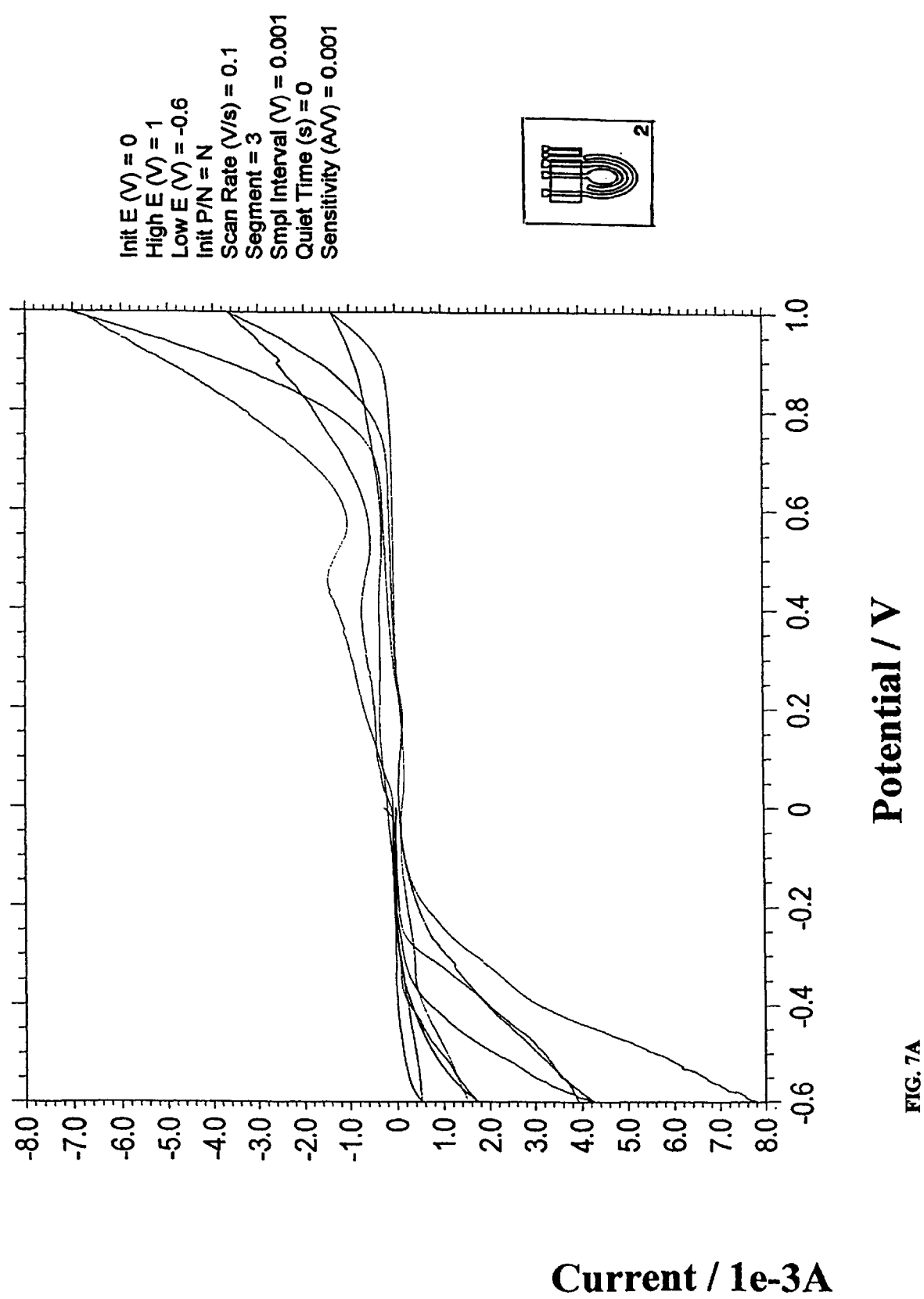
FIG. 7A is a graphical representation of the current output for the sensor of example no. 2 over a range of voltages from −0.6V to 1V.
Figure 7B:
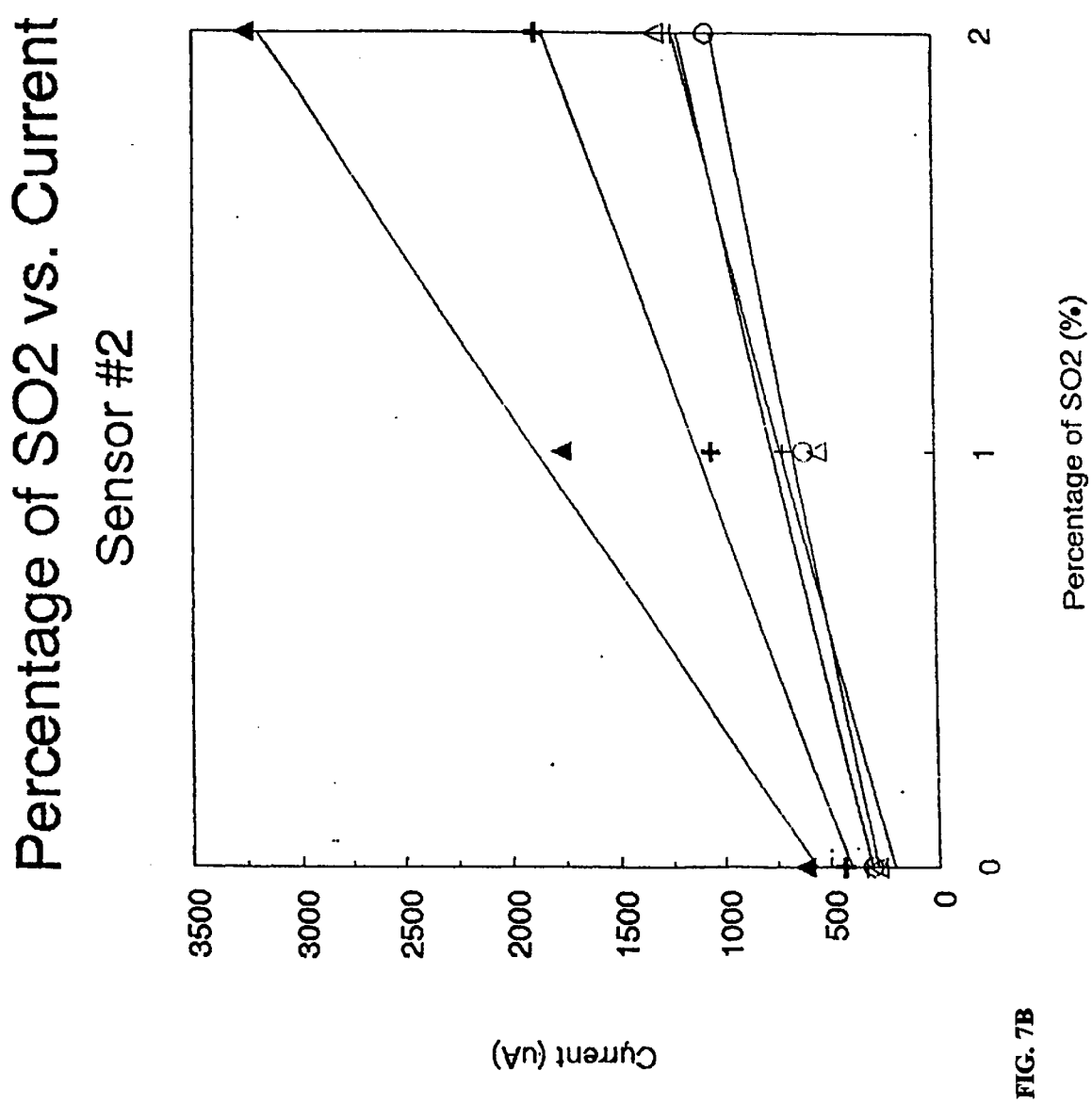
FIG. 7B is a graphical representation of the current output for the sensor of example no. 2 in relation to $SO_2$ concentrations from 0 to 2%.
Figure 8A:
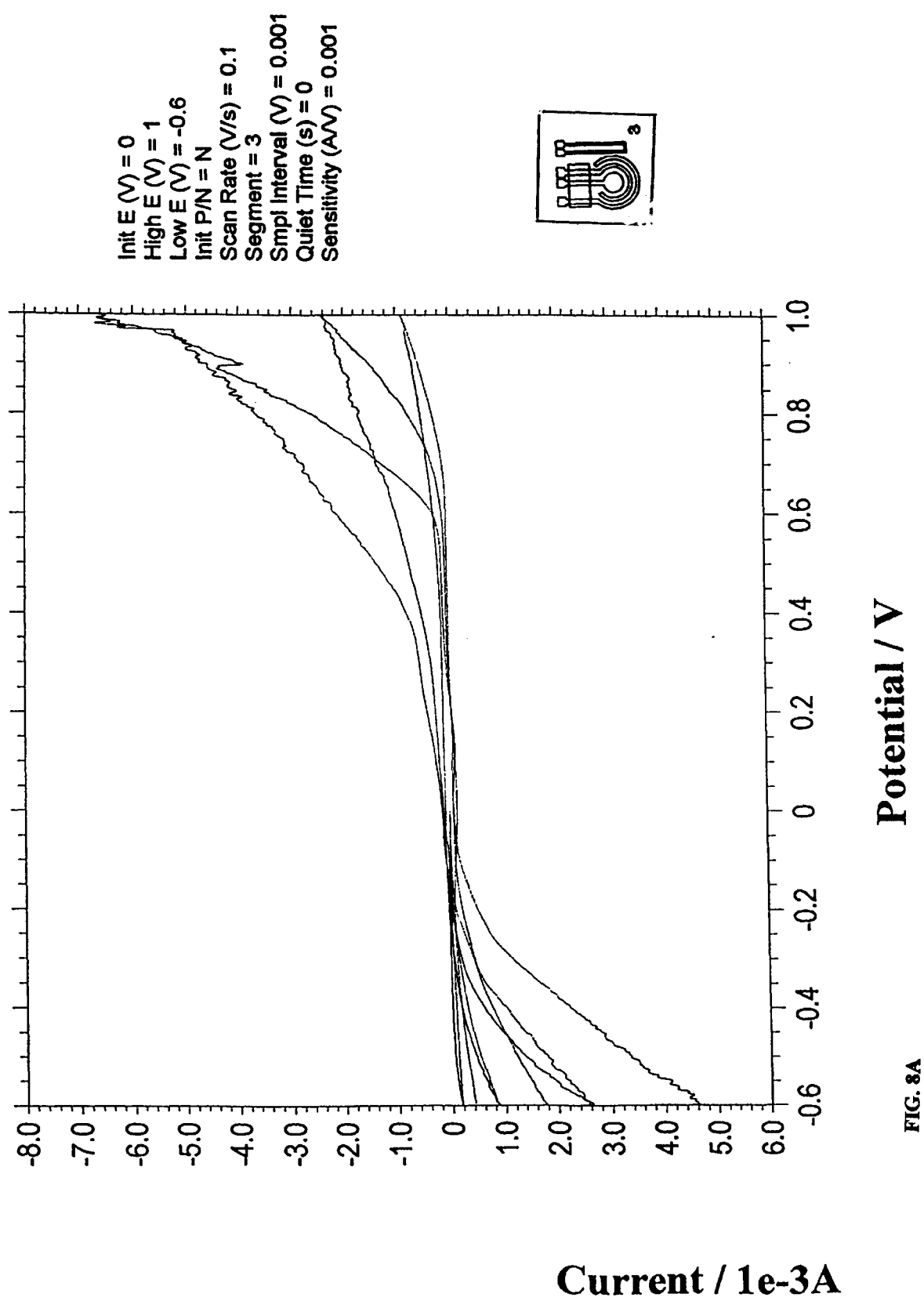
FIG. 8A is a graphical representation of the current output for the sensor of example no. 3 over a range of voltages from −0.6V to 1V.
Figure 8B:
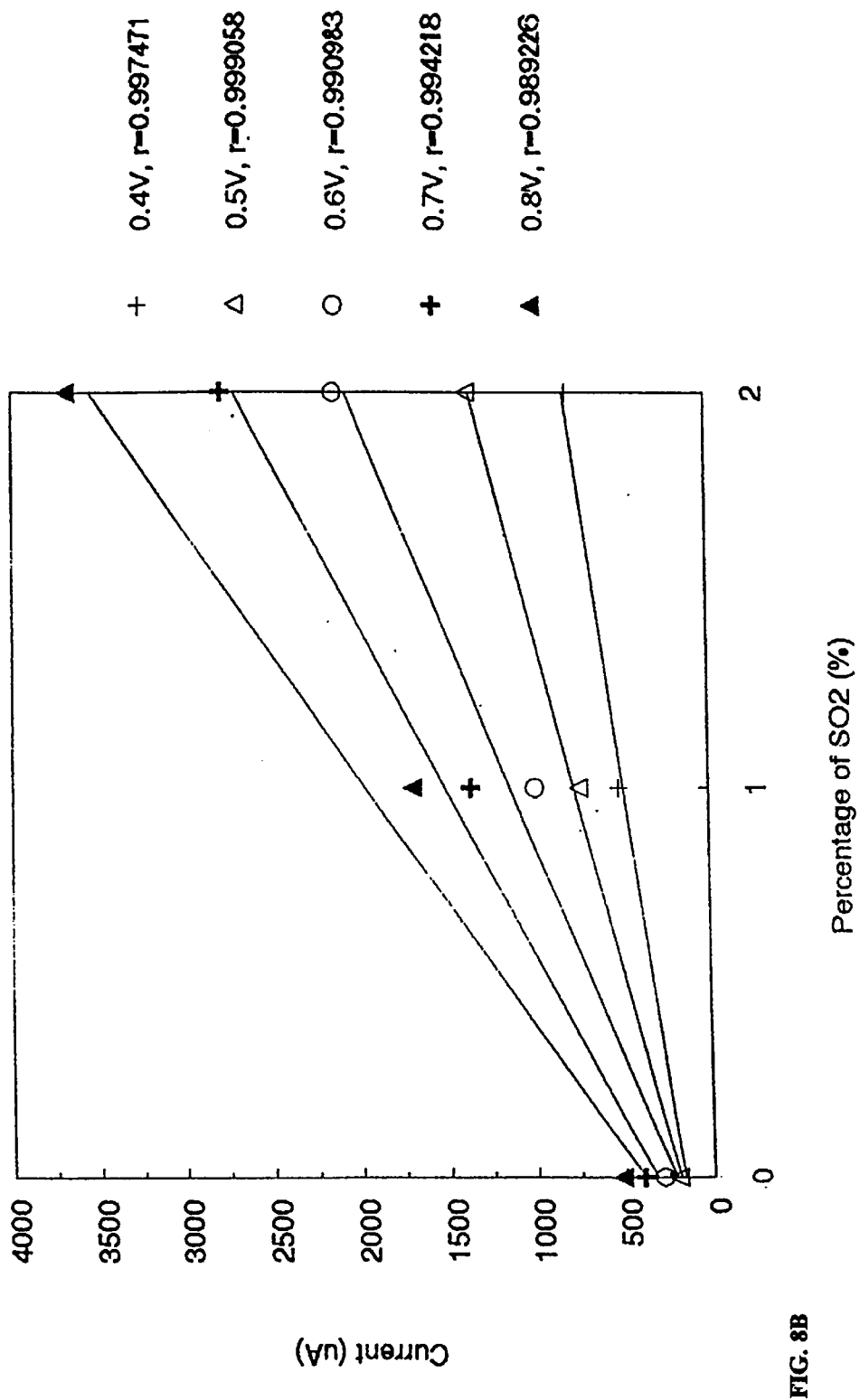
FIG. 8B is a graphical representation of the current output for the sensor of example no. 3 in relation to $SO_2$ concentrations from 0 to 2%.
Figure 9A:
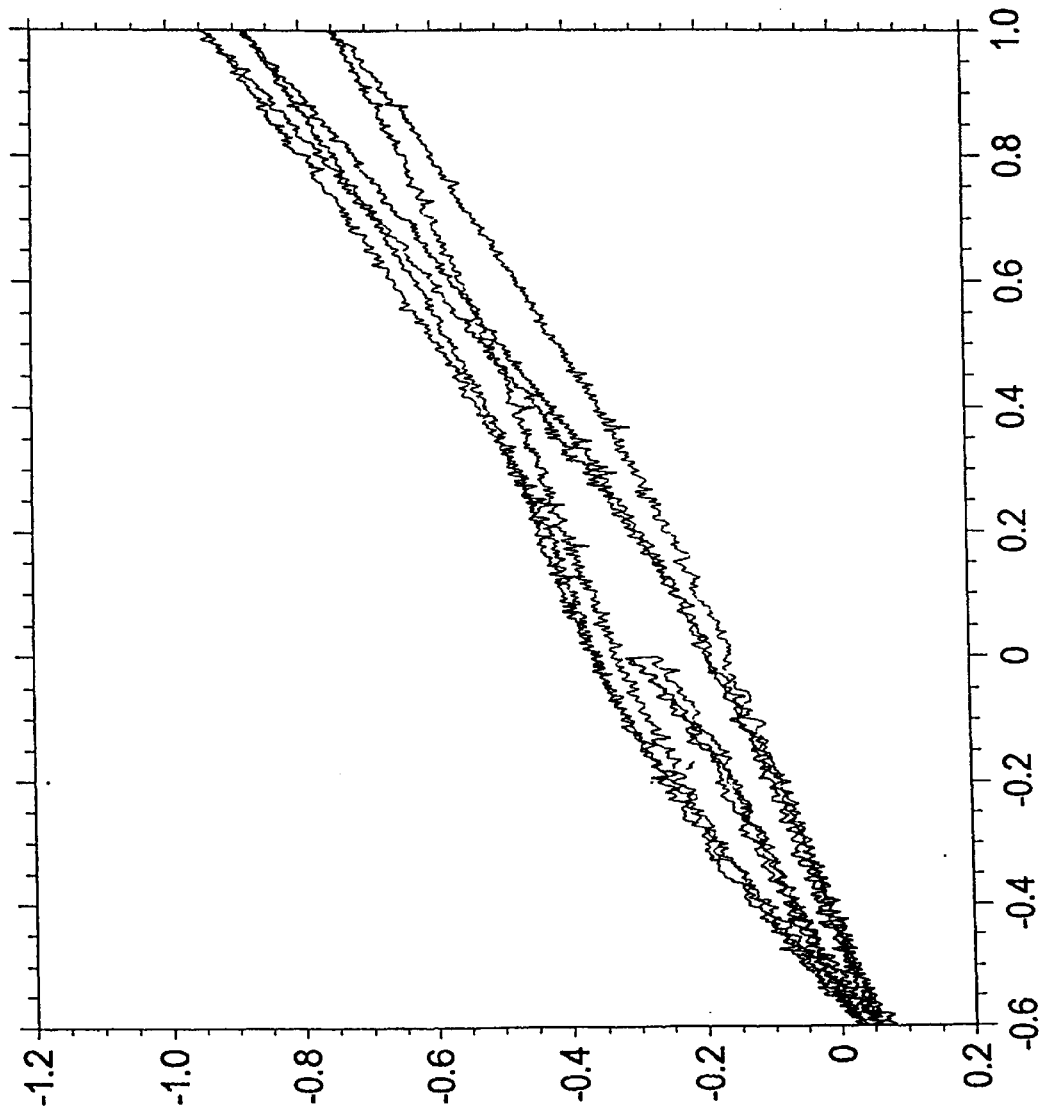
FIG. 9A is a graphical representation of the current output for the sensor of example no. 4 over a range of voltages from −0.6V to 1V.
Figure 9B:
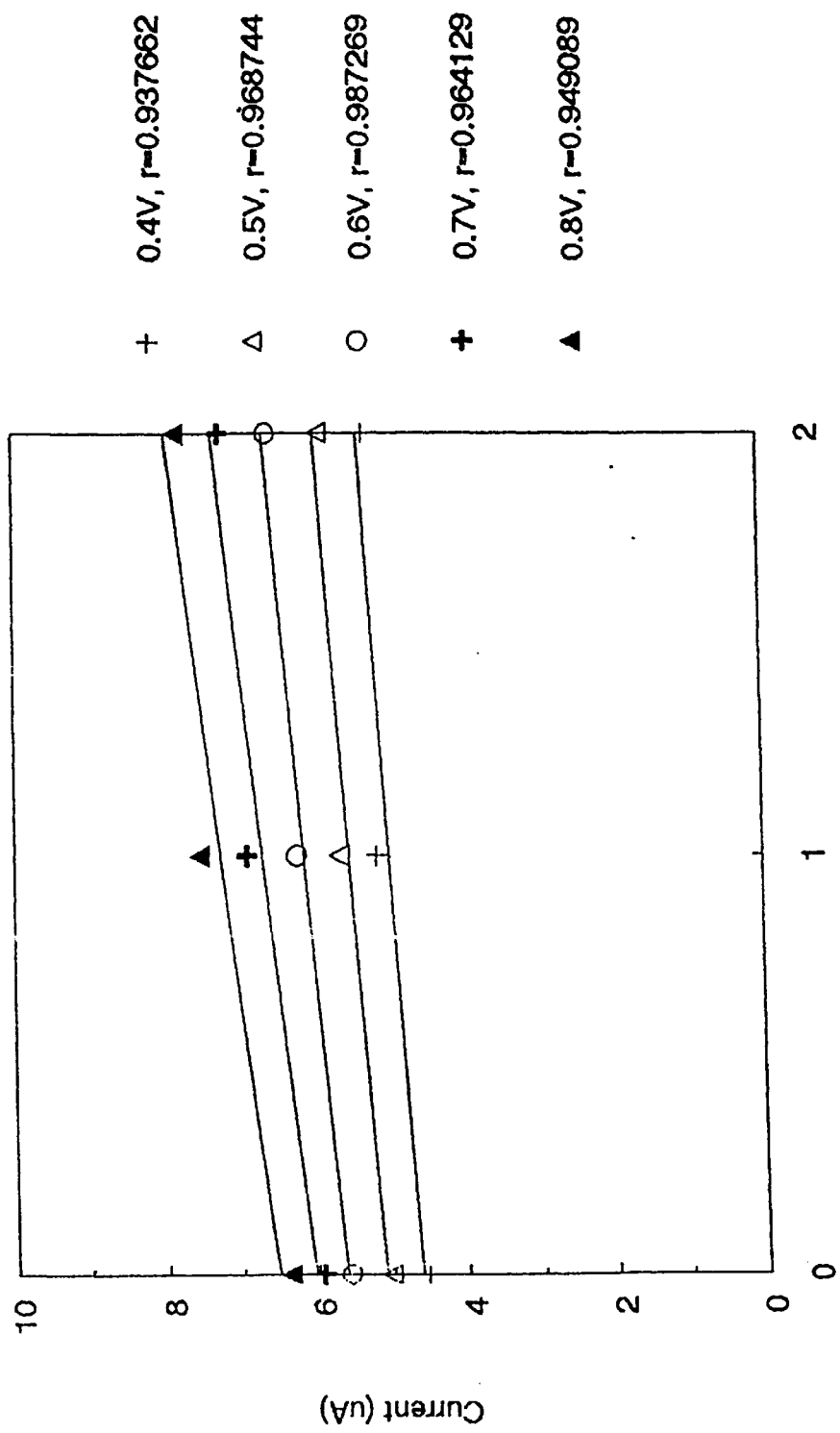
FIG. 9B is a graphical representation of the current output for the sensor of example no. 4 in relation to $SO_2$ concentrations from 0 to 2%.
Figure 10A:
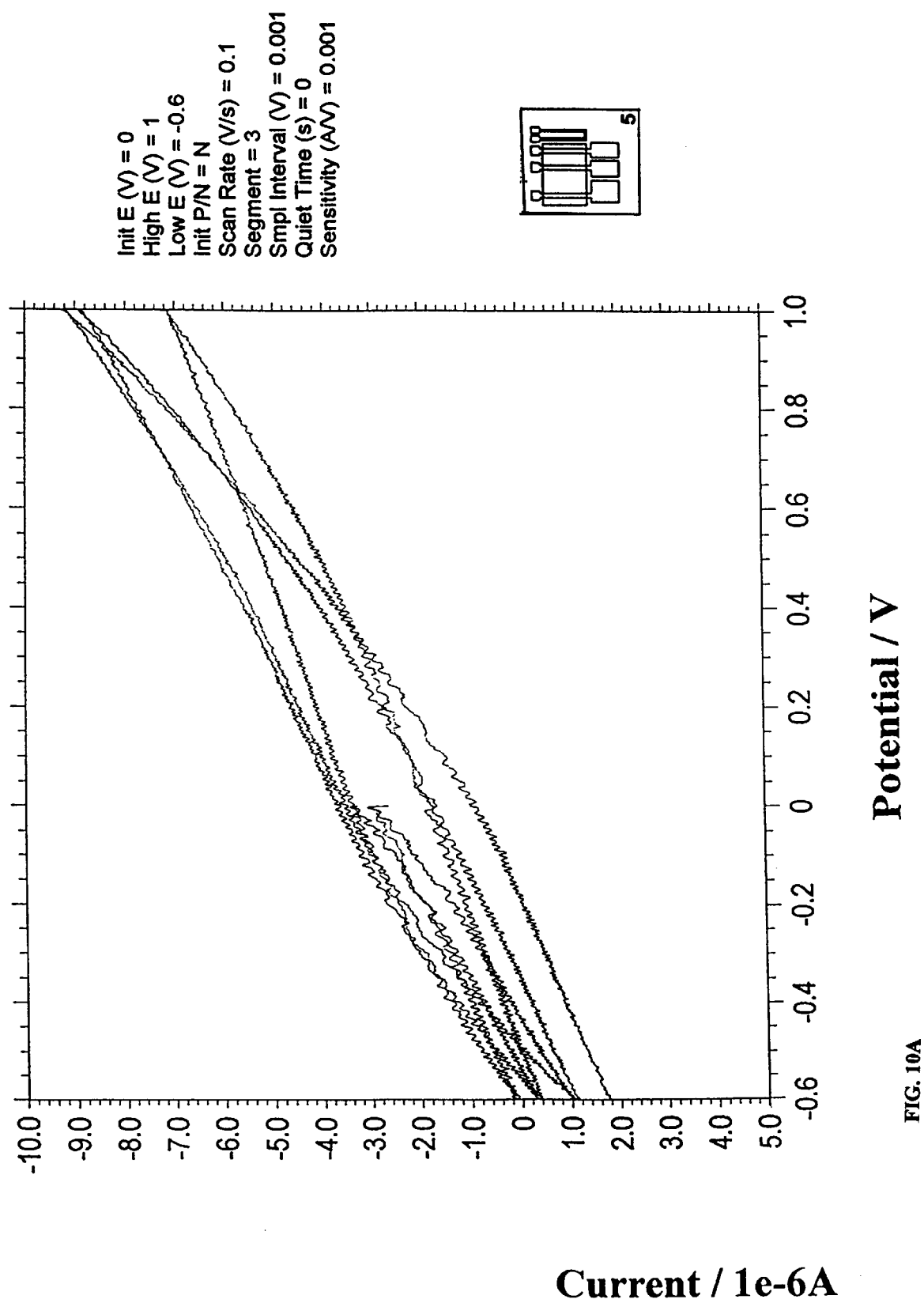
FIG. 10A is a graphical representation of the current output for the sensor of example no. 5 over a range of voltages from −0.6V to 1V.
Figure 10B:
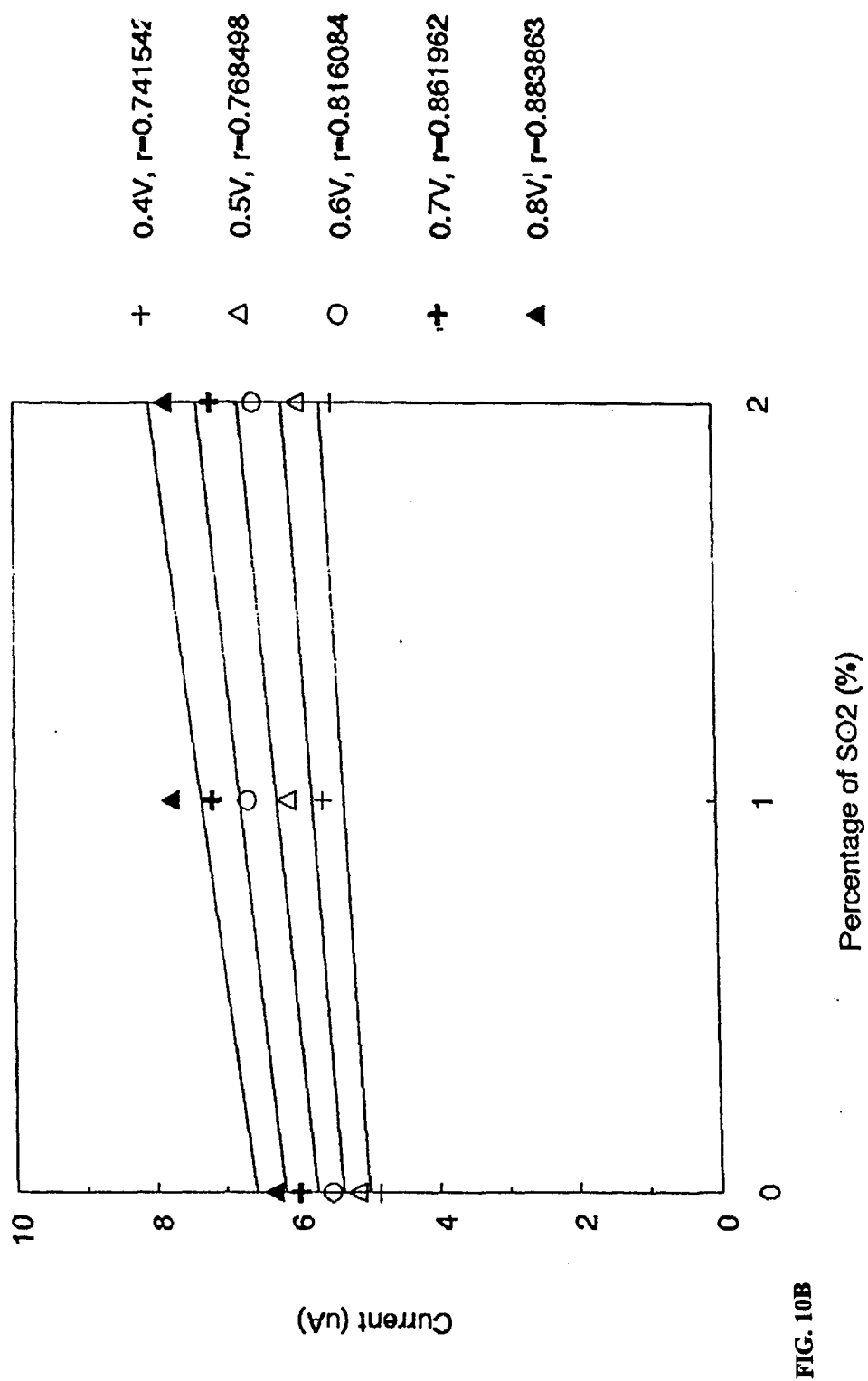
FIG. 10B is a graphical representation of the current output for the sensor of example no. 5 in relation to $SO_2$ concentrations from 0 to 2%.
Figure 11A:
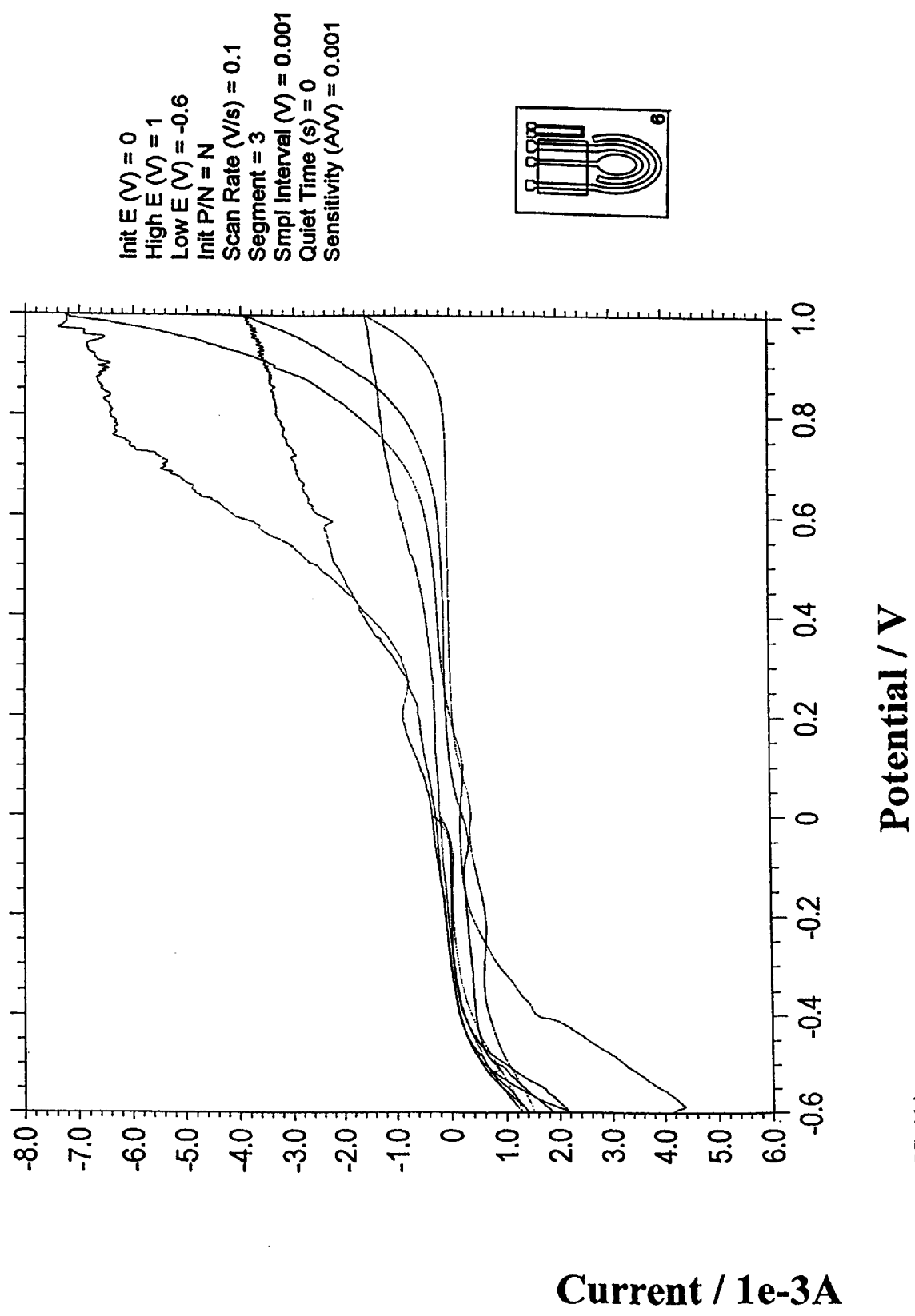
FIG. 11A is a graphical representation of the current output for the sensor of example no. 6 over a range of voltages from −0.6V to 1V.
Figure 11B:
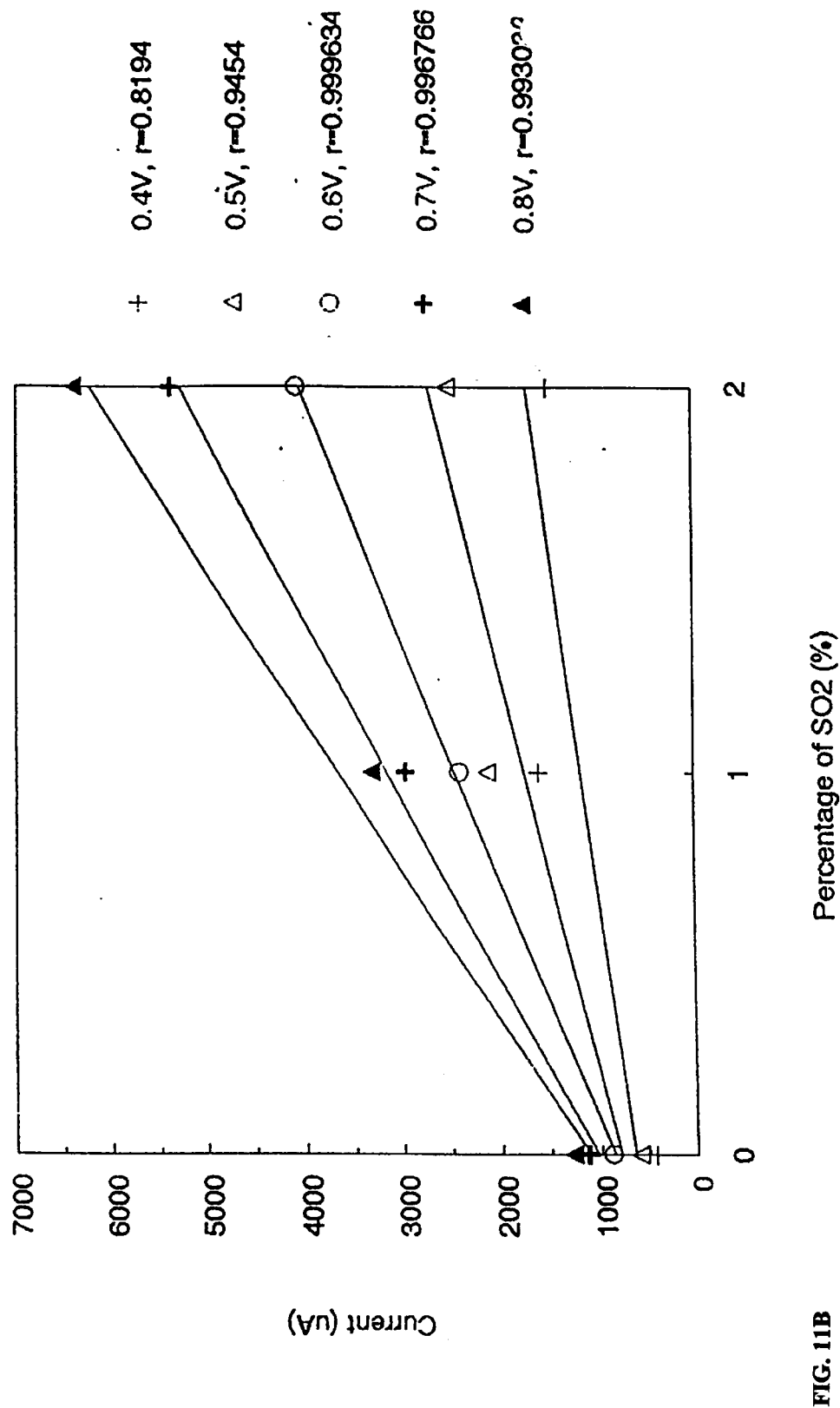
FIG. 11B is a graphical representation of the current output for the sensor of example no. 6 in relation to $SO_2$ concentrations from 0 to 2%.
Figure 12A:
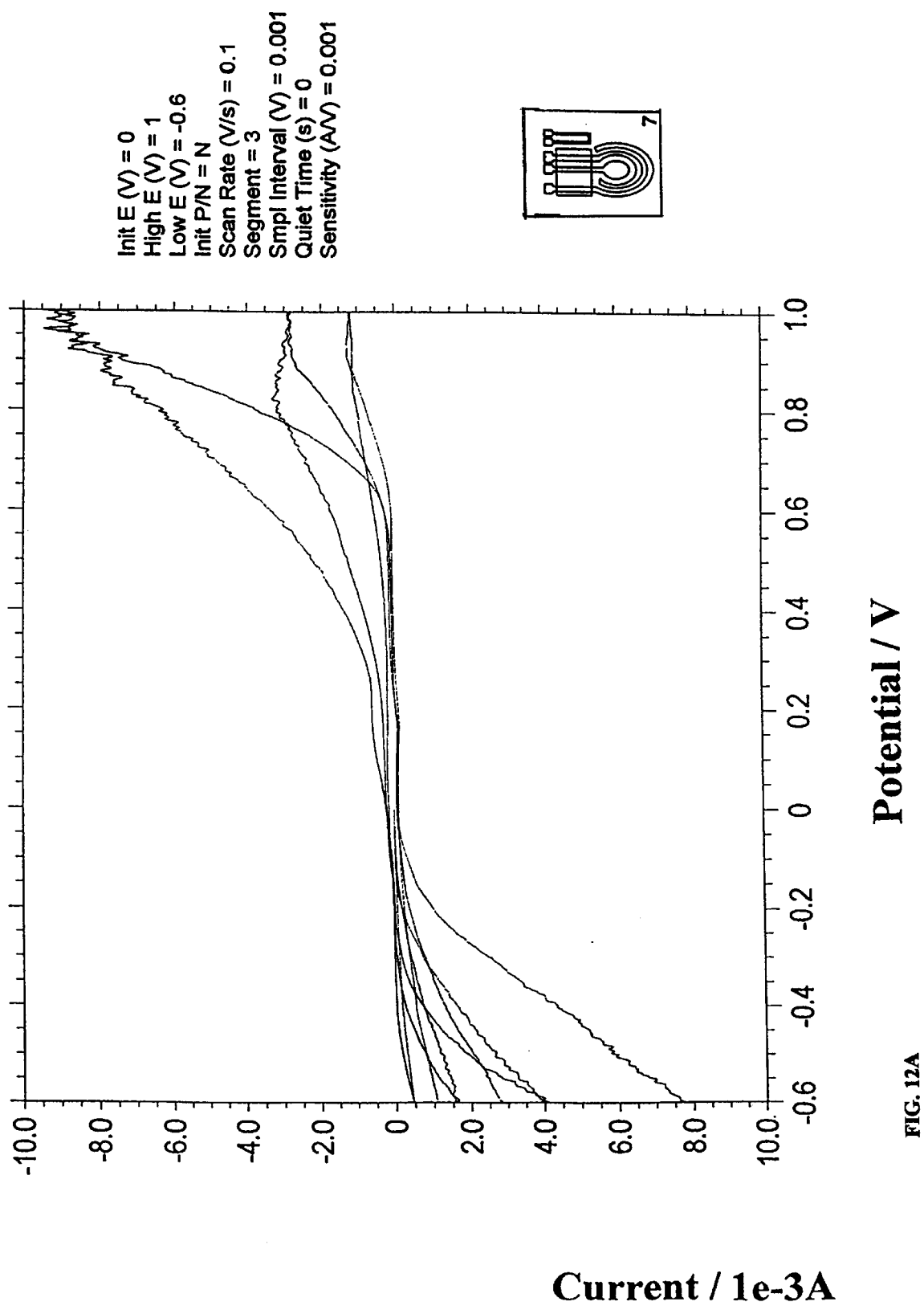
FIG. 12A is a graphical representation of the current output for the sensor of example no. 7 over a range of voltages from −0.6V to 1V.
Figure 12B:
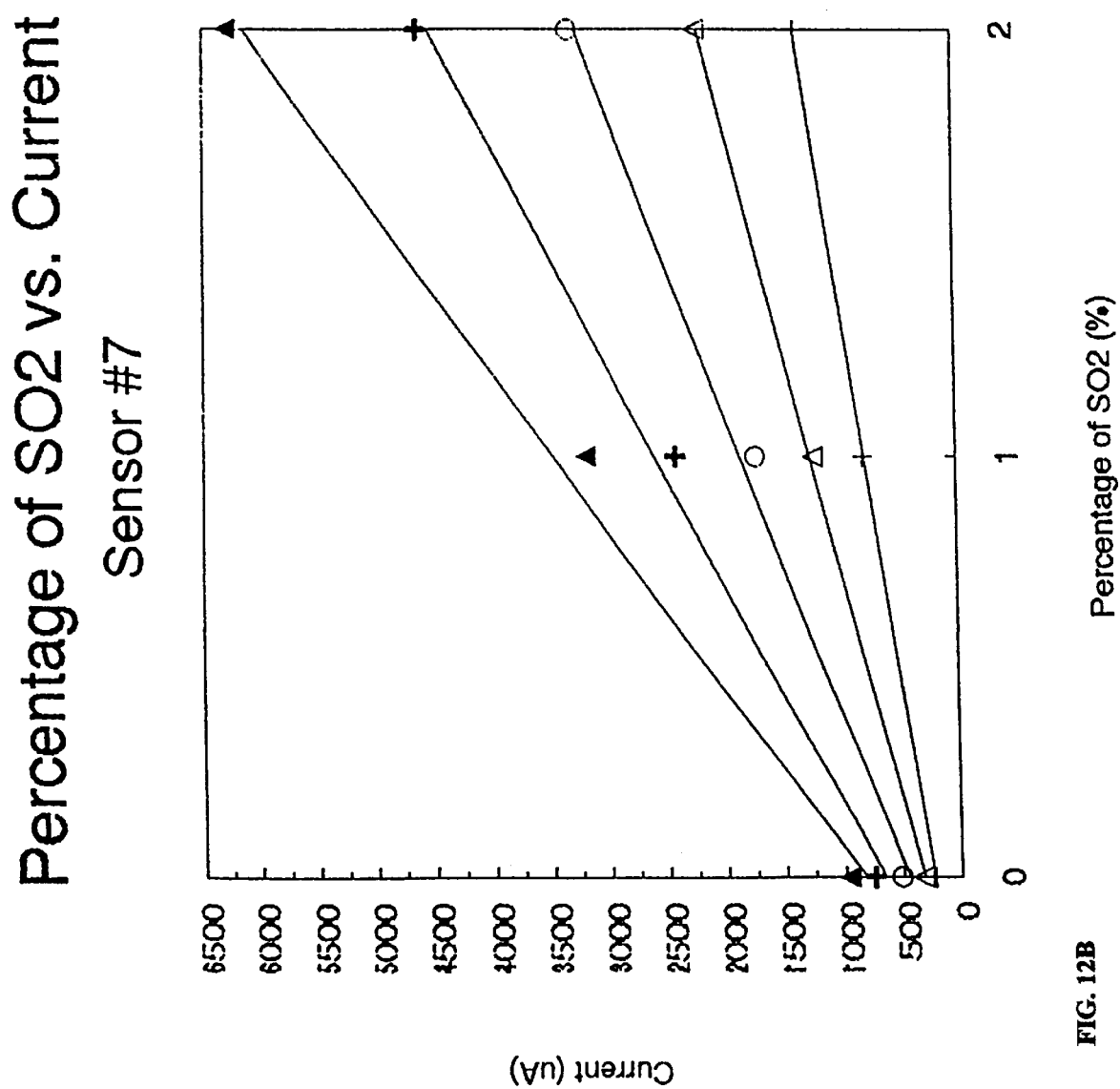
FIG. 12B is a graphical representation of the current output for the sensor of example no. 7 in relation to $SO_2$ concentrations from 0 to 2%.
Figure 13A:
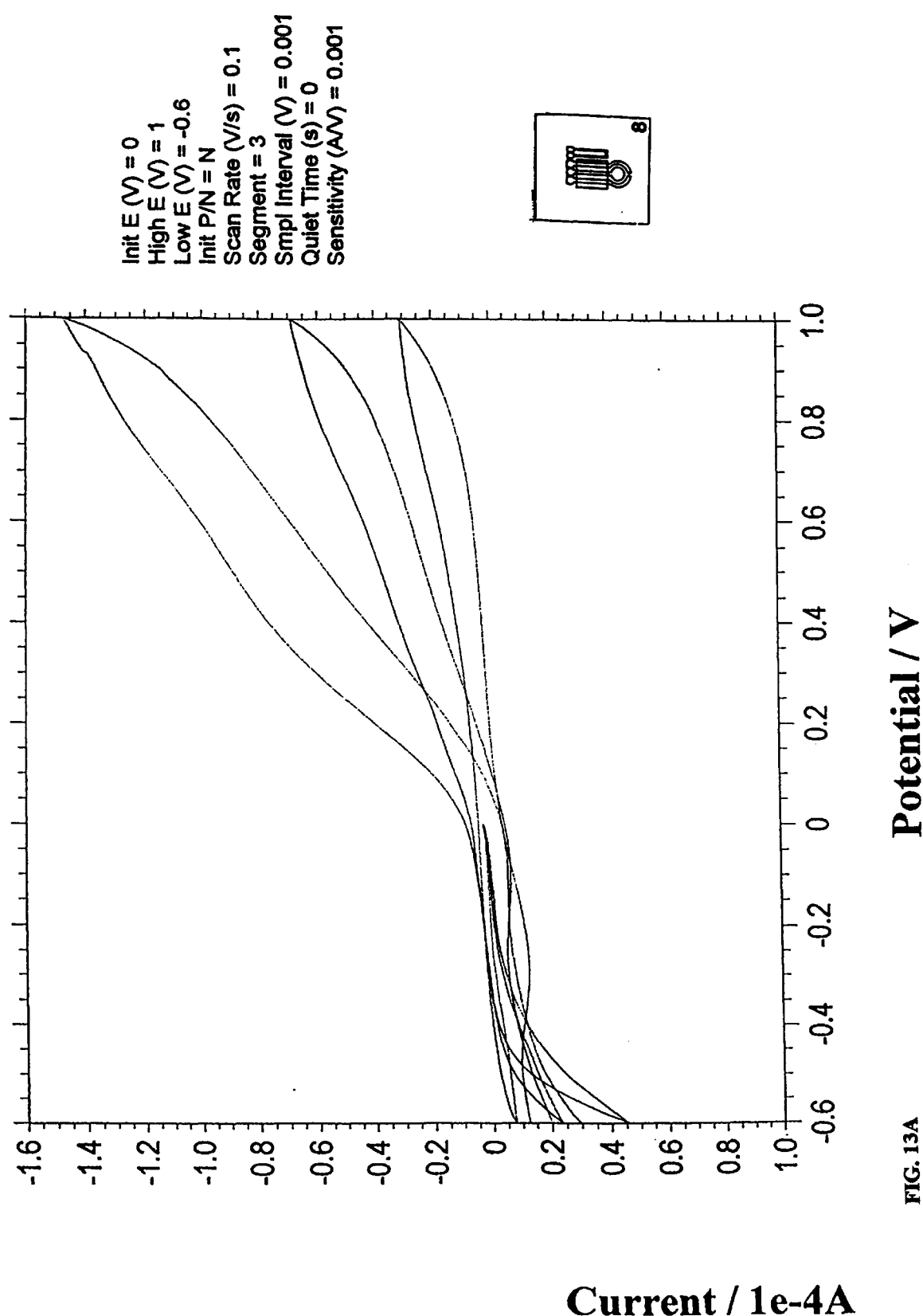
FIG. 13A is a graphical representation of the current output for the sensor of example no. 8 over a range of voltages from −0.6V to 1V.
Figure 13B:
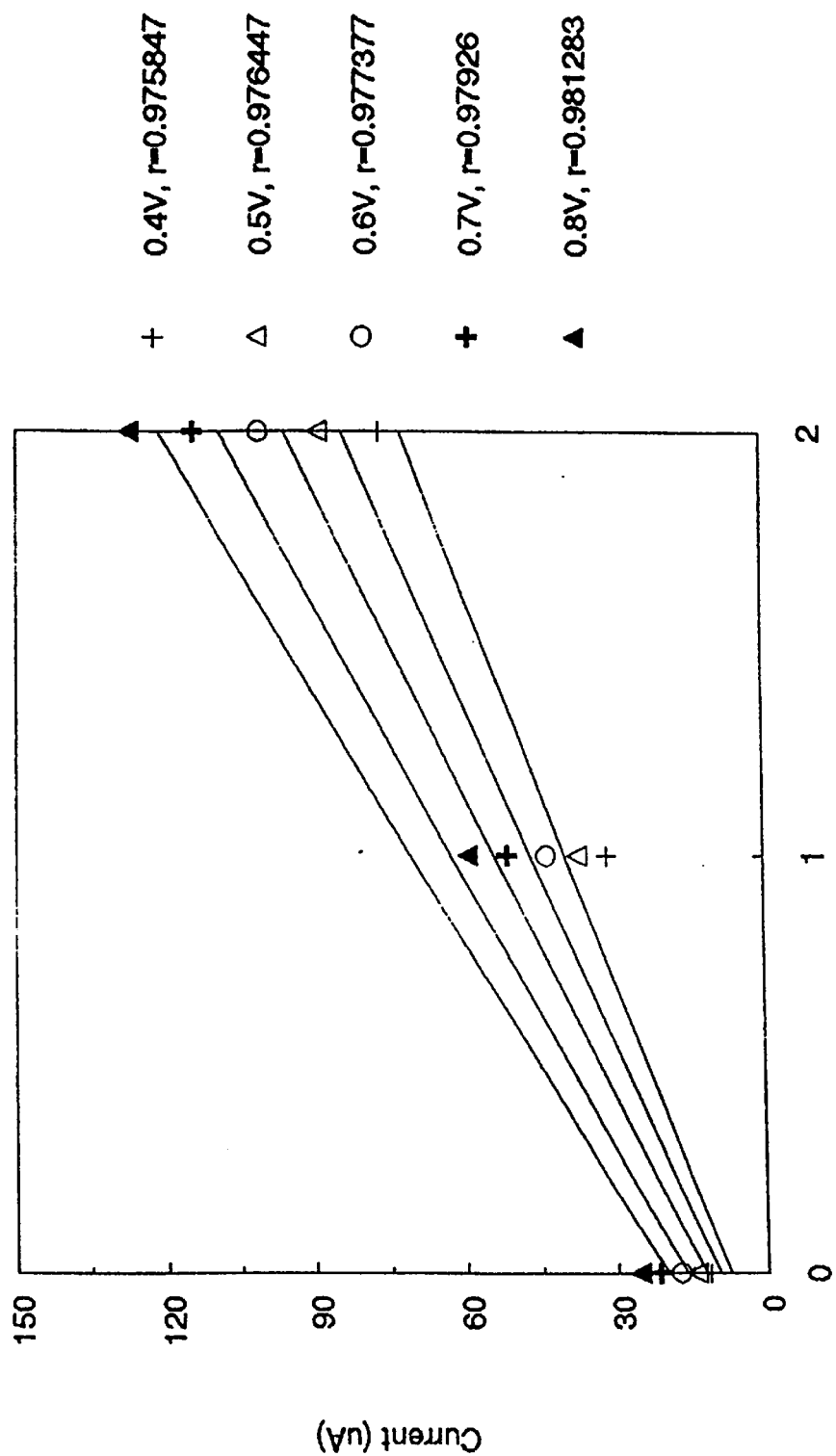
FIG. 13B is a graphical representation of the current output for the sensor of example no. 8 in relation to $SO_2$ concentrations from 0 to 2%.
Figure 14A:
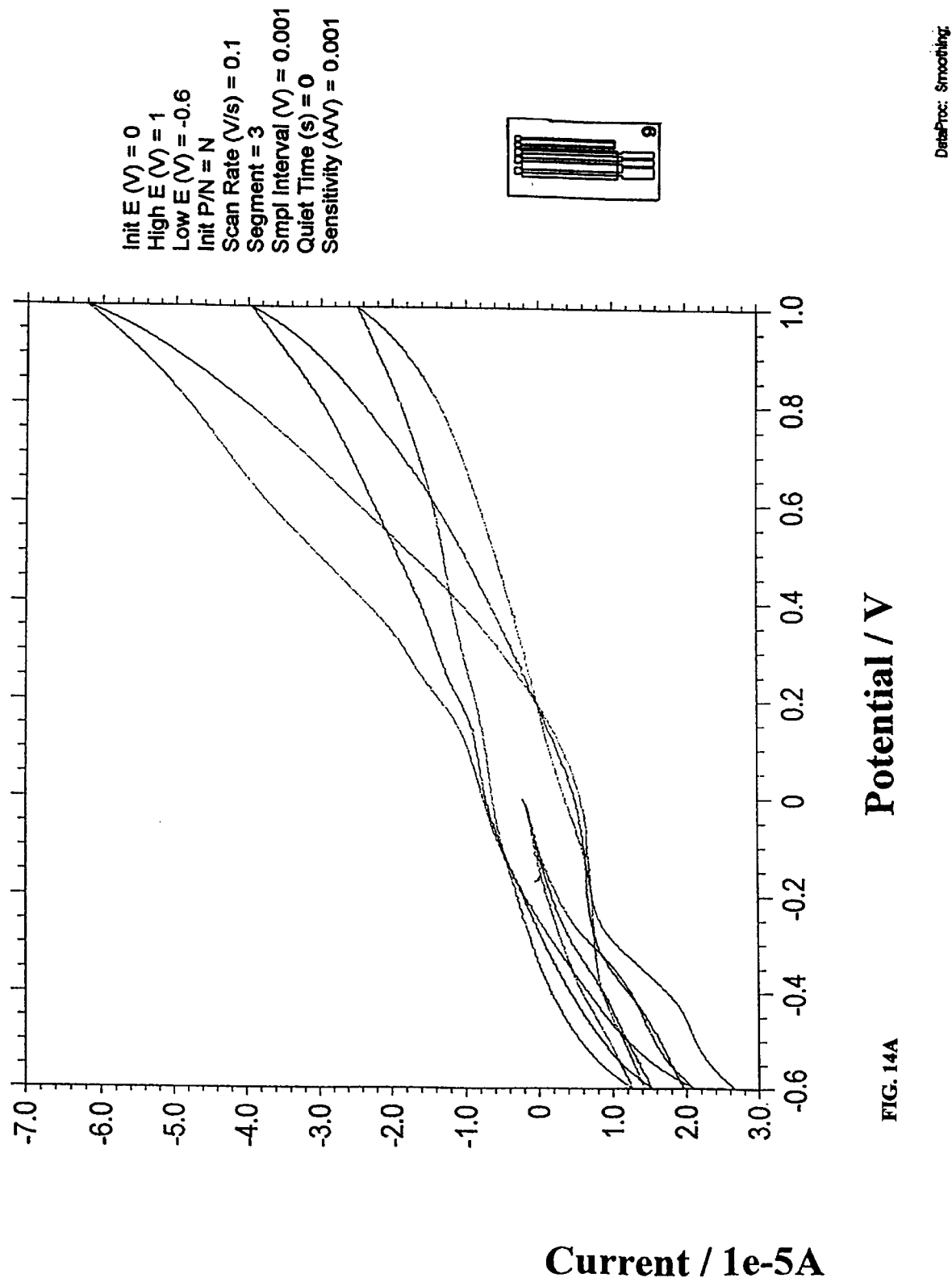
FIG. 14A is a graphical representation of the current output for the sensor of example no. 9 over a range of voltages from −0.6V to 1V.
Figure 14B:
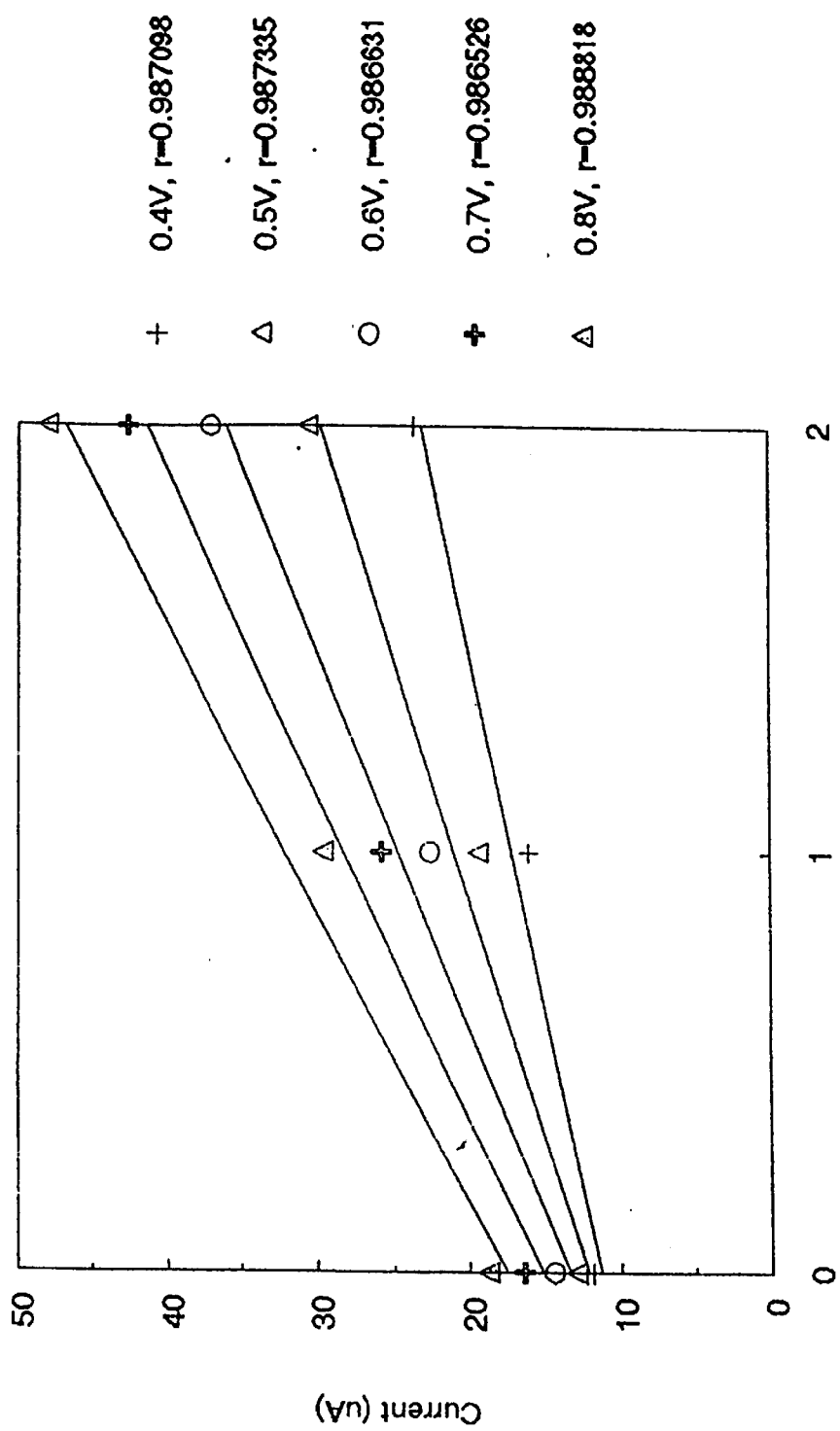
FIG. 14B is a graphical representation of the current output for the sensor of example no. 9 in relation to $SO_2$ concentrations from 0 to 2%.
Figure 15A:
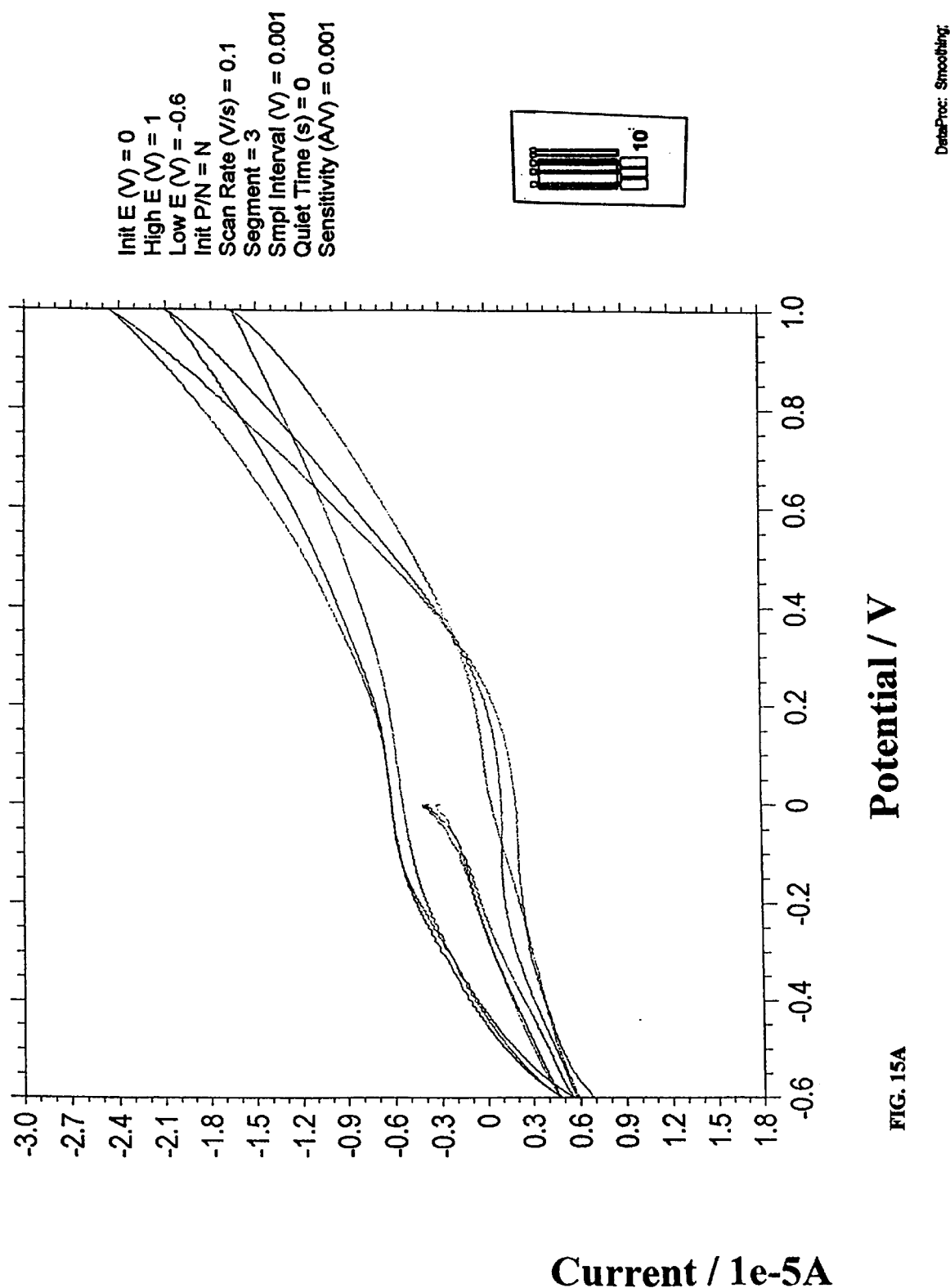
FIG. 15A is a graphical representation of the current output for the sensor of example no. 10 over a range of voltages from −0.6V to 1V.
Figure 15B:
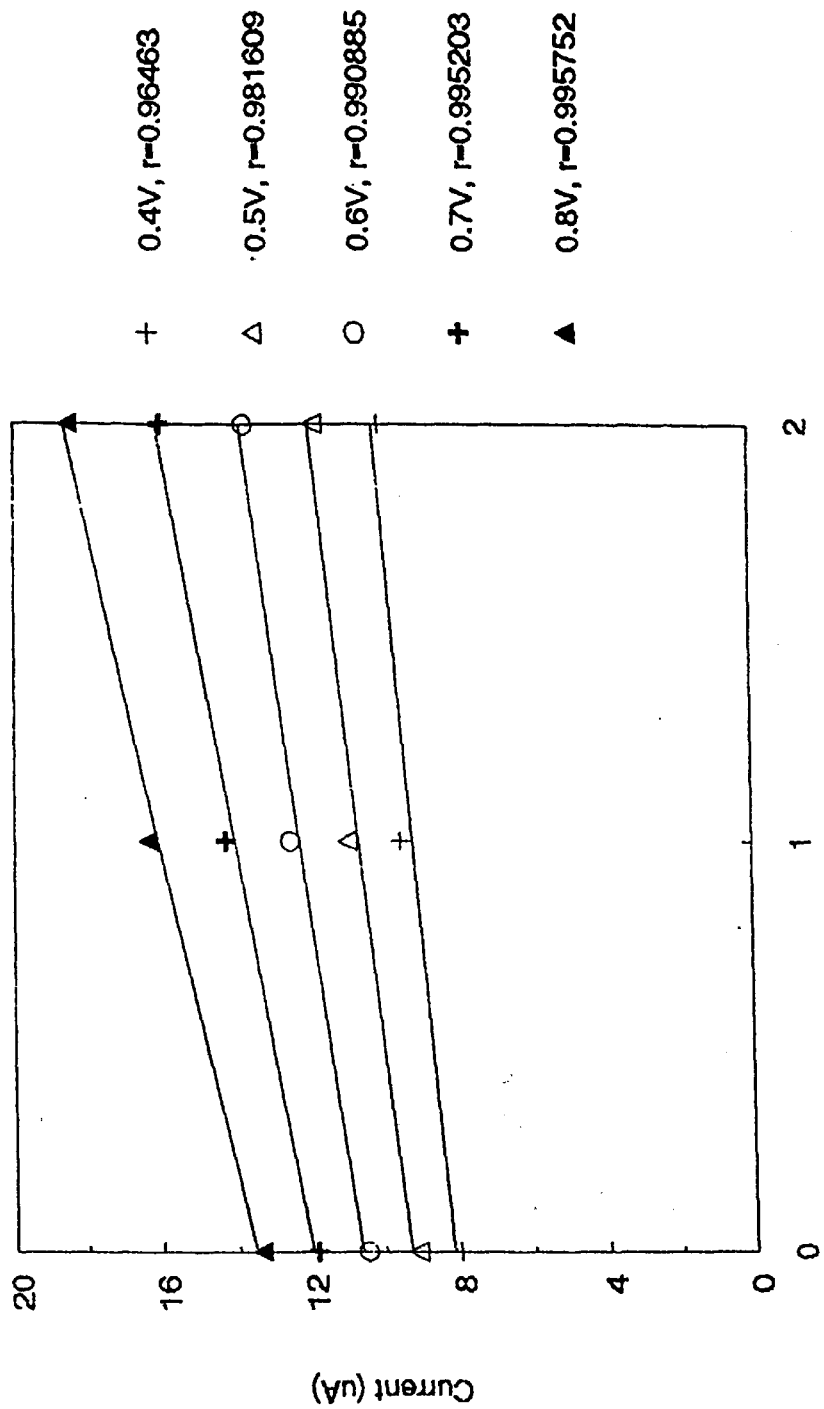
FIG. 15B is a graphical representation of the current output for the sensor of example no. 10 in relation to $SO_2$ concentrations from 0 to 2%.
Figure 16A:
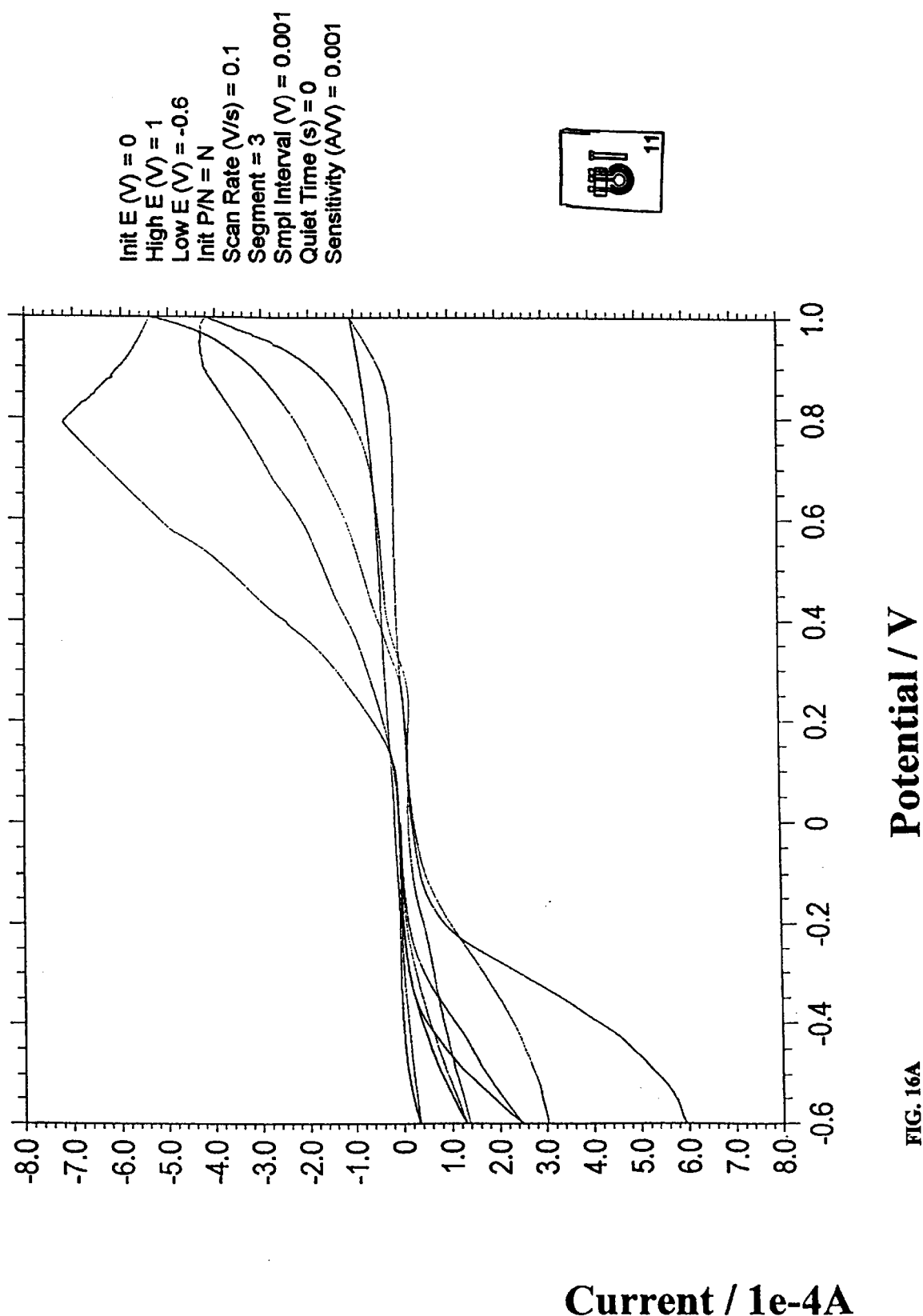
FIG. 16A is a graphical representation of the current output for the sensor of example no. 11 over a range of voltages from −0.6V to 1V.
Figure 16B:
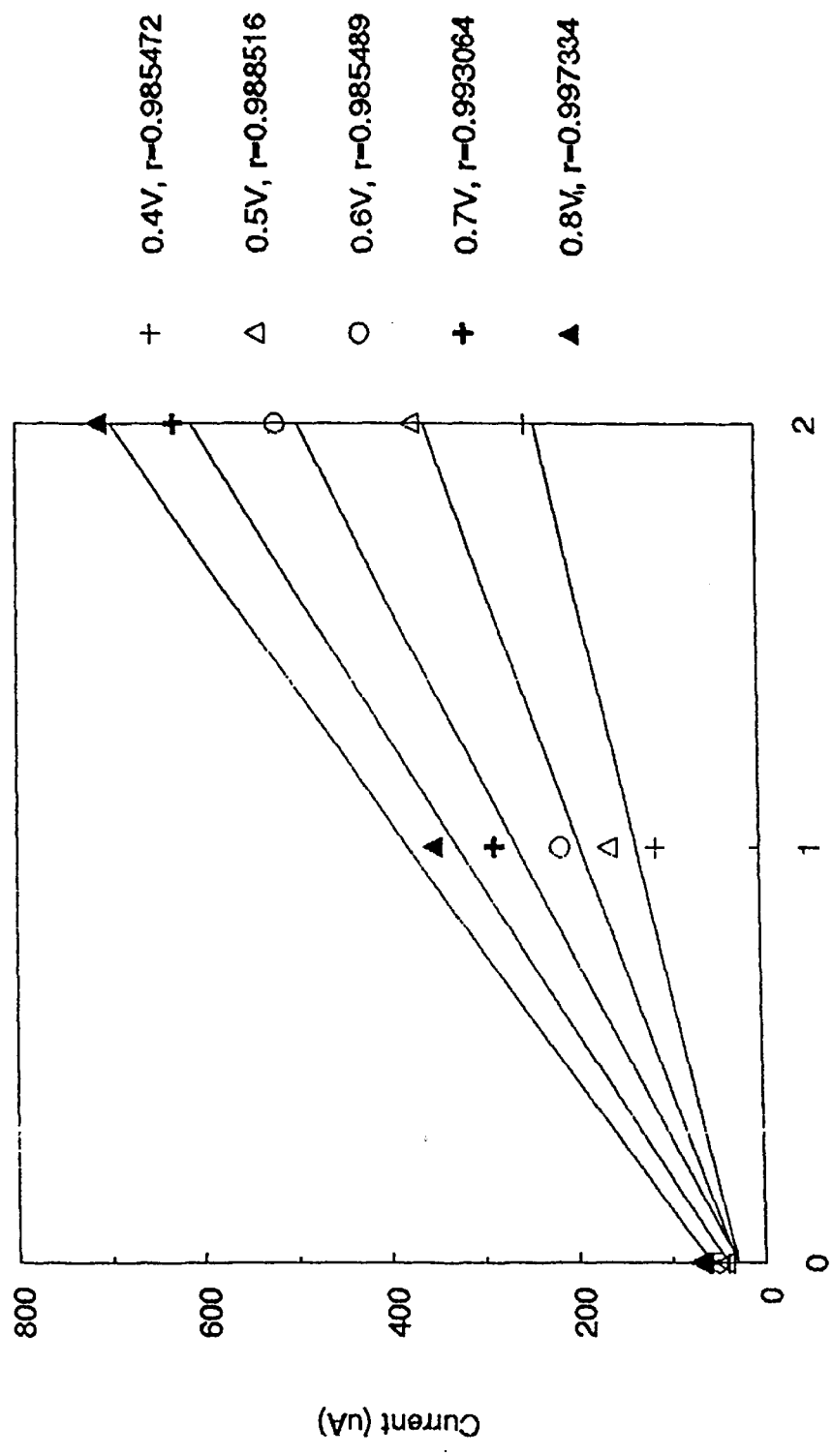
FIG. 16B is a graphical representation of the current output for the sensor of example no. 11 in relation to $SO_2$ concentrations from 0 to 2%.

The sizes of the electrodes varied on the micro-sensors that had rectangular configuration. However, as the sizes increased, the gaps between the working and the counter electrodes also increased. Because of this and the fact that, for these sensors, the difference in the gap distance is larger, making the gap distance have a greater effect on the sensors' current output, the current decreased as the gaps increased along with the sizes. This can be seen in comparing the graphs of the smaller sensor of example 9 (FIG. 14B) to that of the larger sensor of example 1 (FIG. 6B). Furthermore, because of the greater resistance created by the increased gap, the larger sensors also tend to have less accurate readings, as can be seen by the curve fitting coefficients which are further away from 1 (a perfect fit). Because examples 9 and 10 had very similar gap distances, but example 9 had larger electrodes, the effect created by size of the electrodes alone was able to be derived as well. In comparing these two, it was seen that example 9 (FIG. 14B) had higher current output than example 10 (FIG. 15B). From this, it was derived that, when the size of the electrodes increase without enlarging the gap, the current output increases as well.

The second type of configuration utilized was the semi-circle configuration used for the sensors of examples 4, 8, and 15. For these sensors, although the working and the counter electrodes are further apart at the position where the reference electrode circle has its horizontal diameter, the working and counter electrodes are closer to one another at the other portions. Moreover, at the lowest point of the electrodes, these two electrodes are adjacent to one another. Therefore, when the sizes are smaller, the output current is greater (FIGS. 9B, 13B, and 20B) in comparison to the rectangular configurations. However, when the sizes are larger the working and counter electrodes are further apart than in the rectangular configuration for a larger portion of the sensor, and the output current just about as small as in the rectangular configuration.

The sizes were varied within these "semi-circle" sensors as well. Once again, the gap distance increased more significantly than the size as the circular reference electrode increased. This again caused the current output to decrease significantly, as can be seen by comparing the graphs of example 4 (FIG. 9B) with currents in the 10–20 $\mu$A range, and example 8 (FIG. 13B) with currents in the 100–200 $\mu$A range. In this group, because of the configuration, it was not possible under the experimental conditions to enlarge the whole sensor without increasing the gap distance. Therefore, it was not feasible to compare the effects of just variations in the sizes.

The third configuration utilized concentric circles electrodes, which included examples 3, 11, 12 (which will be discussed later), and 14 (FIGS. 8B, 16B, 17B and 19B). This configuration had very small gaps between the working and the counter electrodes because, for these sensors, the counter electrode and the working electrode run adjacent to one another for the most part. Another difference is that the size of the working and counter electrodes on the concentric circles sensors are almost double the size of the working and counter electrodes on the semi-circles sensors because, on the concentric circles sensors, the circles are almost full. Due to these two main factors, these sensors have very high current outputs which are thousands of $\mu$A, and correspondingly have high sensitivity.

Within this group of sensors, there was also size variation. However, in increasing the sizes of the sensors, the gap was enlarged. Therefore, because of the enlarged gap size and the fact that the difference in the gap size for these was greater than that of the sensor size, the current output of the larger sensor of example 14 was less than that of the smaller sensor of example 3. However, because the difference in electrode size is so much more significant than that of the gap for sensors of examples 11 and 3, the current of the sensor of example 11 actually decreased in comparison to that of the sensor of example 3, despite the decreased gap size. Therefore, as demonstrated, increased electrode size does in fact lead to higher sensitivity.

Another type of configuration utilized was that of concentric ellipses, which includes the sensors of examples 2, 6, and 7. In this type of configuration, the working and the counter electrodes run adjacent to one another for the most part. However, when compared to the circular electrode designs, because these ellipses are elongated circles, the gap is slightly larger at the bottoms of these ellipses. Along the sides, the gaps are slightly smaller. Furthermore, the electrodes of the sensors with the concentric ellipses configuration are larger than those of the concentric circles, because they are longer vertically. Because of these factors, the range of the current output is a couple thousand microamperes higher than that of concentric circles, and this design therefore provides a higher sensitivity.

Within this group of sensors, the sizes were varied as well. However, in this set, the gap tended to change less than it did for other configurations. Therefore, for this group, the changes in the gaps are minor compared to the variations in the electrodes' sizes. Because of this, the effects of electrode size on the sensitivity and current output could be seen. By comparing the graphs of the three sensors' test runs and line fitting graphs, (FIGS. 7B, 11B, and 12B), it was observed that as the electrode size increased the current output increased significantly as well.

Finally, comparing the four configurations it was determined that the concentric designs were better. These configurations have the working and the counter electrodes adjacent to one another for a longer distance with smaller gaps. Furthermore, the surface area of the working and counter electrodes is larger in the concentric designs than other designs. These factors make the current outputs higher and the curve fitting coefficients somewhat closer to 1. The higher current outputs of the concentric designs make them not only more sensitive, but also more efficient, because the higher current outputs are easier to detect.

Figure 17A:
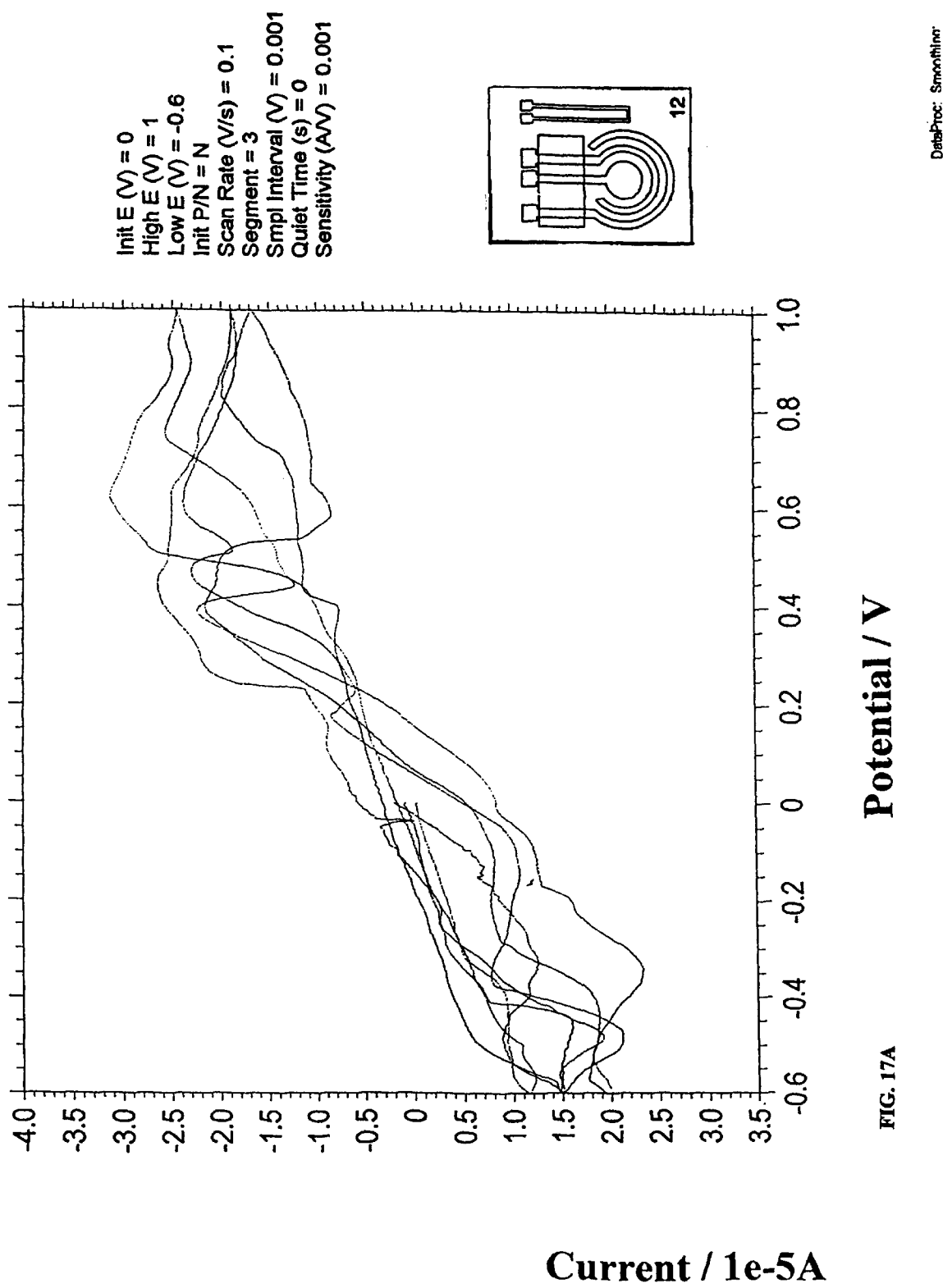
FIG. 17A is a graphical representation of the current output for the sensor of example no. 12 over a range of voltages from −0.6V to 1V.
Figure 17B:
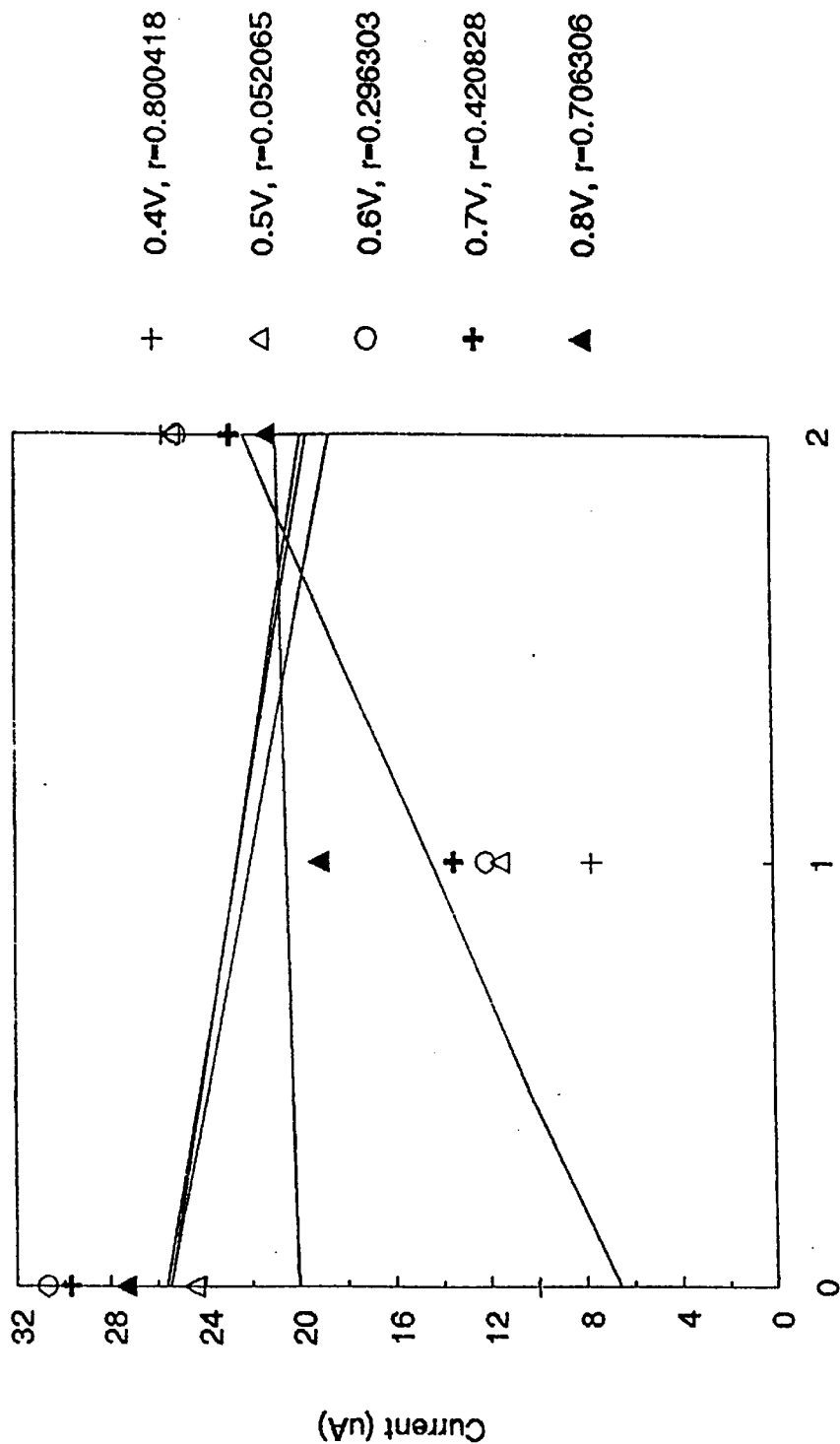
FIG. 17B is a graphical representation of the current output for the sensor of example no. 12 in relation to $SO_2$ concentrations from 0 to 2%.
Figure 18A:
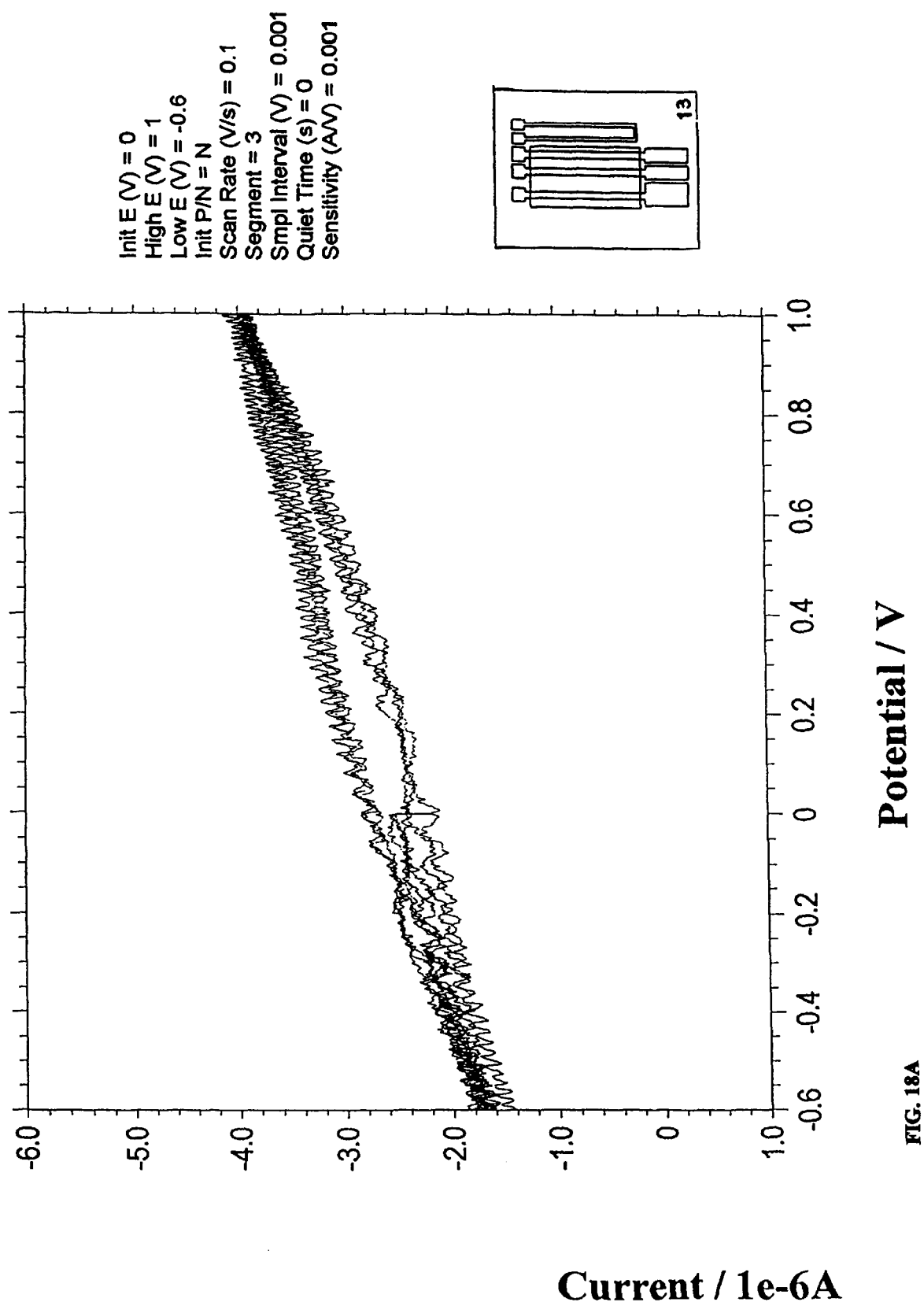
FIG. 18A is a graphical representation of the current output for the sensor of example no. 13 over a range of voltages from −0.6V to 1V.
Figure 18B:
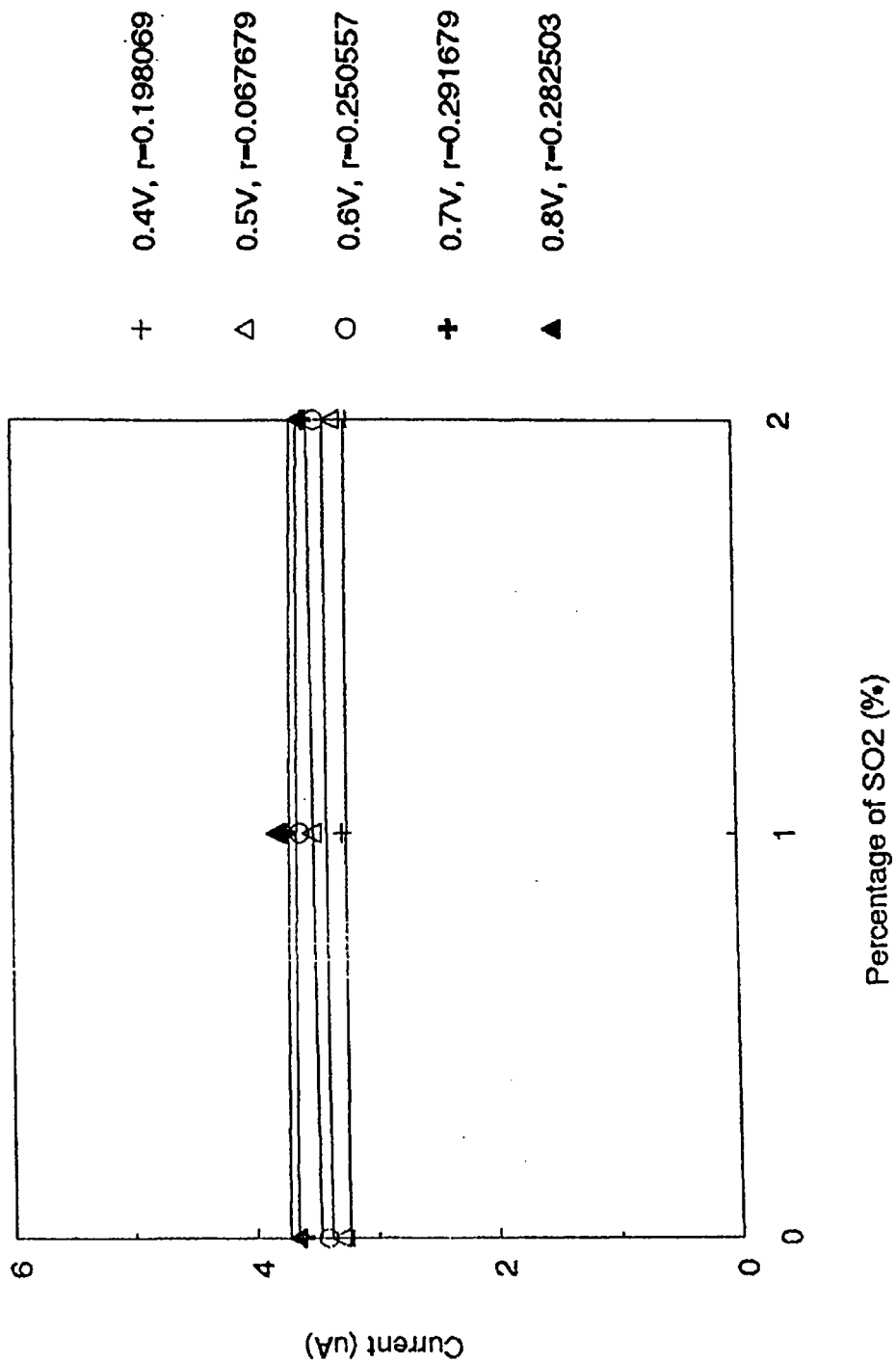
FIG. 18B is a graphical representation of the current output for the sensor of example no. 13 in relation to $SO_2$ concentrations from 0 to 2%.
Figure 19A:
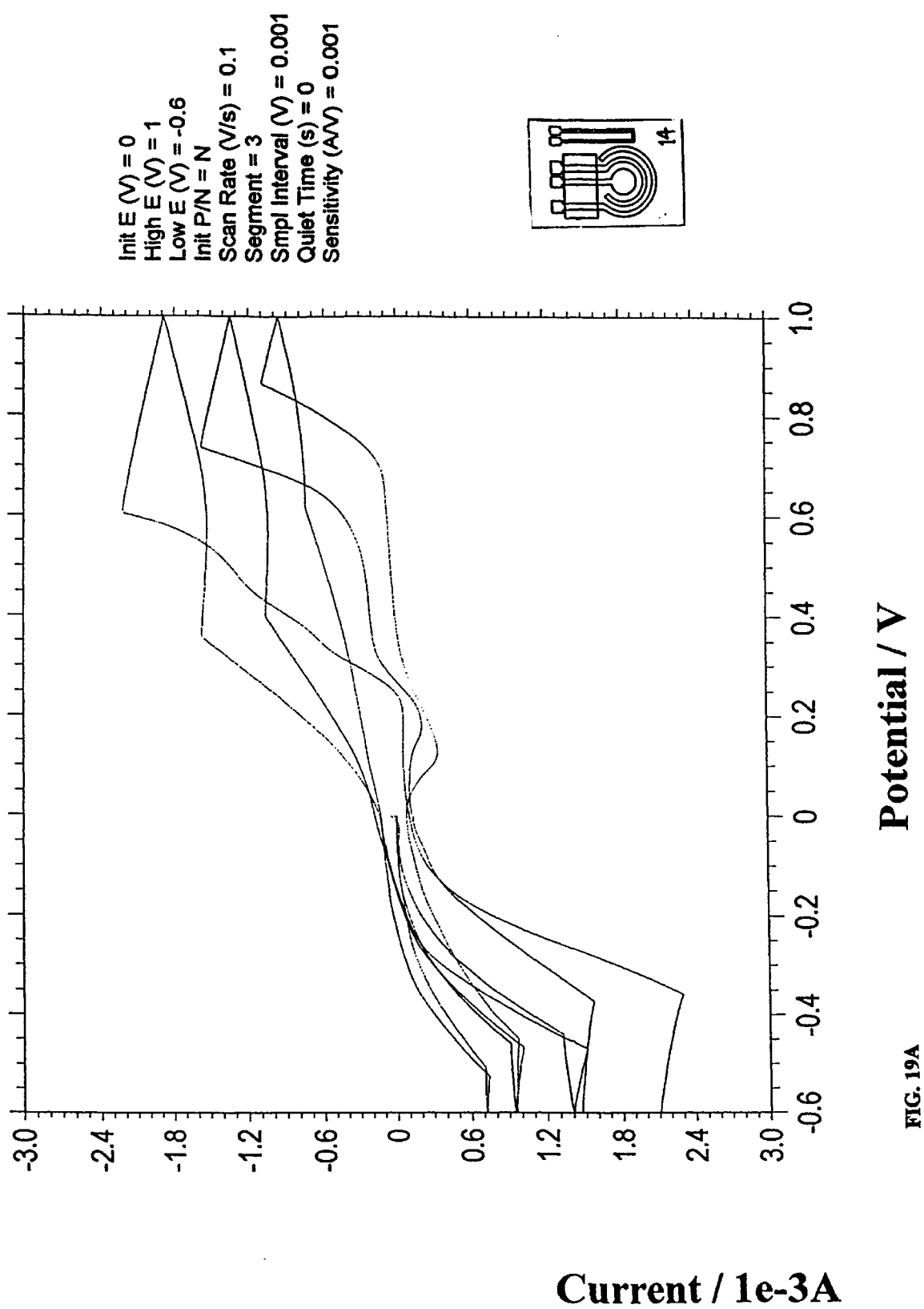
FIG. 19A is a graphical representation of the current output for the sensor of example no. 14 over a range of voltages from −0.6V to 1V.
Figure 19B:
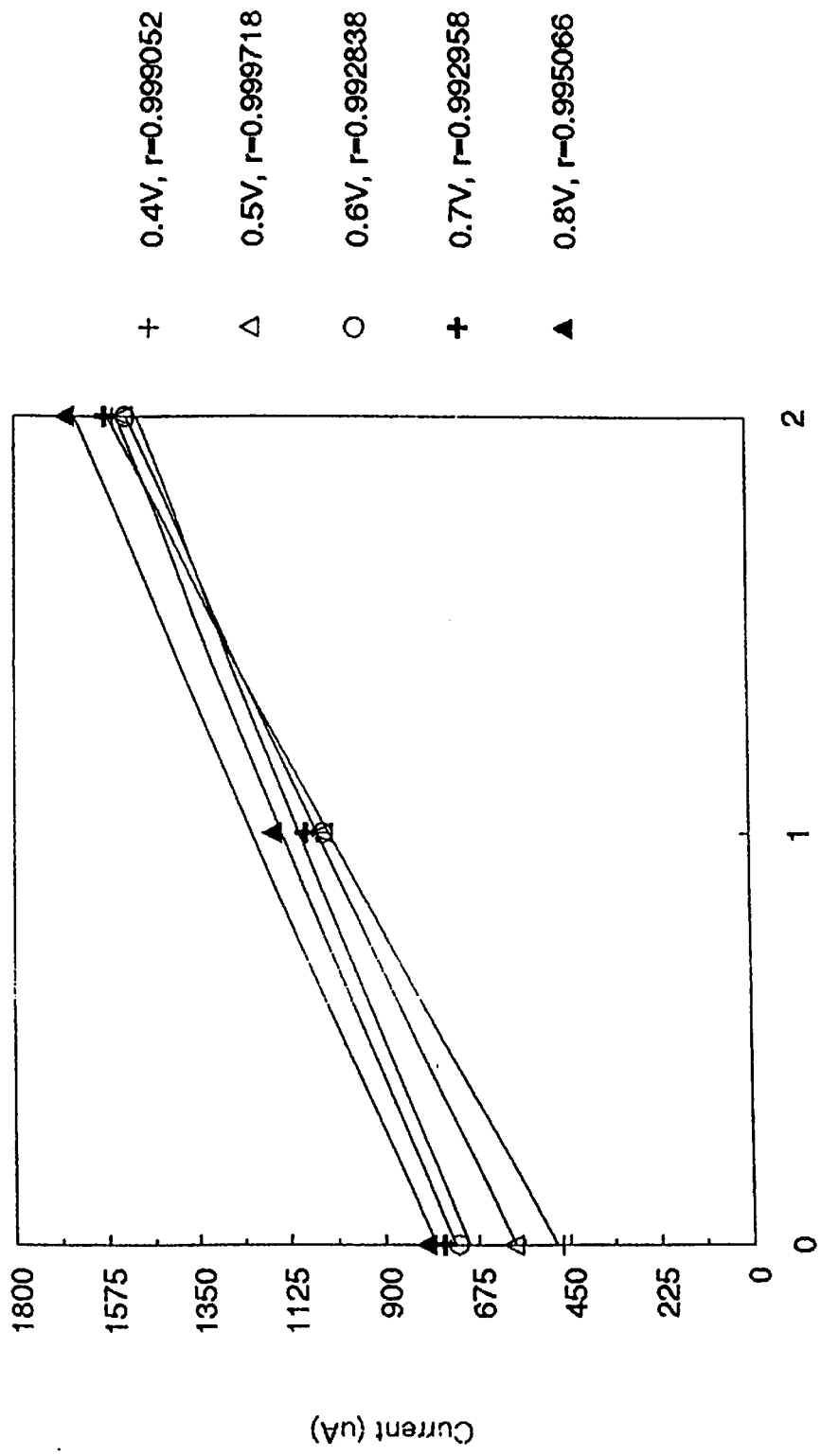
FIG. 19B is a graphical representation of the current output for the sensor of example no. 14 in relation to $SO_2$ concentrations from 0 to 2%.
Figure 20A:
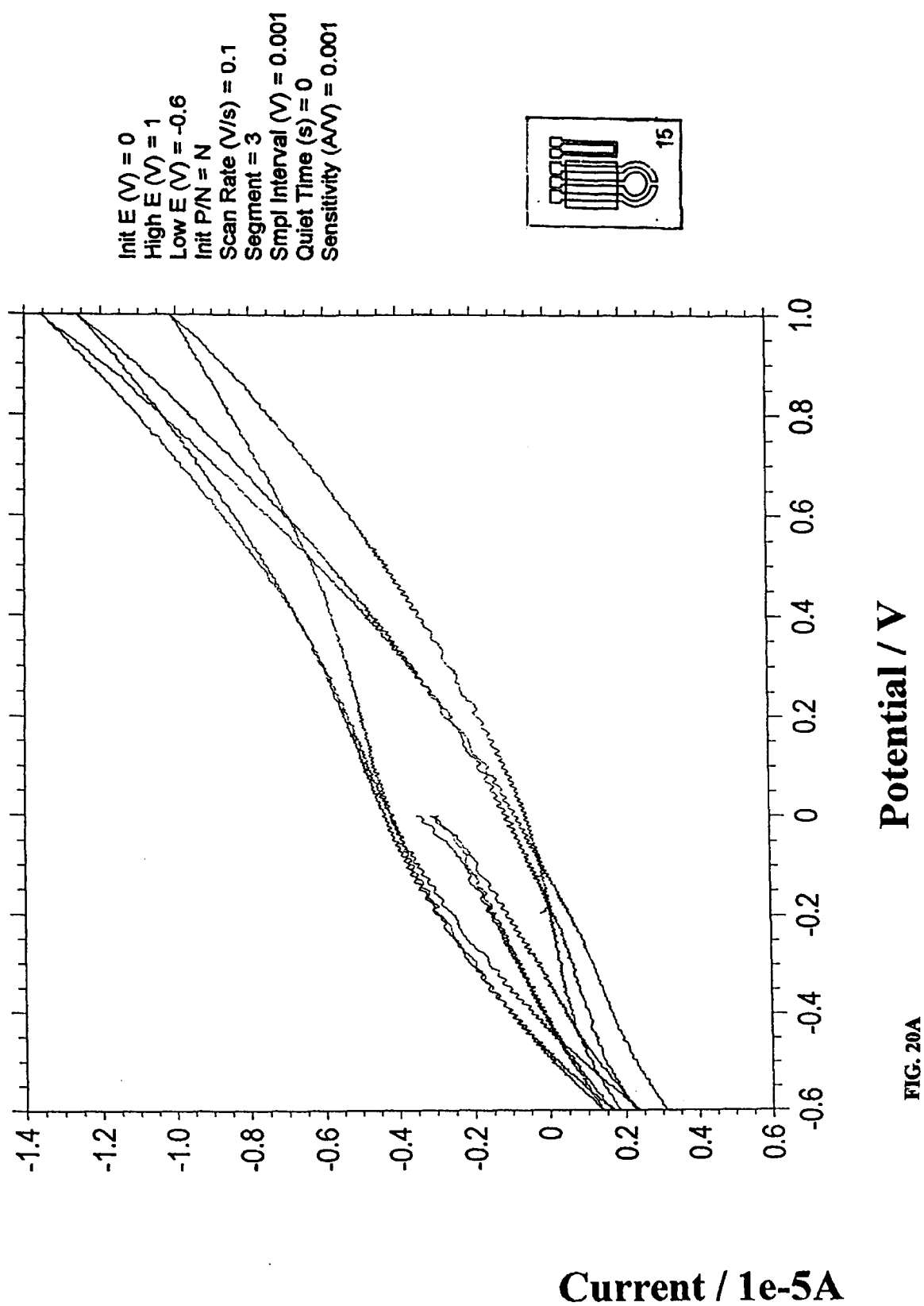
FIG. 20A is a graphical representation of the current output for the sensor of example no. 15 over a range of voltages from −0.6V to 1V.
Figure 20B:
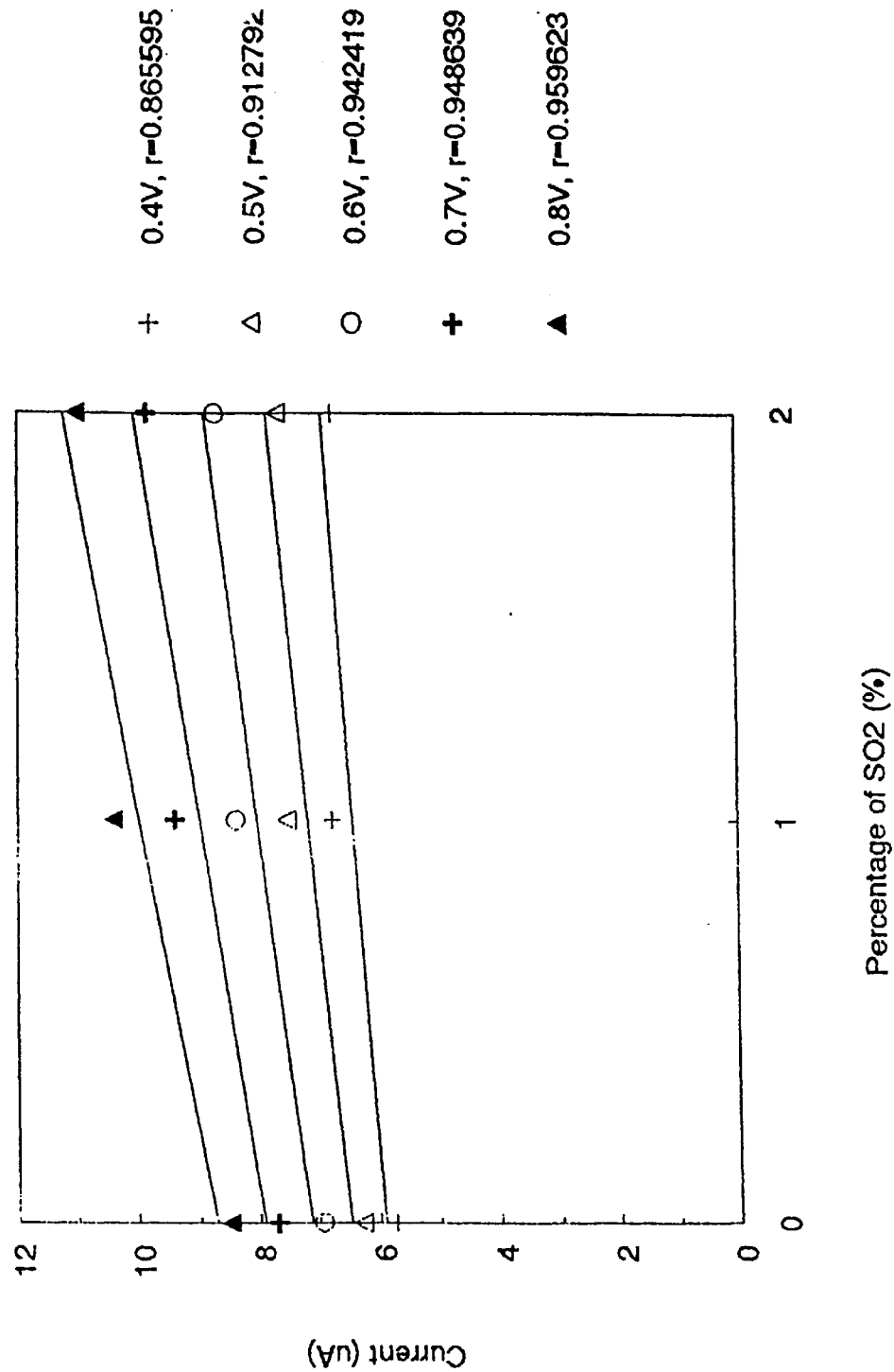
FIG. 20B is a graphical representation of the current output for the sensor of example no. 15 in relation to $SO_2$ concentrations from 0 to 2%.

Two sensors, of examples 12 and 13, were excluded from the above discussion, as these sensors were tested with a different setup (FIG. 4). In this other setup, the gas was not able to flow as freely through the region where the sensors were placed. Instead, the gas bounced back and forth within the beaker. Furthermore, the gas, instead of travelling through a gas tube first, was directly exposed to the sensors. Therefore, the test results were significantly different from the others. Although they fit the trends concerning size and gap, the coefficient r was very far from 1, and the line intersected and even had negative slopes (FIGS. 17B and 18B). Contributing factors could be either that the sensors were malfunctioning, or that the setup was not appropriate for this kind of testing.

As shown by the above examples, the current output/sensitivity did increase as the gap between working and counter electrodes decreased, as well as where the length of the working and counter electrodes were adjacent to one another increased. In the optimum configuration, it is preferable that the working and the counter electrodes are adjacent to one another for at least 90 percent of their exposed length, but more especially, it is preferable that the working and the counter electrodes are adjacent to one another for at least 90 percent of their entire length, having a gap therebetween of up to about 0.2 inches. There does exist a linear relationship between current outputs and concentrations, as can be seen by the fact that, for most of the sensors which functioned correctly, the coefficient r was relatively close to 1. Finally, the current output increased as electrode size increased when the gap size did not increase at the same time. If the gaps enlarged significantly as well, the current output actually decreased.

Part III: Design and testing of Examples 16–17

Figure 21:
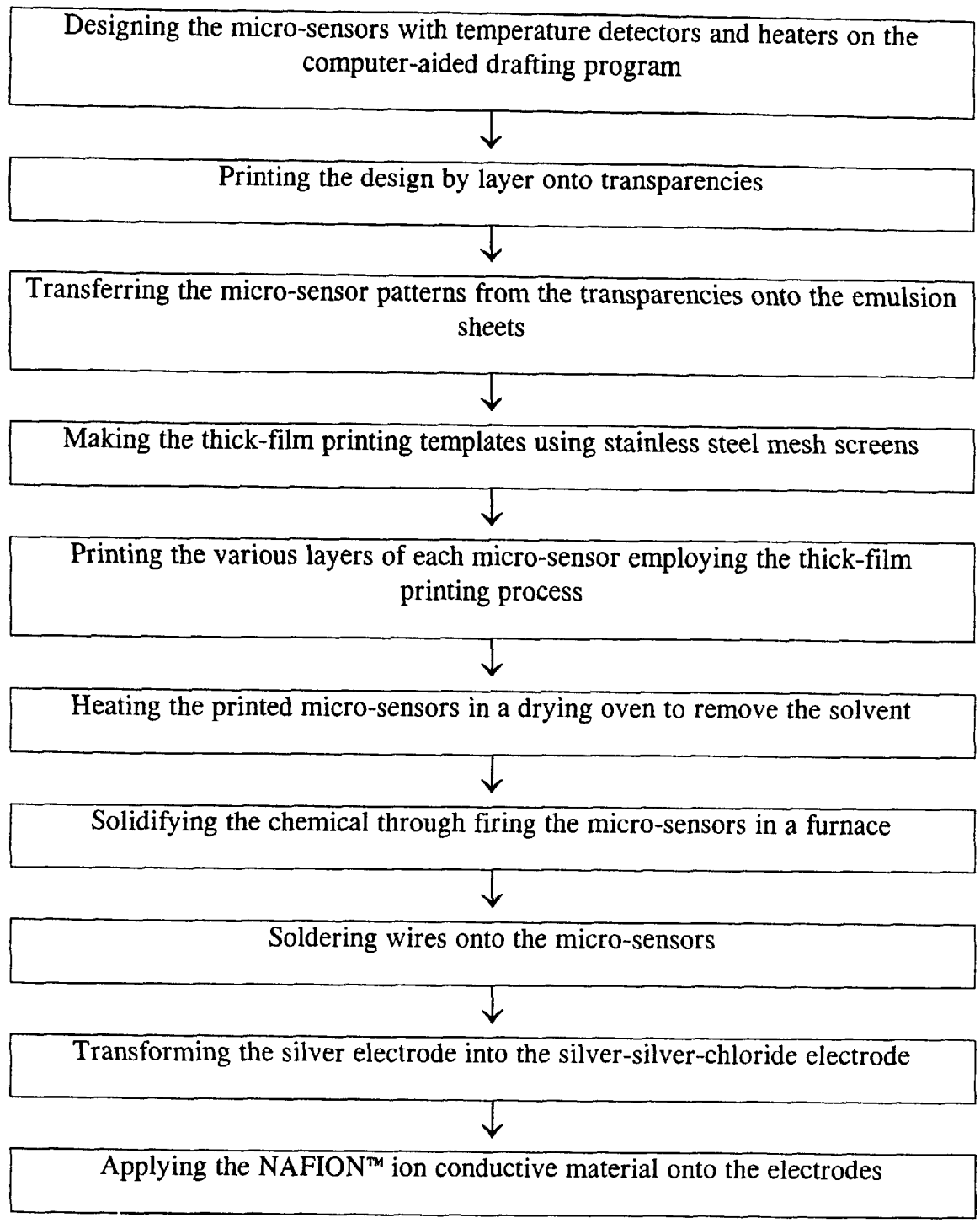
FIG. 21 is a flow chart of the process used to prepare the sensors of examples nos. 16 and 17.

Based on the above results, two additional sensor configurations were designed and prepared as shown on the flow chart of FIG. 21. Micro-sensor examples 16 and 17 were also prepared using a thick film technique, similar to examples 1–15, except that for examples 16 and 17, the designs were printed directly onto transparencies. The transparencies were then used to transfer the designs onto emulsion sheets.

Figure 22:
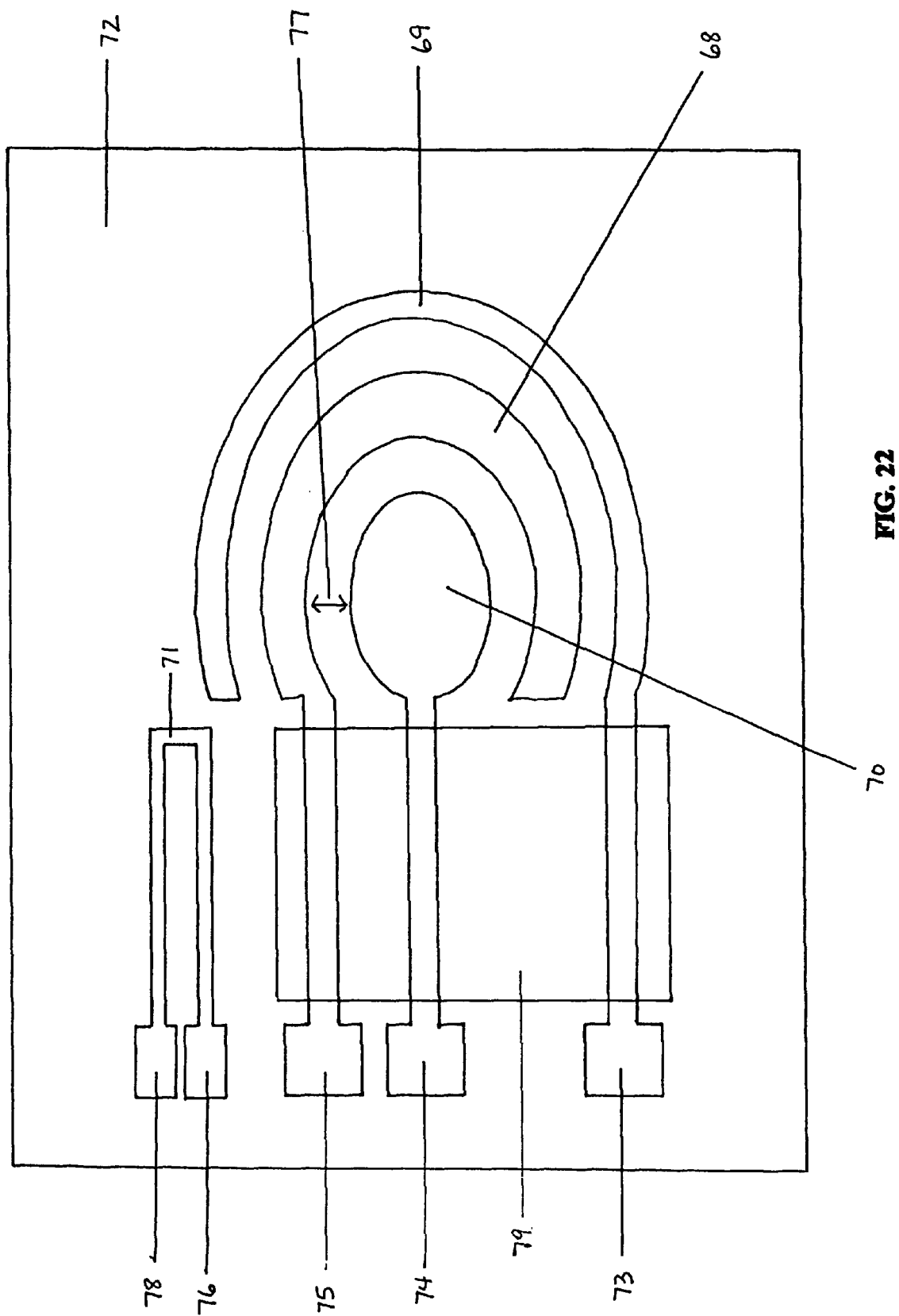
FIG. 22 is a schematic illustration of a further preferred sensor configuration, example no. 16, in accordance with the present invention, employing a substrate, working electrode, counter electrode, reference electrode, and temperature detector.

The configuration of sensor example 16 is shown in FIG. 22. The counter electrode 68 is interposed between the reference electrode 69 and the working electrode 70, with a gap 77 between the working and the counter electrodes. The reference electrode is disposed outwardly to the working and the counter electrodes. All three of these electrodes and the temperature detector 71 are applied to one side of the substrate 72. The contacts 73, 74, 75, 76, and 78 provide a connect portion of the sensor to which wires are soldered and covered with silicone paste. Insulator 79 protects the connect portion of the sensor device from the environment.

Figure 23:
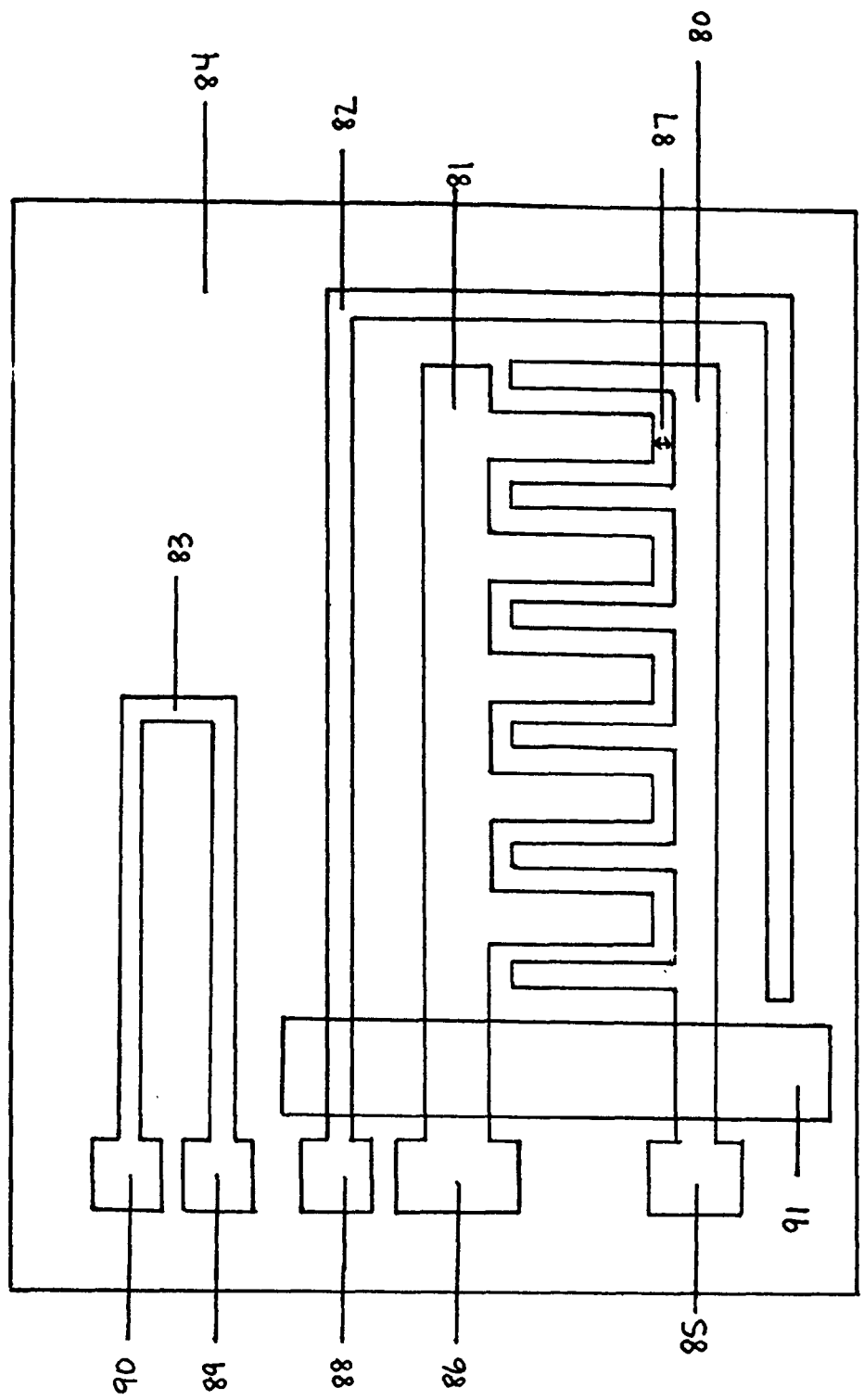
FIG. 23 is a schematic illustration of a further preferred sensor configuration, example no. 17, in accordance with the present invention, employing a substrate, working electrode, counter electrode, reference electrode, and temperature detector.

The configuration of sensor example 17 is shown in FIG. 23. The counter electrode 81 and the working electrode 80 are interdigitated, with a gap 87 between them, and with the reference electrode 82 disposed outwardly to them. All three of these electrodes and the temperature detector 83 are applied to one side of the substrate 84. The contacts 85, 86, 88, 89, and 90 provide a connect portion of the sensor to which wires are soldered and covered with silicone paste. Insulator 91 protects the connect portion of the sensor device from the environment.

Figure 24:
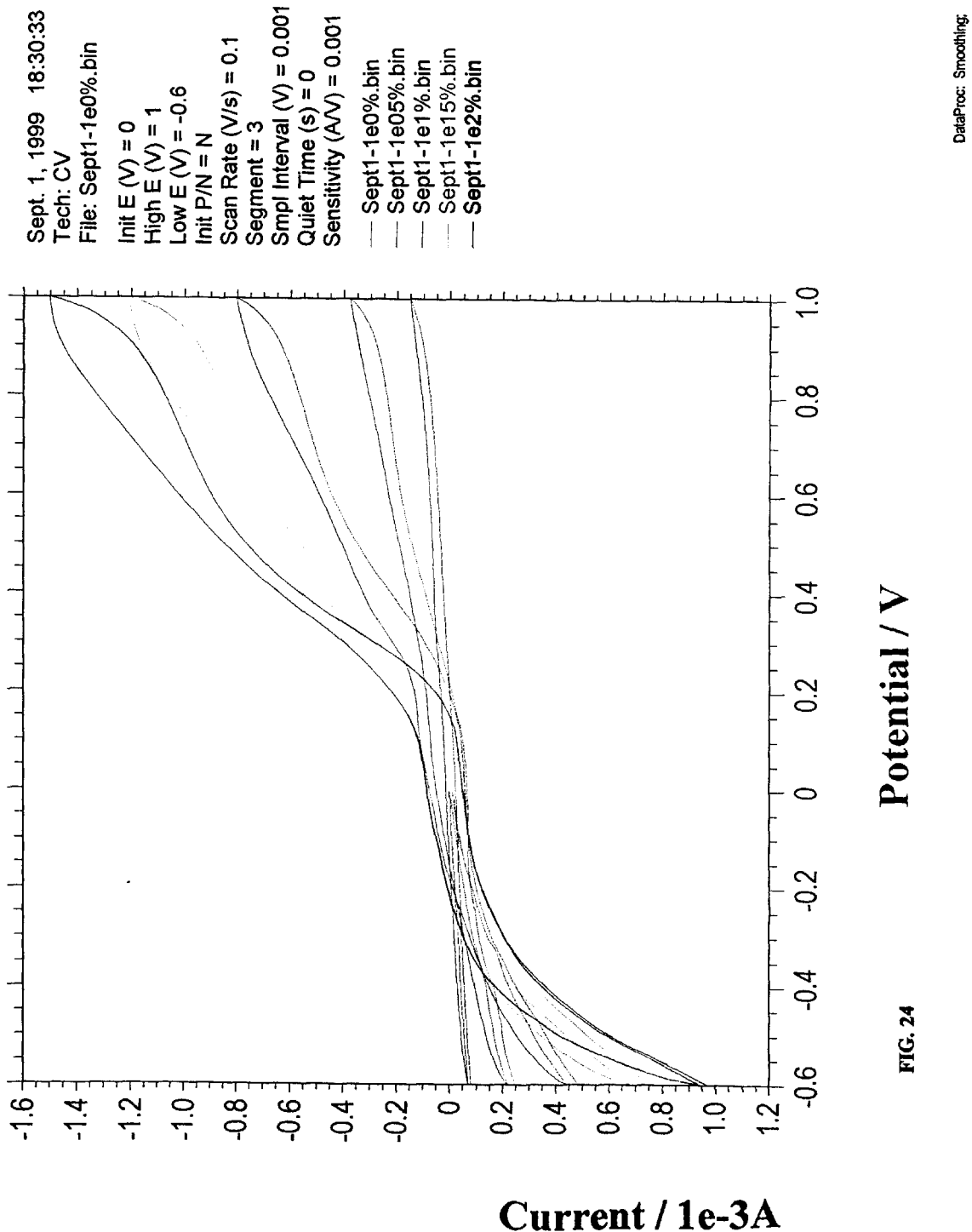
FIG. 24 is a graphical representation of the current output for the sensor of example no. 16 over a range of voltages from −0.6V to 1V.
Figure 25:
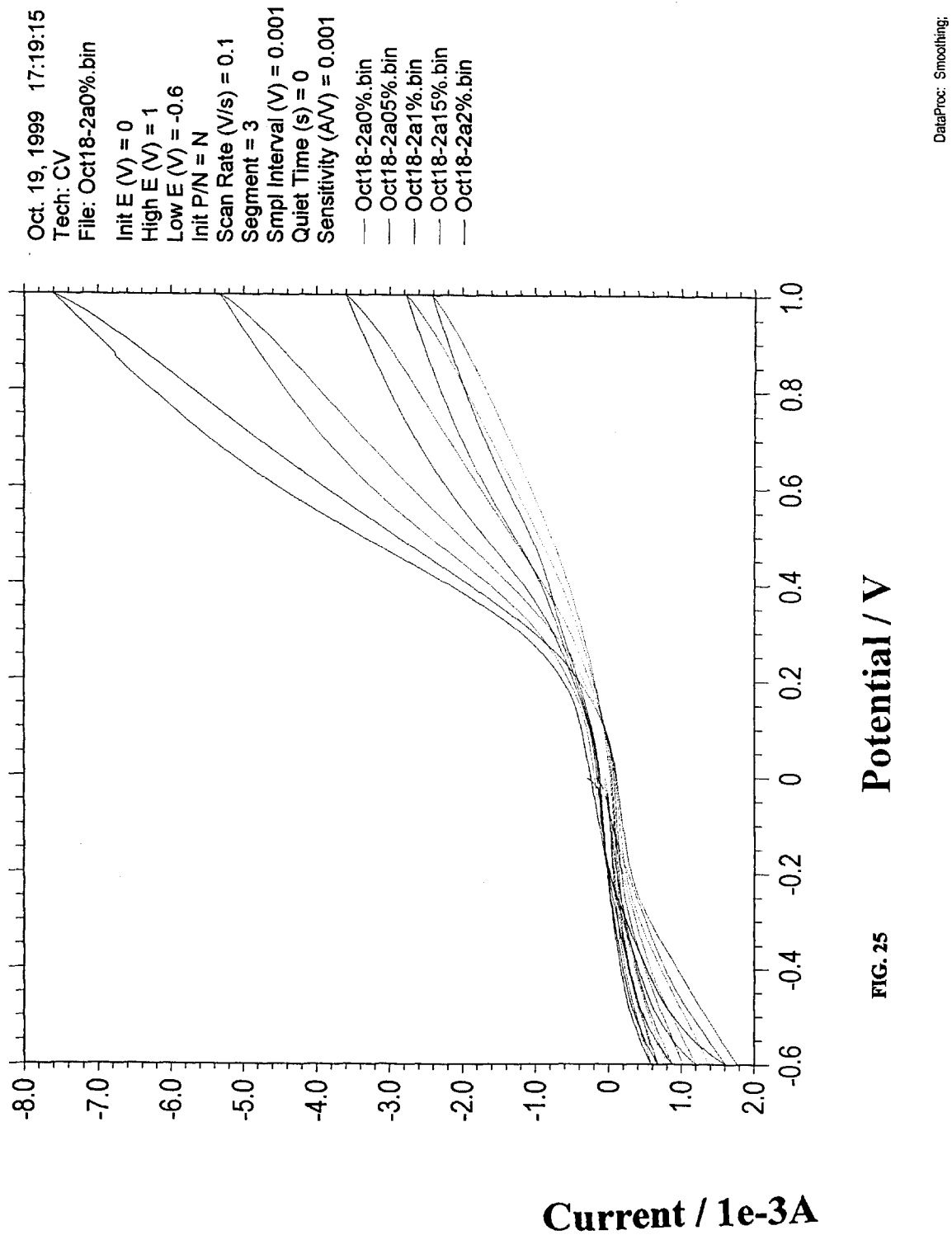
FIG. 25 is a graphical representation of the current output for the sensor of example no. 17 over a range of voltages from −0.6V to 1V.

Examples 16 and 17 were tested in accordance with the procedures used for example 1. Typical current outputs for sensor example 17 at various voltages and concentrations of sulfur dioxide are shown in Table 1. Graphical representations of the current output across a range of voltages from −0.6 to 1.0 for example 16 and 17 are shown in FIGS. 24 and 25, respectively.

TABLE I

| Microamperes of Current Output from Sensor Example 17 | | | | | |
|---|---|---|---|---|---|
| | 0% $SO_2$ | 0.5% $SO_2$ | 1.0% $SO_2$ | 1.5% $SO_2$ | 2.0% $SO_2$ |
| 0.4 V | 81.55 | 91.96 | 116.5 | 163.9 | 220.7 |
| 0.5 V | 106.1 | 128.7 | 170.4 | 247.3 | 339.9 |
| 0.6 V | 138.8 | 167.5 | 221.3 | 324.8 | 451.9 |
| 0.7 V | 169.9 | 201.1 | 264.0 | 388.4 | 545.7 |
| 0.8 V | 196.1 | 229.4 | 299.5 | 441.1 | 624.8 |
| 0.9 V | 219.9 | 254.4 | 331.3 | 487.9 | 692.9 |

Figure 26:
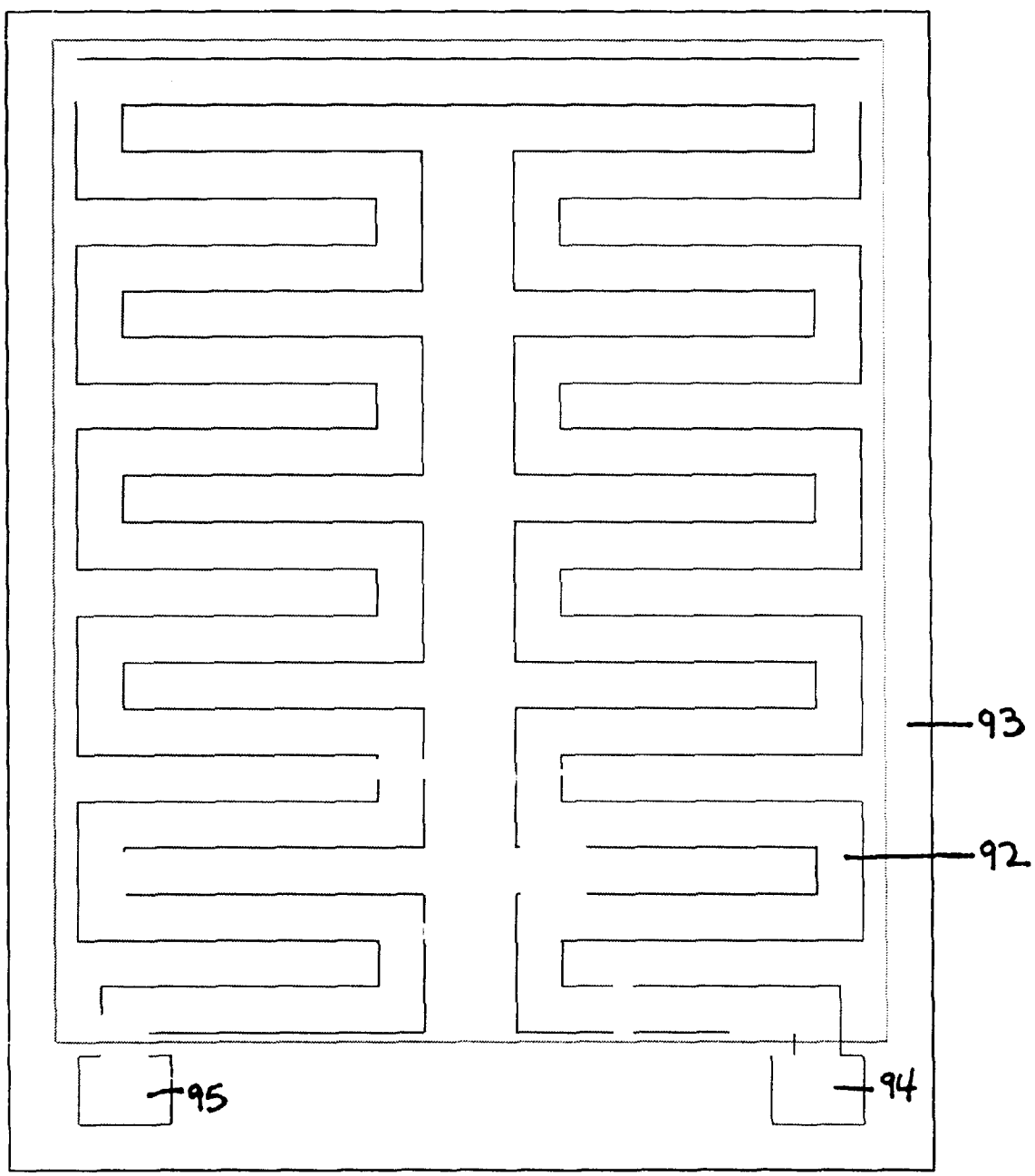
FIG. 26 is a schematic representation of a preferred heater configuration, in accordance with the present invention.

The two sensor examples 16 and 17 also include a heater of platinum, printed on the opposite side of the substrate. The design of the heater is shown in FIG. 26. The heater is a substantially serpentine pattern of platinum 92 printed on a substrate 93. Contacts 94 and 95 provide sites to connect wires.

The temperature detector can be calibrated by measuring the resistance at various temperatures. The temperature detector can then be used to test the heater and to correlate the required voltage inputs necessary to maintain the temperature of interest. In actual operation, such as in an industrial smokestack, the heater will operate to maintain the micro-sensor device at a constant temperature, preferably above the temperature of the emission gas in contact with the sensor, thereby insuring the accuracy of the calibration for sulfur dioxide detection or monitoring.

Other sensor configurations are possible according to the present invention, but a more preferred configuration has a portion of the working and counter electrodes interdigitated with a small gap between them, on the order of about 0.2 inches or less. Furthermore, in this embodiment, the reference electrode is disposed outwardly to the working and the counter electrodes. Preferably the micro-sensor also includes a mesh screen to protect it against harmful dust, ashes, or particles, which may disrupt the accuracy of the measurements. The micro-sensor may be further adapted to perform an actuating function, such as to trigger the spraying of a certain basic substance, such as calcium hydroxide, which will scrub or neutralize the sulfur dioxide.

Advantageously, the micro-sensor device of the present invention, prepared using a thick film technique, is relatively inexpensive to manufacture, install, and operate. For this reason, it is possible to use two or more sensors and operate them in a differential mode. In a preferred embodiment, two substantially identical sensors are used. One sensor is optimized for sulfur dioxide detection, through the choice of operating temperature, electrolyte membrane, the use of an electrode catalyst, or by another method, and the second sensor is adapted to detect interference from other chemical species, such as being operated at ambient temperature. The level of sulfur dioxide can then be determined by subtracting the signal due to the interference from the signal of the sulfur dioxide detecting sensor. Such a method of differential operation can overcome the problems of interference that are known in the art of electrochemical sensors. The method of this embodiment comprises contacting the emission gas with a first inventive sensor, measuring the current output of the sensor adapted to detect sulfur dioxide generating a first signal based on the current output of the sensor, providing a second inventive sensor, which has been adapted to detect interference from other chemical species, contacting the emission gas with the second sensor, measuring the current output of the second sensor, generating a second signal, and subtracting the second signal from the first signal. This signal can then be used to activate a display device, a recording means, an alarm device, and/or a compensating means.

It is demonstrated that the electrochemical micro-sensor device of the present invention can be used to detect sulfur dioxide emissions cheaply and quite effectively in various locations, including the upper part of an industrial smokestack, where the temperatures are lower. When $SO_2$ is detected, the sensor generates a signal that is sent to an indicator, such as an alarm, or visual display, or to a recorder, making it possible to study process trends and track emissions over a period of time. Current generated can be measured by a potentiostat, for example, or analyzed by computer or another electronic measuring device. The sensor can generate a signal that is amplified if necessary, and that triggers an actuator, to actuate a neutralizing apparatus such as an existing scrubber system only when a predetermined level of sulfur dioxide is detected, allowing more efficient utilization of the scrubber system. The sensor could also be used to initiate diversion of the emission gas when necessary into a cold trap system or reservoir by opening or closing a valve to allow further treatment of the emission gas, or to initiate shutdown of the chemical or physical process producing the emissions.

It should now be apparent that various embodiments of the present invention accomplish the object of this invention. It should be appreciated that the present invention is not limited to the specific embodiments described above, but includes variations, modifications, and equivalent embodiments defined by the following claims.

What is claimed is:

1. A method of detecting or monitoring sulfur dioxide in an emission gas comprising contacting the emission gas with an electrochemical micro-sensor device comprising a substrate supporting an arrangement of a working electrode, a reference electrode, and a counter electrode, wherein a first portion of the electrodes is covered with an insulator, and a second portion of the electrodes is covered with an electrolyte, and wherein the electrodes and the insulator are applied to the substrate using a thick film technique;

maintaining the micro-sensor device at a constant temperature higher than the temperature of the emission gas contacting the micro-sensor device;

measuring the current output of the micro-sensor device;

determining if the current output indicates the presence of sulfur dioxide; and generating a signal.

2. The method of claim 1, further comprising transmitting the signal to at least one device selected from the group consisting of display devices, recording means, alarm devices, and compensating means.

3. The method of claim 2, wherein the compensating means comprises a scrubber system, a diversionary means, a trapping and condensing means, or a combination thereof.

4. The method of claim 1, wherein said step of determining if the current output indicates the presence of sulfur dioxide comprises:

generating a first signal based on the current output of the micro-sensor device;

providing at least a second sensor substantially identical to the micro-sensor device, wherein the second sensor is adapted to detect interference from other chemical species besides sulfur dioxide;

contacting the emission gas with the second sensor;

measuring the current output of the second sensor;

generating a second signal based on the current output of the second sensor; and subtracting the second signal from the first signal.

5. The method of claim 1, wherein the substrate is an insulating material selected from the group consisting of plastic, glass, ceramic, quartz, and mixtures thereof.

6. The method of claim 1, wherein the working electrode and counter electrode are each independently selected from the group consisting of gold, platinum, palladium, silver, silver-silver chloride, carbon, and mixtures thereof.

7. The method of claim 1, wherein the reference electrode comprises one of silver-silver chloride and mercury-mercuric chloride.

8. The method of claim 1, wherein said first portion of the electrodes is a connect portion and said second portion of the electrodes is a sensing portion, and wherein the connect portion connects the electrode to an electrical circuit, and is protected from the environment by the insulator, and wherein the sensing portion is exposed to the environment via the electrolyte.

9. The method of claim 1, wherein the electrolyte comprises an ion conductive resin or membrane.

10. The method of claim 1, further comprising a temperature detector, optionally wherein the temperature detector comprises platinum.

11. The method of claim 1, wherein the micro-sensor device further comprises a heater, optionally wherein the heater comprises a substantially serpentine pattern of conductive material printed onto the opposite side of the substrate from the three electrodes.

12. The method of claim 1, wherein the working and counter electrodes are disposed adjacent to each other, with a gap therebetween of less than or equal to about 0.2 inches over at least 90 percent of their length.

13. The method of claim 1, wherein the arrangement of three electrodes is a substantially elliptical arrangement wherein the working and counter electrodes are substantially concentrically oriented with respect to each other without the reference electrode interposed between them.

14. The method of claim 1, wherein the arrangement of three electrodes is a substantially circular arrangement wherein the working and counter electrodes are substantially concentrically oriented with respect to each other without the reference electrode interposed between them.

15. The method of claim 1, wherein the arrangement of three electrodes is a rectangular arrangement wherein the working and counter electrodes are substantially concentrically oriented with respect to each other without the reference electrode interposed between them.

16. The method of claim 1, wherein the arrangement of the three electrodes includes an adjacent working electrode and counter electrode, wherein portions of the working electrode are interdigitated with portions of the counter electrode, and wherein the reference electrode is disposed outwardly from the working and counter electrodes.

17. The method of claim 1, wherein the insulator is an insulating material selected from the group consisting of glass, and a glass-containing dielectric material.

18. The method of claim 1, wherein the thick film technique comprises the steps of:
   providing at least one template containing a pattern for the arrangement of the three electrodes;
   contacting the substrate with the template;
   applying at least one electrode precursor ink, and insulator precursor ink onto the template/substrate to form a sensor configuration according to the template pattern;
   drying the sensor configuration;
   firing the sensor configuration; and
   covering a portion of the three electrodes with an electrolyte.

* * * * *